(12) United States Patent
Marshall et al.

(10) Patent No.: US 10,421,778 B2
(45) Date of Patent: Sep. 24, 2019

(54) ISOFORM-SELECTIVE LYSINE DEACETYLASE INHIBITORS

(71) Applicant: WASHINGTON UNIVERSITY, St. Louis, MO (US)

(72) Inventors: Garland R. Marshall, Clayton, MO (US); George B. Kyei, St. Louis, MO (US); Michael D. Onken, St. Louis, MO (US); Lee Ratner, St. Louis, MO (US); Nandarapu Damodara Reddy, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/570,967

(22) PCT Filed: May 5, 2016

(86) PCT No.: PCT/US2016/030995
§ 371 (c)(1),
(2) Date: Oct. 31, 2017

(87) PCT Pub. No.: WO2016/179398
PCT Pub. Date: Nov. 10, 2016

(65) Prior Publication Data
US 2018/0230181 A1  Aug. 16, 2018

Related U.S. Application Data

(60) Provisional application No. 62/156,986, filed on May 5, 2015.

(51) Int. Cl.
*A61K 38/12* (2006.01)
*C07K 5/02* (2006.01)
*A61P 25/28* (2006.01)
*A61P 35/00* (2006.01)
*A61K 38/00* (2006.01)

(52) U.S. Cl.
CPC ............ *C07K 5/0202* (2013.01); *A61P 25/28* (2018.01); *A61P 35/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 5,149,778 A | * | 9/1992 | Adams ............... C07K 7/56 514/934 |
| 8,217,076 B2 | | 7/2012 | Williams et al. |
| 8,394,810 B2 | | 3/2013 | Van Duzer et al. |
| 8,513,290 B2 | | 8/2013 | Williams et al. |
| 2005/0277583 A1 | | 12/2005 | Yoshida et al. |
| 2011/0060021 A1 | | 3/2011 | Cheng et al. |
| 2013/0108655 A1 | | 5/2013 | Zabrocki et al. |
| 2013/0224232 A1 | | 8/2013 | Zabrocki et al. |
| 2014/0031400 A1 | | 1/2014 | Luesch et al. |
| 2014/0093449 A1 | | 4/2014 | Williams et al. |

FOREIGN PATENT DOCUMENTS

| | | |
|---|---|---|
| CN | 101781321 A | 7/2010 |
| WO | 2009126315 A2 | 12/2009 |
| WO | 2010009334 A1 | 1/2010 |
| WO | 2011113013 A2 | 9/2011 |

OTHER PUBLICATIONS

Thakkar, Amit et al, "GLobal analysis of peptide cyclization efficiency." ACS Comb. Sci. (2013) 15(2) p. 120-129.*
Archin, N.M, et al., Expression of latent human immunodeficiency type 1 is induced by novel and selective histone deacetylase inhibitors, 2009, AIDS, 23:1799-1806, 8 pages.
Bowers, A.A., et al., "Synthesis and Conformation—Activity Relationships of the Peptide Isosteres of FK228 and Largazole," 2009, JAGS, 131/8:2900-2905, 6 pages.
Bowers, A.A., et al., "Synthesis and Histone Deacetylase Inhibitory Activity of Largazole Analogs: Alteration of the Zinc-Binding Domain and Macrocyclic Scaffold," 2009, Org Lett, 11/6:1301-1304, 4 pages.
Bowers, A.A., et al., "The Total Synthesis and Biological Mode of Action of Largazole: A Potent Class I Histone Deacetylase (HDAC) Inhibitor," 2008, JACS, 130/33:11219-11222, 13 pages.
Chou, C.J., et al., "Pimelic Diphenylamide 106 Is a Slow, Tight-binding Inhibitor of Class I Histone Deacetylases," 2008, J Biol Chem, 283/51:35402-35409, 17 pages.
Che, Y., et al., "Privileged scaffolds targeting reverse-turn and helix recognition," 2008, Expert Opin Ther Targets, 12/1, 14 pages.
Che, Y., et al., "Engineering Cyclic Tetrapeptides Containing Chimeric Amino Acids as Preferred Reverse-Turn Scaffolds," 2006, J Med Chem, 49:111-124, 14 pages.
Cole, K.E., et al., "Structural Basis of the Antiproliferative Activity of Largazole, a Depsipeptide Inhibitor of the Histone Deacetylases," 2011, 133/32:12474-12477, 9 pages.
Delcuve, G.P., et al., "Roles of histone deacetylases in epigenetic regulation: emerging paradigms from studies with inhibitors," 2012, Clinical Epigenetics, 4/5, 13 pages, http://www.clinicalepigeneticsjournal.com/content/4/1/5, downloaded Jan. 1, 2015.
Deng, K., et al., "Broad CTL response is required to clear latent HIV-1 due to dominance of escape mutations," 2015, Nature, 517, 16 pages.
Falkenberg, K.J., et al., "Histone deacetylases and their inhibitors in cancer, neurological diseases and immune disorders," 2014, Drug Discovery, 13/673-691, 19 pages.
Falkenberg, K.J., et al., "Histone deacetylases and their inhibitors in cancer, neurological diseases and immune disorders," 2014, Drug Discovery, Supplementary Information, Table 1 and References, 4 pages.
Falkenberg, K.J., et al., "Histone deacetylases and their inhibitors in cancer, neurological diseases and immune disorders," 2014, Drug Discovery, Supplementary Information, Table 2A-2C and References, 6 pages.

(Continued)

*Primary Examiner* — Fred H Reynolds
(74) *Attorney, Agent, or Firm* — Stinson LLP

(57) ABSTRACT

Isoform-selective lysine deacetylase inhibitors are described. Inhibitors of the lysine deacetylase enzyme are useful as antitumor drugs and for treating addiction, asthma, cardio-vascular disease, immunosuppression, neurodegenerative diseases, sepsis, sickle-cell disease, uveal melanoma and termination of viral latency, particularly HIV-1 latency.

19 Claims, 18 Drawing Sheets

(56) References Cited

OTHER PUBLICATIONS

Guerra-Bubb, J.M., et al., "Synthesis and HDAC inhibitory activity of isosteric thiazoline-oxazole largazole analogs," 2013, Bioorganic & Medicinal Letters, 23:6025-6028, 4 pages.

Hamer, D.H., "Can HIV be Cured? Mechanisms of HIV persistence and strategies to combat it," 2004, Curr HIV Res, 212:99-111, Abstract Only, 2 pages.

Jordan, A., et al., "HIV Reproducibly Establishjes a Latent Infection After Acute Infection of T Cells in vitro," 2003, The EMBO Journal, 22/8:1868-1877, 10 pages.

Keedy, K.S., et al., "A Limited Group of Class I Histone Deacetylases Acts to Repress Human Immunodeficiency Virus Type 1 Expression," 2009, J Virology, 83/10:4749-4756, 8 pages.

Kim, M., et al., "A Primary CD4+ T cell Model of HIV-1 Latency Established After Activation Through the T cell Receptor and Subsequent Return to Quiescence," 2014, Nature Protocols, 9/12:2755-2770, 16 pages.

Kozikowski, A.P., "Use of the Nitrile Oxide Cycloaddition (NOC) Reaction for Molecular Probe Generation: A New Class of Enzyme Selective Histone Deacetylase Inhibitors (HDACIs) Showing Picololar Activity at HDAC6," 2008, J Med Chem, 51:4370-4373, 4 pages.

Lassen, K.G., "A Flexible Model of HIV-1 Latency Permitting Evaluation of Many Primary CD4 T-Cell Reservoirs," 2012, PLoS ONE, 7/1:e30176, 12 pages.

Li, X., et al., "Biological Evaluation of New Largazole Analogues: Alteration of Macrocyclic Scaffold with Click Chemistry," 2013, ACS, Med Chem Lett, 2013, 4:132-136, 5 pages.

Montero, A., et al., "Design, Synthesis, Biological Evaluation, and Structural Characterization of Potent Histone Deacetylase Inhibitors Based on Cyclic α/β-Tetrapeptide Architectures," 2009, J Am Chem Soc, 132/8:3033-3041, 22 pages.

Mwakwari, S.C., et al., "Macrocyclic Histone Deacetylase Inhibitors," 2010, Curr Top Med Chem, 10/14:1423-1440, 34 pages.

Nandarapu, D.R., et al., "Design and synthesis of Simplified Largazole Analogs as Isoform-Selective Human Lysine Deacetylase Inhibitors," 2015, J Med Chem, 75 pages.

Olsen, C.A., et al., "Macrocyclic Peptoid-Peptide Hybrids as Inhibitors of Class I Histone Deacetylases," 2012, ACS Med Chem Lett, 3:749-753, 5 pages.

Rajendran, P., et al., "Metabolism as a key to histone deacetylase inhibition," 2011, Crit Rev Biochem Mol Biol, 46/3:181-199, 33 pages.

Reddy, D. N., et al., "Design and Synthesis of Simplified Largazole Analogues as Isoform-Selective Human Lysine Deacetylase Inhibitors," 2016, J Med Chem, 59:1613-1633, 21 pages.

Salvador, L.A., et al., "Modulation of Activity Profiles for Largazole-Based HDAC Inhibitors through Alteration of Prodrug Properties," 2014, ACS Med Chem Lett, 5/8:905-910, Abstract Only, 2 pages.

Schnekenburger, M., et al., "Epigenetic modulators from "The Big Blue": A treasure to fight against cancer," 2014, Cancer Letters, 351/2: 182-197, Abstract Only, 3 pages.

Silvestri, L., et al., "Histone Deacetylase Inhibitors: Structure-Based Modeling and Isoform-Selectivity Prediction," 2016, J Chem Inf Model, 21 pages.

Taube, R., et al., "Lost in Transcription: Molecular Mechanisms that Control HIV Latency," 2013, Viruses, 5:902-927.

Valente, S., et al., "Small-molecule inhibitors of histone deacetylase for the treatment of cancer and non-cancer diseases: a patent review (2011-2013)," 2014, Expert Opin Ther Patents, 24/4:401-415, 15 pages.

Zhang, L., et al., "Recent Progress in the Development of Histone Deacetylase Inhibitors as Anti-Cancer Agents," 2013, Mini Reviews in Medicinal Chemistry, 15/1999-2013, Abstract Only, 2 pages.

International Search Report issued in PCT/US2016/030995, dated Sep. 29, 2016, 5 pages.

Written Opinion issued in PCT/US2016/030995, dated Sep. 29, 2016, 5 pages.

\* cited by examiner

ISOFORM-SELECTIVE LYSINE DEACETYLASE INHIBITORS

REFERENCE TO RELATED APPLICATIONS

This application is the 371 National Stage Application based on International Application Serial No. PCT/US2016/030995, filed May 5, 2016, and claims the benefit of U.S. Provisional Application Ser. No. 62/156,986, filed May 5, 2015, the contents of which are incorporated by reference herein.

GOVERNMENT LICENSE RIGHTS

This invention was made with Government support under AI102777-01 and GM106974 awarded by the National Institutes of Health. The Government has certain rights in the invention.

FIELD OF THE INVENTION

The present invention generally relates to compounds that function as isoform-selective lysine deacetylase inhibitors. In particular, various aspects of the present invention relate to cyclic tetrapeptides that are useful for treating cancer, addiction, asthma, cardiovascular disease, immunosuppression, neurodegenerative diseases, sepsis, sickle-cell disease and viral latency, particularly HIV-1 latency. The present invention also relates to various methods of using largazole and largazole analogs, particularly for treating HIV-1 latency and uveal melanoma.

BACKGROUND OF THE INVENTION

Lysine deacetylases (KDACs), more generally referred to as histone deactylases (HDACs), are a class of enzymes found in bacteria, fungi, plants and animals that catalyze the hydrolysis of acetylated lysine side chains in histone and non-histone proteins. These enzymes are implicated in a number of biological processes such as cell differentiation, proliferation, senescence, and apoptosis. Eighteen KDACs have been identified in the human genome. Eleven human KDACs are zinc-dependent enzymes; an additional seven KDACS use NAD as a cofactor. Zinc-dependent KDACs fall into three main classes, including class I (KDACs 1, 2, 3, and 8), class II, further subdivided into class IIa (KDACs 4, 5, 7, and 9) and class IIb (HDAC 6 and 10), and class IV (KDAC 11).

Aberrant KDAC activity is found in various disease states, most notably cancer, making these enzymes attractive targets for therapeutic intervention. The role of KDACs as epigenetic regulatory proteins has recently been reviewed (Falkenberg, Nat Rev Drug Discovery, 2014, 13: 673-691). To date, three KDAC inhibitors have been approved by the FDA for the treatment of cancer. These include vorinostat (Zolinza; Merck), approved for the treatment of cutaneous T cell lymphoma (CTCL), romidepsin (Istodax; Celgene), approved for the treatment of CTCL and peripheral T cell lymphoma (PTCL), and belinostat (Beleodaq; Spectrum Pharmaceuticals), approved for the treatment of PTCL.

To date, a number of small inhibitors of the zinc-dependent KDACs have been identified, including both natural products and synthetic compounds. These compounds have varying target specificity, pharmacokinetic properties and activity in laboratory and clinical settings. The most commonly used KDAC inhibitors target multiple KDACs, which makes it difficult to determine whether the biological consequences of KDAC inhibition, including clinical toxicities, are due to inhibition of a specific KDAC, the combined effect of inhibiting multiple KDACs and/or effects on one or more multiprotein complexes that incorporate specific KDACs as key enzymatic components In general, the pharmacophore of KDAC inhibitors is composed of three regions: a "capping group", which occludes the entrance of the active site pocket; a "zinc-binding group" (ZBG), which chelates the zinc ion in the active site and is required for catalytic function; and a "linker" which connects the capping group to the ZBG. The three core elements of the pharmacophore model are shown for KDAC inhibitor vorinostat below. Most KDAC inhibitors chelate the active site Zn using the hydroxamate moiety as a ZBG.

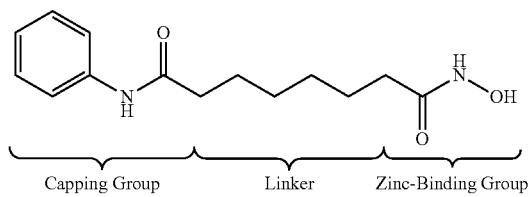 [SMILES: O=C(CCCCCCC(=O)Nc1ccccc1)NO]

The most structurally complex capping groups are found in macrocyclic peptide and depsipeptide inhibitors (a depsipeptide inhibitor contains both amide and ester linkages). For example, largazole is a 16-membered ring macrocyclic depsipeptide isolated from the marine cyanobacterium *Symploca* sp. This natural product is a potent and class-1 selective KDAC inhibitor, with substantial potency against KDAC1, KDAC2, and KDAC3 in the picomolar range. It has been established that largazole acts as a prodrug, liberating the bioactive species largazole thiol, as shown below (Bowers, JACS, 2008, 130(33): 11219-22).

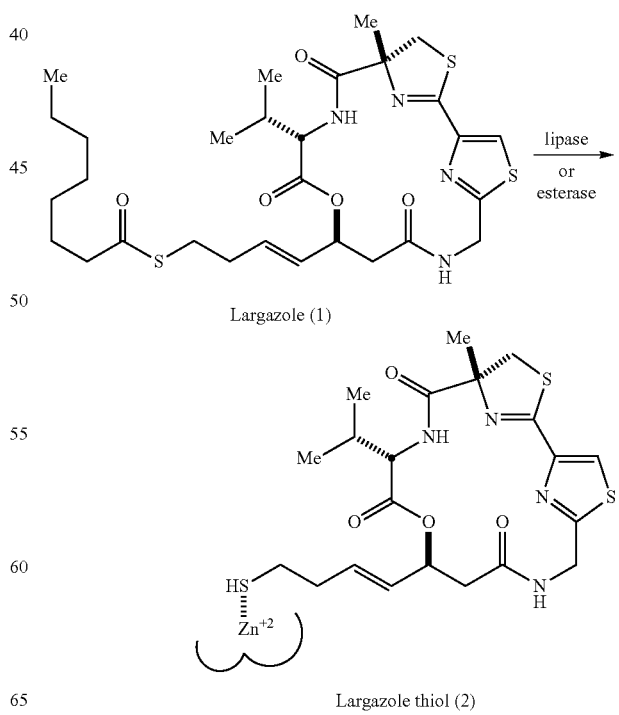

The modulation of pharmacokinetic and pharmacodynamic activity profiles of largazole-based KDAC inhibitors by employing different prodrug strategies to disguise the warhead has been reported. Others have attempted to improve specificity by varying the thiazole-thiazoline moiety in the capping group. In addition, Bowers et al. investigated the selectivity of fourteen peptide isosters analogs of largazole (Bowers, Org, Lett, 2009, 11(6): 1301-1304).

Currently, there are relatively few isoform-selective KDAC inhibitors available. Thus, there remains a need for structurally diverse KDAC inhibitors, particularly ones that are potent and/or selective inhibitors of KDAC classes and individual isoforms.

SUMMARY OF THE INVENTION

Various aspects of the present invention are directed to compounds of Formula I:

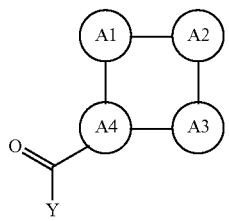

(I)

wherein A1 and A2 are each independently L-Pro, D-Pro, L-NMe-amino acid (L-NMe-AA) or D-NMe-amino acid (D-NMe-AA) wherein the N-Me-AA is derived from a naturally occurring L-amino acid or the D-stereoisomer thereof; A3 is a natural or unnatural alpha-amino acid; A4 is L- or D-aspartic acid wherein the α-carboxyl group is unprotected (Y=OH) or wherein the α-carboxyl group has been converted to an ester or amide derivative.

Further aspects of the present invention are directed to compounds of Formulas IIa, IIb, IIc, and IId or a pharmaceutically acceptable salt, solvate, prodrug, or stereoisomer thereof:

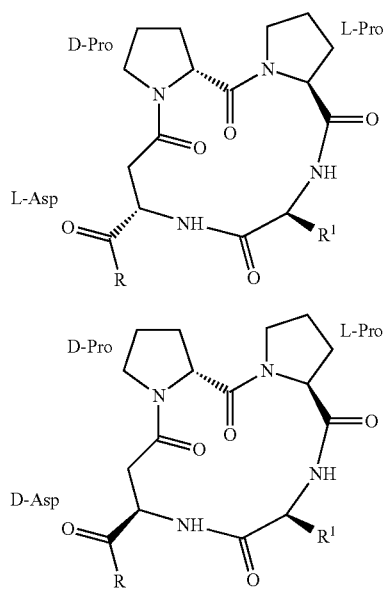

(IIa)

(IIb)

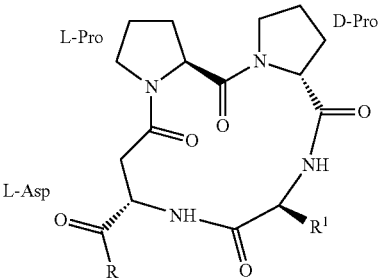

(IIc)

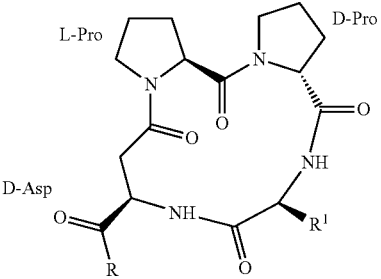

(IId)

wherein R is hydroxyl, substituted or unsubstituted alkoxy, substituted or unsubstituted aryloxy, substituted or unsubstituted arylalkyloxy, or substituted or unsubstituted amino; and $R^1$ is a naturally occurring L-amino acid.

Other aspects or the present invention are directed to pharmaceuticals composition comprising a therapeutically effective amount of one or more these compounds and/or radiolabeled analogs of these compounds.

Aspects of the present invention also include various methods of inhibiting lysine deacetylase activity in a subject in need thereof comprising administering to the subject a pharmaceutical composition comprising one or more of the compounds noted above. For example, various methods include treating a condition or disease associated with increased lysine deactylase activity in a subject in need thereof comprising administering to the subject a pharmaceutical composition comprising one or more of the compounds noted above.

Further, aspects of the present invention include methods for treating HIV latency in a subject in need thereof, comprising administering to the subject a pharmaceutical composition comprising a therapeutically effective amount of largazole, largazole thiol, a largazole analog, or combination thereof.

Also, aspects of the present invention include methods for treating uveal melanoma in a subject in need thereof, comprising administering to the subject a pharmaceutical composition comprising a therapeutically effective amount of largazole, largazole thiol, a largazole analog, or combination thereof.

Other objects and features will be in part apparent and in part pointed out hereinafter.

DESCRIPTION OF THE PREFERRED EMBODIMENTS

Figure 1A:
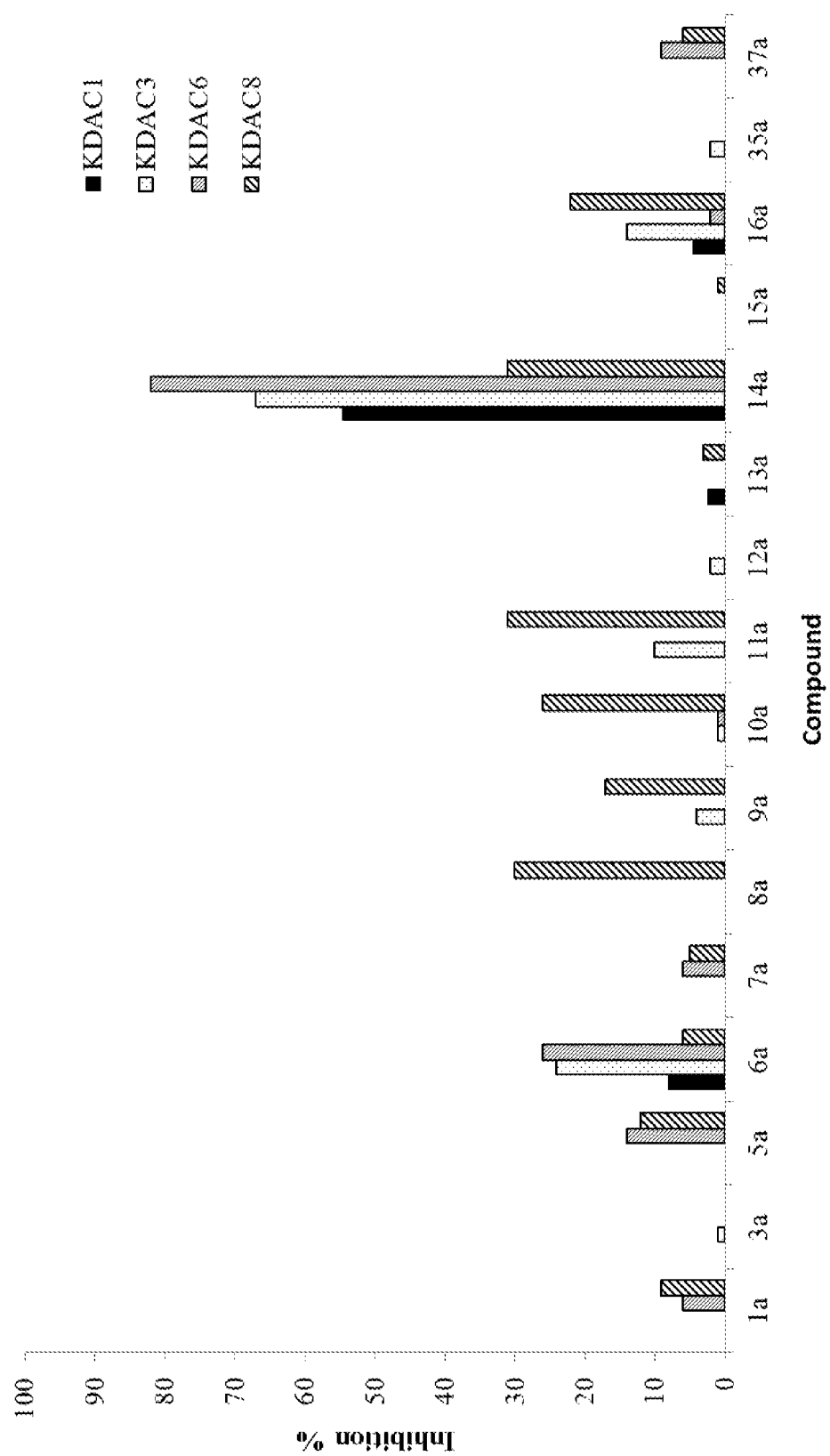
FIG. 1A: Graph of KDAC inhibition activity ($pIC_{50}$) of largazole analogs of Formula IIa.
Figure 1B:
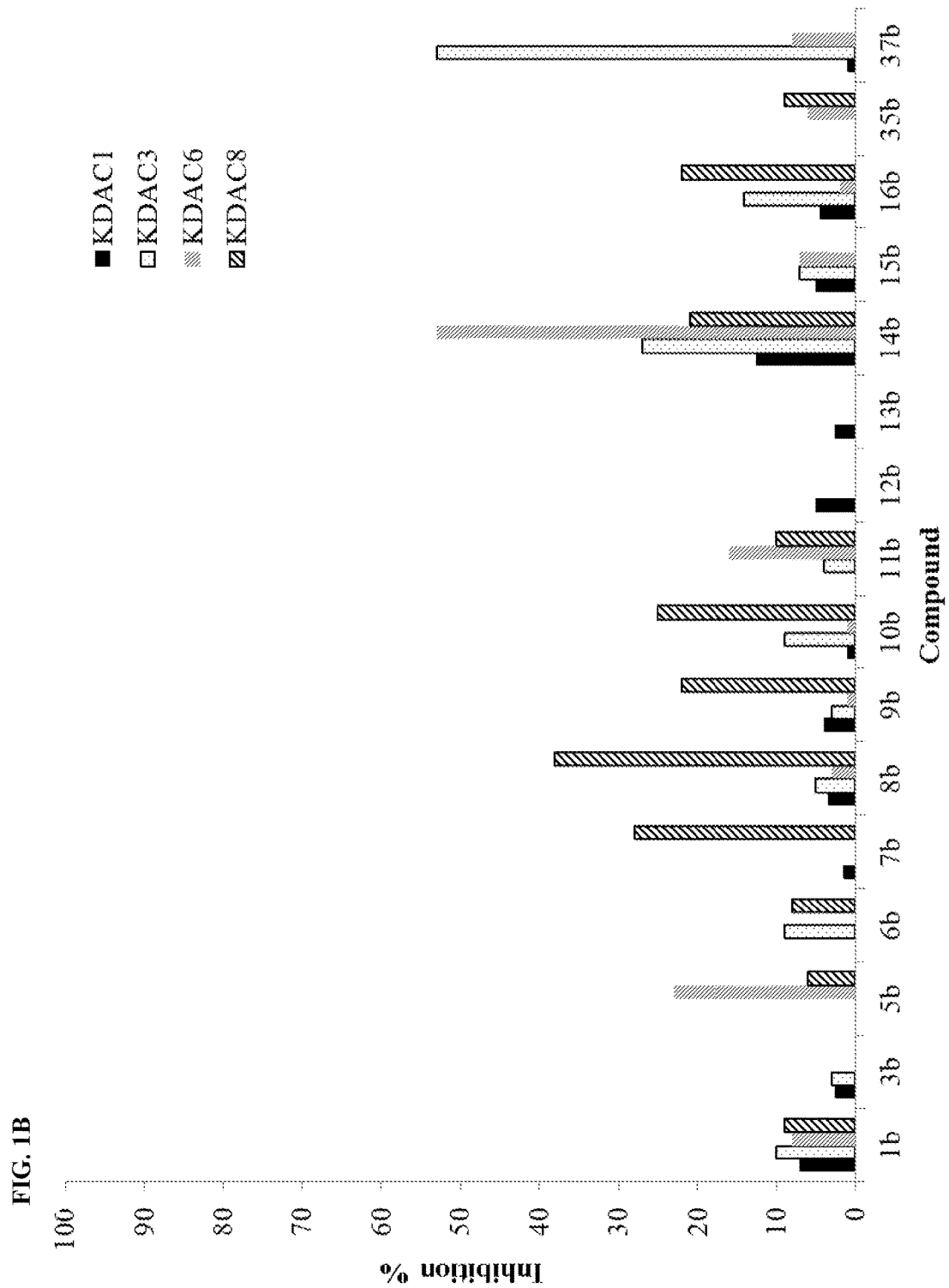
FIG. 1B: Graph of KDAC inhibition activity ($pIC_{50}$) of largazole analogs of Formula IIb.
Figure 1C:
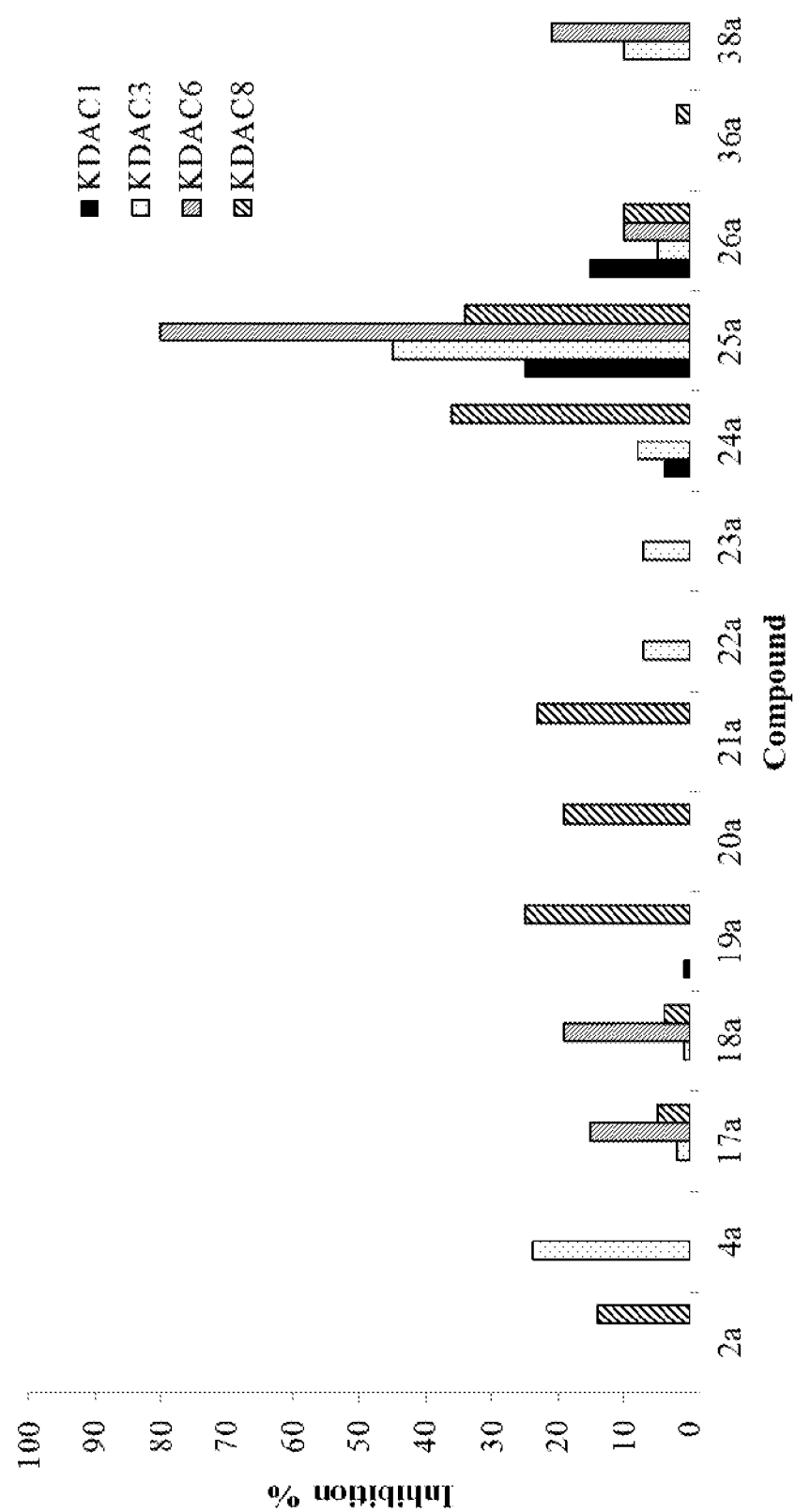
FIG. 1C: Graph of KDAC inhibition activity ($pIC_{50}$) of largazole analogs of Formula IIc.
Figure 1D:
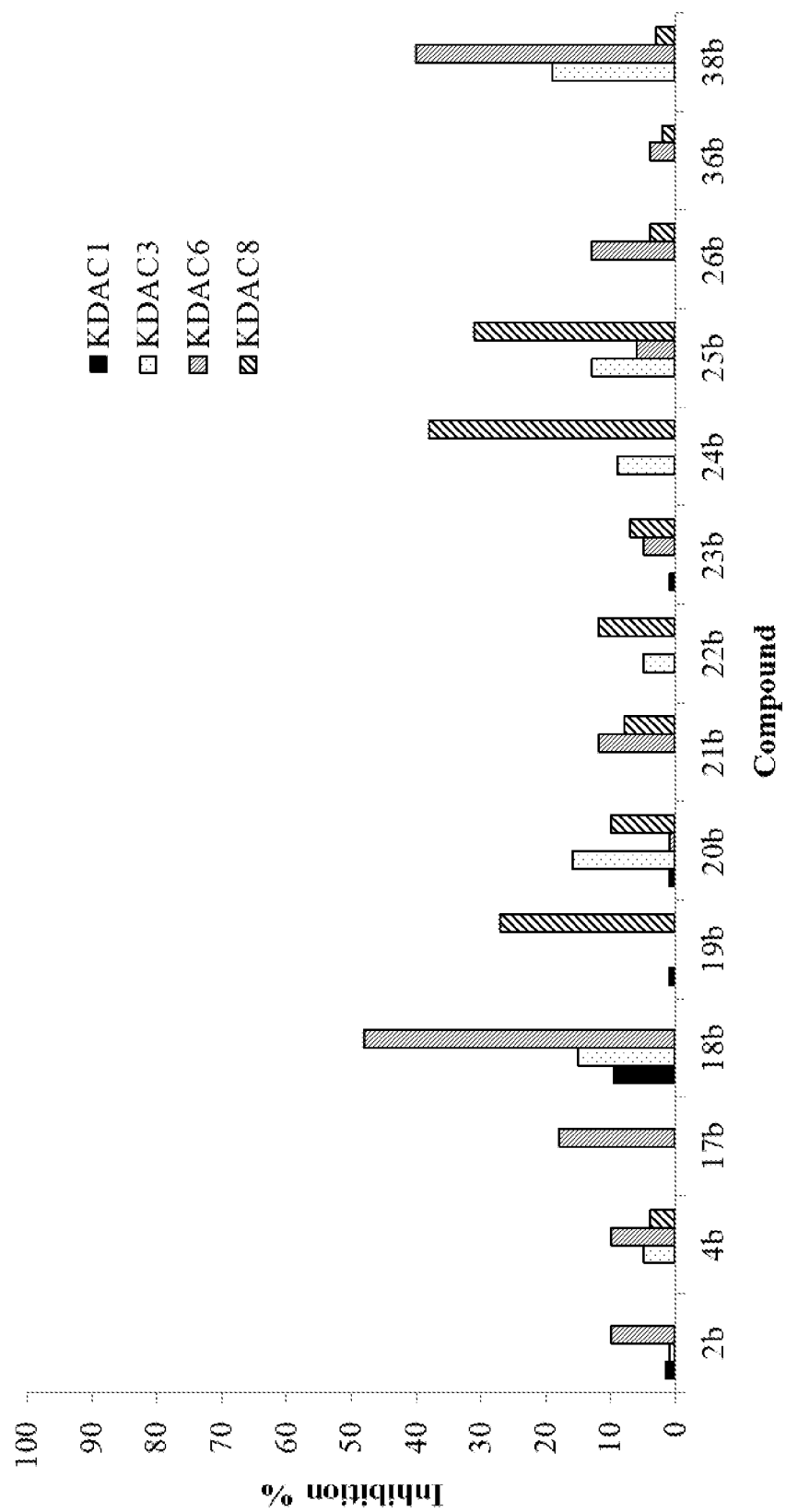
FIG. 1D: Graph of KDAC inhibition activity (pIC$_{50}$) of largazole analogs of Formula IId.

Generally, the present invention is directed to compounds that inhibit KDACs. Without being bound by theory, it is believed that misregulated KDAC activity is linked with various oncologic and non-oncologic diseases. Accordingly, the present invention also relates to various methods of using the KDAC inhibitor compounds for treating cancers such as cutaneous T cell lymphoma and peripheral T cell lymphoma, uveal melanoma and other conditions or diseases such as addiction, asthma, cardiovascular disease, immunosuppression, neurodegenerative diseases, sepsis, sickle-cell disease and termination of viral latency, particularly HIV-1 latency by administering a therapeutic effective amount of the inhibitor to a subject in need thereof.

Cyclic Tetrapeptides

KDAC inhibitors of the present invention include those that are based on the use of conformationally constrained cyclic tetrapeptides (CTPs) as scaffolds on which to display the side chains that complement the binding surface of KDAC isoforms. Generally, the cyclic tetrapeptides incorporate dipeptide subunits comprising heterochiral proline or N-methyl amino acid derivatives ("NMe-AA"). The N-Me-AA is derived from a naturally occurring L-amino acid or the D-stereoisomer thereof. Combination of alternating D- and L-prolines and/or D- and L-NMe-AA in CTPs can serve as reverse-turn mimetics, thus facilitating interaction with the binding sites of lysine deacetylases. The CTP may include dipeptide combinations such as, for example, L-Pro-D-Pro, D-Pro-L-Pro, L-Pro-D-NMe-AA, L-NMe-AA-D-Pro, D-Pro-L-NMe-AA, D-NMe-AA-L-Pro, D-NMe-AA-L-NMe-AA or L-NMe-AA-D-NMe-AA.

KDAC inhibitors of the present invention are generally compounds of Formula I:

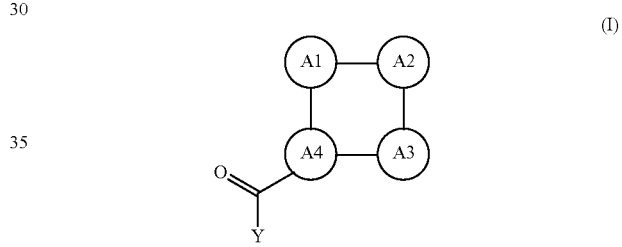

(I)

wherein A1 and A2 are each independently L-Pro, D-Pro, L-NMe-AA or D-NMe-AA; A3 is a natural or unnatural alpha-amino acid; and A4 is L- or D-aspartic wherein the α-carboxyl group is unprotected (Y=OH) or wherein the α-carboxyl group has been converted to an ester or amide derivative.

Preferably, the KDAC inhibitors of the present invention include compounds of Formula IIa, IIb, IIc, and/or IId or a pharmaceutically acceptable salt, solvate, prodrug, or stereoisomer thereof, having a diproline subunit at A1-A2, a naturally occurring L-amino acid at A3, and L- or D-aspartic acid (or ester or amide derivative thereof) at A4 as shown below:

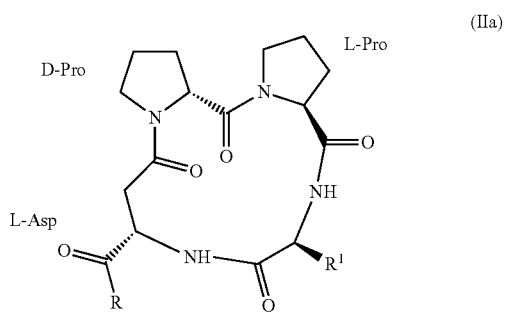

(IIa)

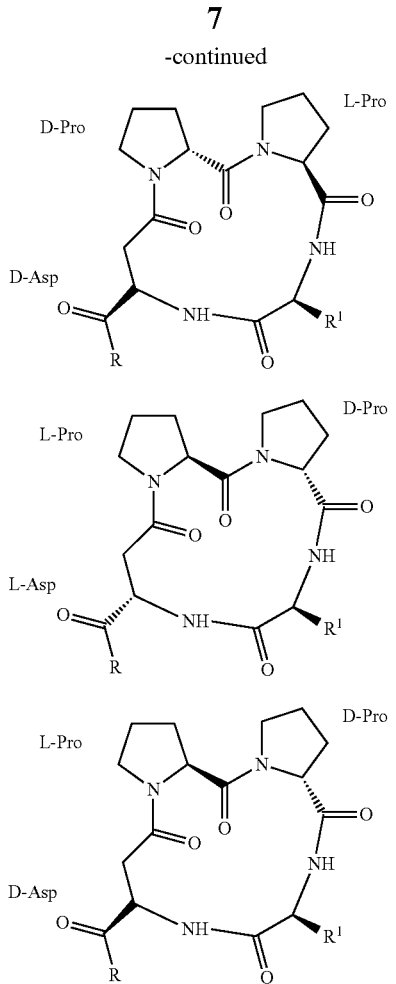

wherein R is hydroxyl, substituted or unsubstituted alkoxy, substituted or unsubstituted aryloxy, substituted or unsubstituted arylalkyloxy, or substituted or unsubstituted amino; and $R^1$ is a naturally occurring L-amino acid.

Compounds IIa, IIb, IIc, and IId are cyclic tetrapeptides having a 13-membered ring derived from three alpha-amino acids and one beta-amino acid (i.e., α3β architecture). Compounds of Formula IIa and IIb have the dipeptide subunit D-Pro-L-Pro, whereas compounds of Formula IIc and IId have the dipeptide subunit L-Pro-D-Pro. The third amino acid is a naturally occurring L-amino acid, and the fourth amino acid is a β-amino acid which is L-Asp (compounds IIa and IIc) or D-Asp (compounds IIb and IId).

The $R^1$ group derives from the third amino acid. In various embodiments, $R^1$ is H (Gly), Me (Ala), isopropyl (Val), isobutyl (Leu), or sec-butyl (Ile). Side chains from other natural amino acids are also included. In preferred embodiments, $R^1$ is isopropyl (Val).

The cyclic tetrapeptide also has a side chain that is a carboxyl group, corresponding to the α-carboxyl group of L- or D-aspartic acid, or a derivative thereof. The carboxyl group can be converted, for example, into an ester. Accordingly, R can be hydroxy, substituted or unsubstituted alkoxy, substituted or unsubstituted aryloxy, or substituted or unsubstituted arylalkyloxy. In various embodiments, R is hydroxy, substituted or unsubstituted $C_1$-$C_6$ alkoxy, substituted or unsubstituted phenoxy, or substituted or unsubstituted benzyloxy. In certain embodiments, R is hydroxy or benzyloxy.

The carboxyl group can also be converted into an amide. Accordingly, R can be amino ($NH_2$) or substituted amino. In various embodiments, R is substituted amino having the formula $-NH-(CH)_nR^2$, where $R^2$ is OH, $SR^3$, $SOR^3$, $SO_2R^3$, $NR^3$, $CO_2R^3$, $C(O)NHOR^3$, $S-S(CH_2)_nNH_2$, $-NH(CH_2)_nS-S(CH_2)_nNHPO(OR^4)_2$; $R^3$ is hydrogen or $C_1$-$C_6$ alkyl (e.g., methyl or ethyl); $R^4$ is hydrogen or phenyl; and n is a number from 2 to 5 (e.g., n can be 2 to 3).

Methods of Using KDAC Inhibitors

The present invention is further directed to various methods of using the compounds described herein. In general, the methods of the present invention involve inhibiting lysine deacetylase in a subject in need thereof comprising administering to the subject a pharmaceutical composition comprising a compound of Formulas I, IIa-IId or combination thereof. In particular, various methods of the present invention include methods of treating a condition or disease associated with increased lysine deactylase activity in a subject in need thereof comprising administering to the subject a pharmaceutical composition comprising a compound of Formulas I, IIa-IId or combination thereof.

In various methods of the present invention, the disease or condition comprises cancer. For example, the cancer can be selected from the group consisting of a carcinoma, an adenoma, a melanoma, a sarcoma, a lymphoma, a myeloid leukemia, a lymphatic leukemia, a blastoma, a glioma, an astrocytoma, a mesothelioma, or a germ cell tumor. The cancer can be selected from the group consisting of ovarian cancer, renal cancer, colon cancer, melanoma, brain/central nervous system cancer, and breast cancer. In various embodiments, the cancer is uveal melanoma. Also, the cancer can be selected from the group consisting of cutaneous T cell lymphoma and peripheral T cell lymphoma. These methods can also include administering a therapeutically effective amount of an additional anti-cancer agent.

In various methods of the present invention, the disease or condition is selected from the group consisting of addiction, asthma, cardiovascular disease, immunosuppression, neurodegenerative diseases, sepsis, sickle-cell disease and termination of viral latency. In certain embodiments, the disease or condition comprises HIV-1 latency. In these embodiments, the method can further comprise administering antiviral agents, such as those currently used in highly active antiretroviral therapy (HAART).

In various aspects of the present invention, the KDAC inhibitor is selective for inhibiting the lysine deacetylating activity of at least one isoform selected from the group consisting of KDAC1, KDAC2, KDAC3, KDAC4, KDAC5, KDAC6, KDAC7, KDAC8, KDAC9, KDAC10, KDAC11, and a combination thereof. For example, the KDAC inhibitor can be selective for inhibiting the lysine deacetylating activity of at least one KDAC isoform with an inhibition activity ($IC_{50}$) from about 1 to about 10,000 picomolar. In various embodiments, the KDAC inhibitor is selective toward at least one of KDAC1, KDAC2, KDAC3, and KDAC8.

Methods for Treating HIV Latency and Uveal Melanoma

Another aspect of the invention provides methods for treating HIV latency in a subject in need thereof, comprising administering to the subject a pharmaceutical composition comprising a therapeutically effective amount of largazole, largazole thiol, a largazole analog, or combination thereof. Still another aspect of the invention provides methods for treating uveal melanoma in a subject in need thereof, comprising administering to the subject a pharmaceutical composition comprising a therapeutically effective amount of largazole, largazole thiol, a largazole analog, or combination thereof.

The structures of largazole and largazole thiol are shown below:

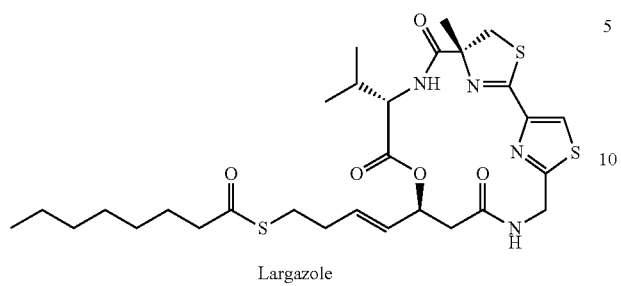
Largazole

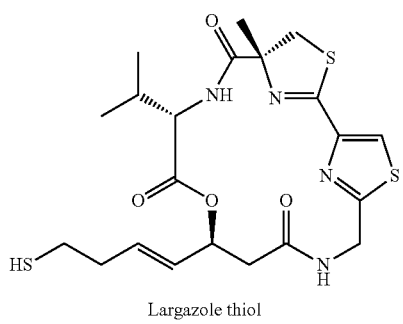
Largazole thiol

Examples of largazole analogs include, for example, peptide isosters, analogs with an oxazole-oxazoline moiety, analogs with a dithiazole moiety, analogs with a saturated side chain, analogs with a longer side chain, analogs having a valine to proline substitution, and analogs having a thiazole to pyridine substitution. Various largazole analogs are described in U.S. Pat. No. 8,217,076, the contents of which are hereby incorporated by reference. Accordingly, in various embodiments, the largazole analog comprises a compound of Formula Ma or a disulfide dimer of Formula IIIb:

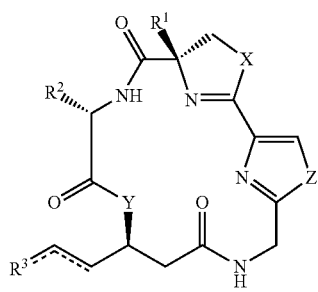
Formula IIIa

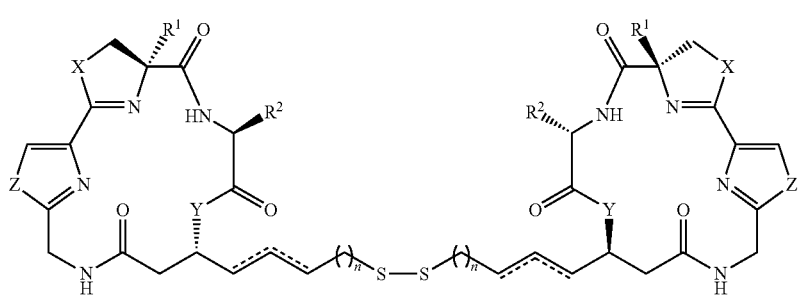
Formula IIIb wherein X and Z are each independently S or O;
Y is NR or O;
R is H, lower alkyl, or lower arylalkyl;
$R^1$ is H, lower alkyl or lower arylalkyl;
$R^2$ is lower alkyl, isopropyl, n-propyl, cyclopropyl, isobutyl, n-butyl, sec-butyl, or tert-butyl;
$R^3$ is H, $(CH_2)_nCO_2H$, $(CH_2)_nCONHR$, $(CH_2)_nCONHOH$, $(CH_2)_nSR^4$, $SR^5$, $(CH_2)_nNHC(O)CH_2SR$ or

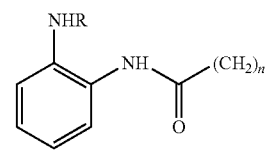

$R^4$ is H, acyl, octanoyl, a higher acyl derivative, or SR;
$R^5$ is lower alkyl or lower aryl; and
n is at least 1 (e.g., 1, 2, 3, 4 or 5); or a pharmaceutically acceptable salt, solvate, clathrate, prodrug, or stereoisomer thereof.

In certain embodiments, the largazole analog comprises a compound of Formula IIIa that is selected from the group consisting of:

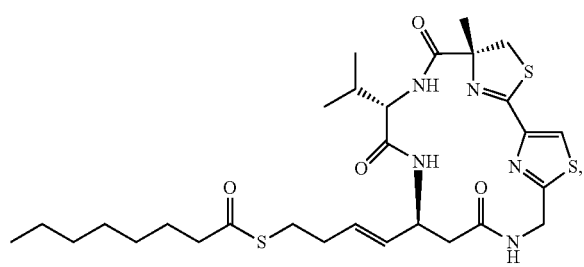
Formula IIIa

-continued
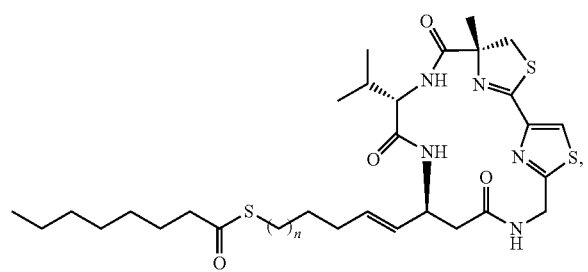
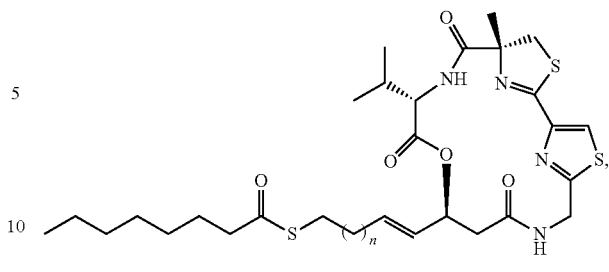
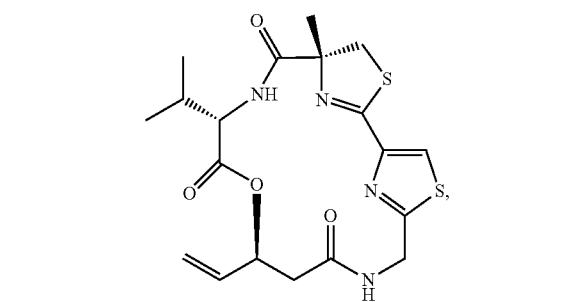
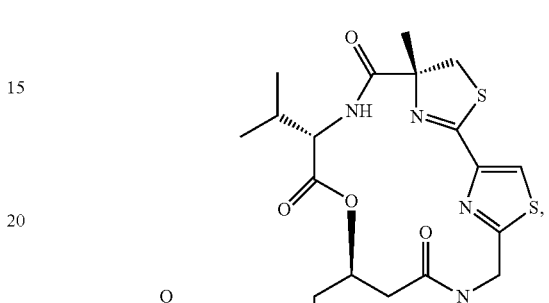
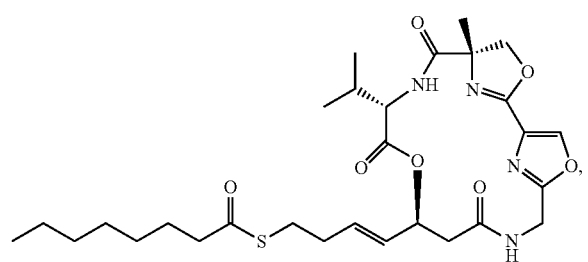
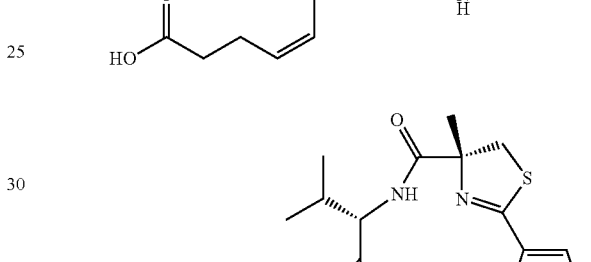
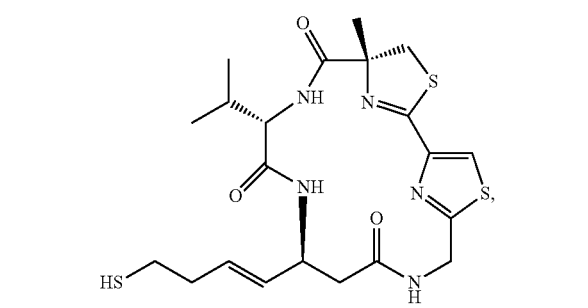
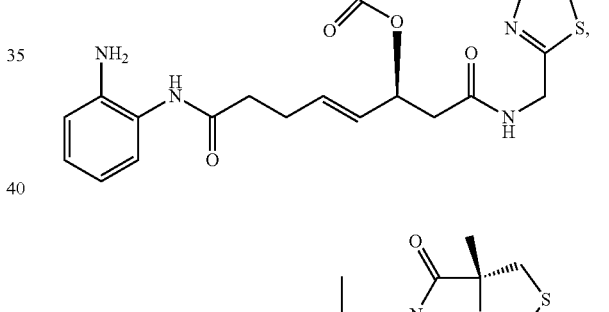
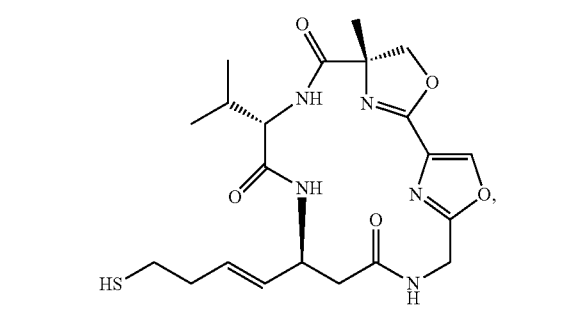
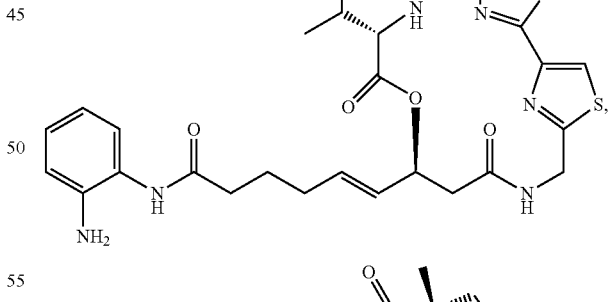
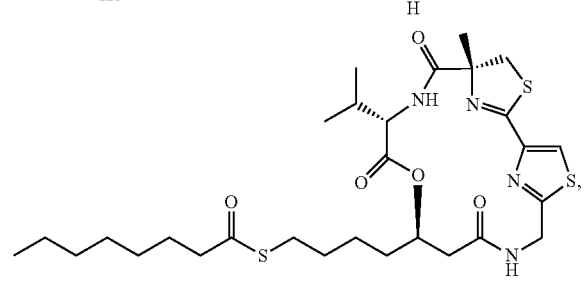
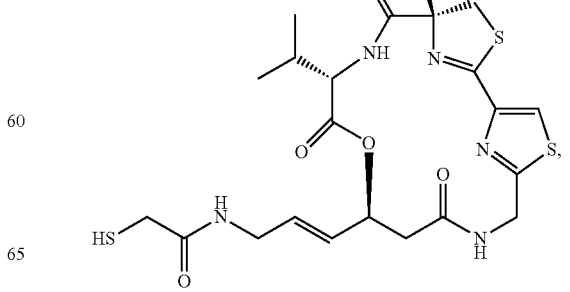

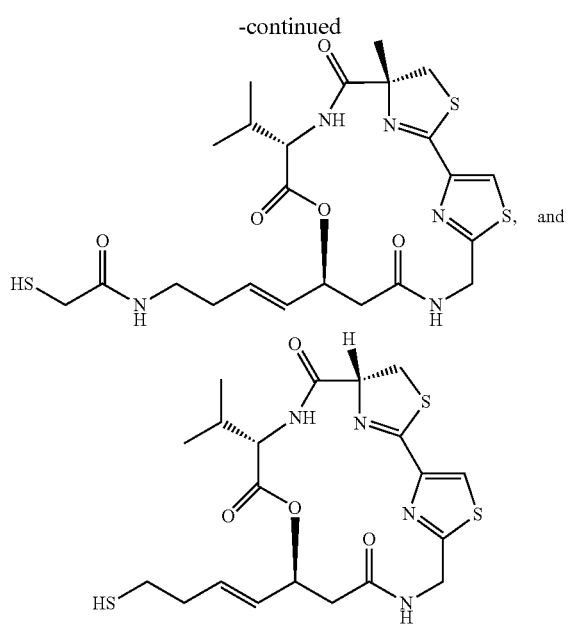

wherein n is at least 1 (e.g., 1, 2, 3, or 4).

In various embodiments, the largazole analog comprises a compound of Formula IVa or a disulfide dimer of Formula IVb, wherein the substituents are defined as above for compounds of Formula IIIa and IIIb.

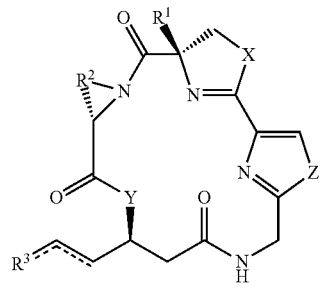

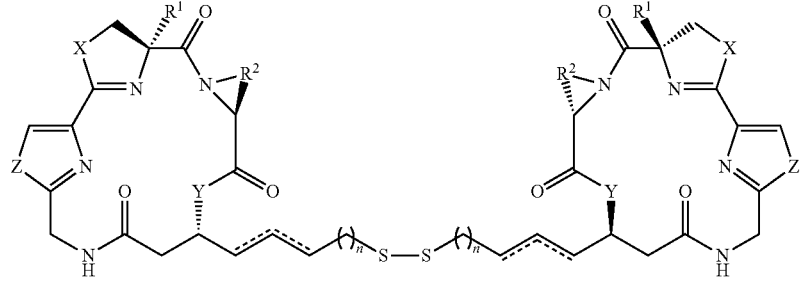

An exemplary compound of Formula IVa has the structure shown below.

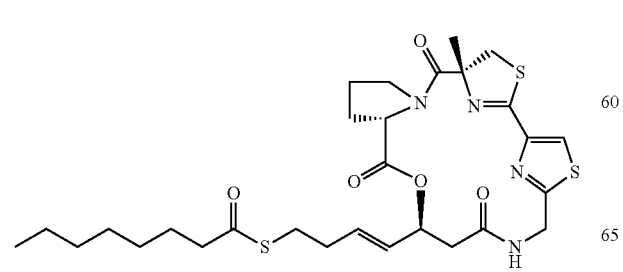

In certain embodiments, the largazole analog comprises a compound of Formula Va or a disulfide dimer of Formula Vb wherein the substituents are defined as above for compounds of Formula IIIa and IIIb.

Formula Va

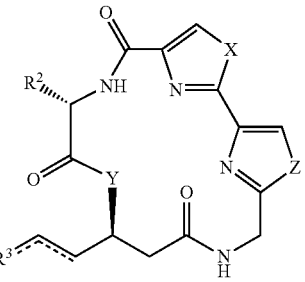

Formula Vb

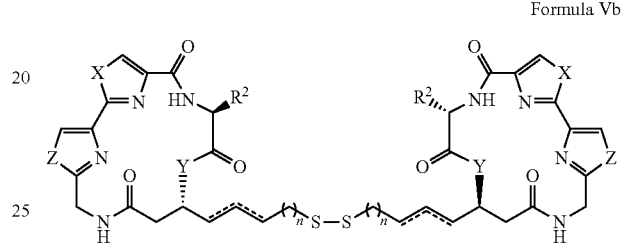

An exemplary compound of Formula Va has the structure shown below.

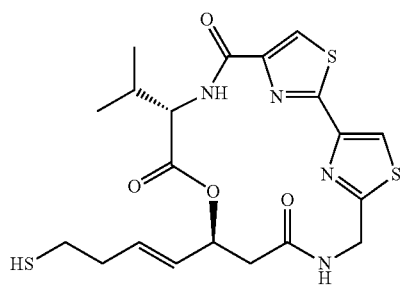 [SMILES: CC(C)[C@@H]1NC(=O)c2csc(n2)-c2csc(n2)CNC(=O)C[C@@H](/C=C/CCS)OC1=O]

In various embodiments, the largazole analog comprises a compound of Formula VIa or a disulfide dimer of Formula VIb:

Formula VIa

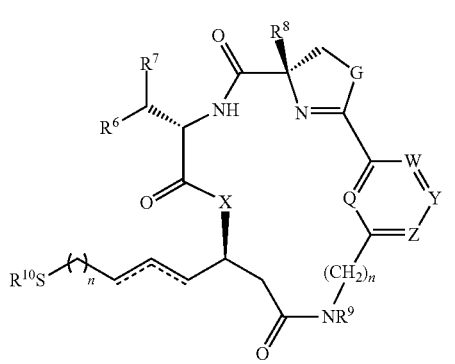

Formula VIb

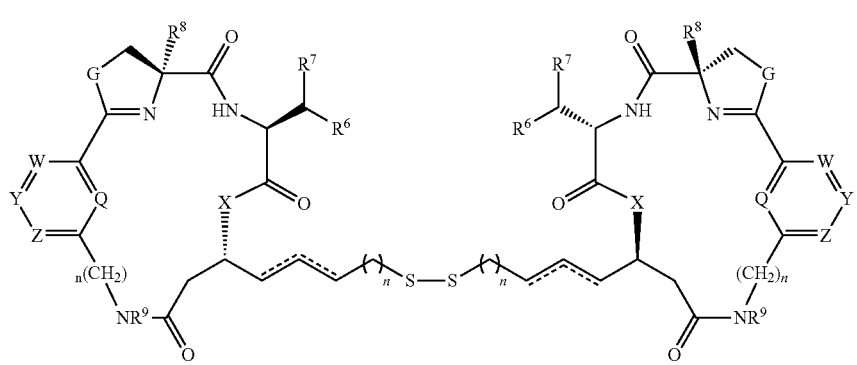

wherein X is O or $NR^{12}$;
G is S, O, or $NR^{12}$;
Q, W, Y, and Z are independently, N or CH, wherein at least one of Q, Y, Y, and Z is CH;
$R^6$ is and $R^7$ are each independently H or lower alkyl;
$R^8$ is H, lower alkyl, or lower arylalkyl;
$R^9$ is H or lower alkyl;
$R^{10}$ is octanoyl, $C(O)R^{11}$;
$R^{11}$ is lower alkyl, lower aryl, or lower arylalkyl;
$R^{12}$ is H, lower alkyl, or lower arylalkyl; and
n is 0, 1, 2, or 3
or a pharmaceutically acceptable salt, solvate, clathrate, prodrug, or stereoisomer thereof.

Exemplary compounds of Formula VIa include those having the following structures:

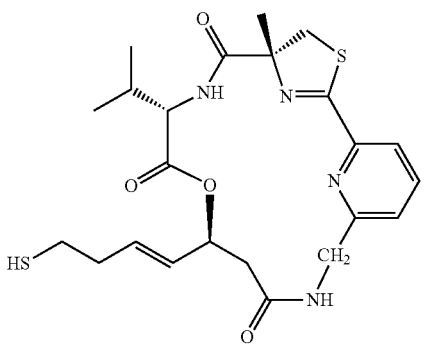

-continued

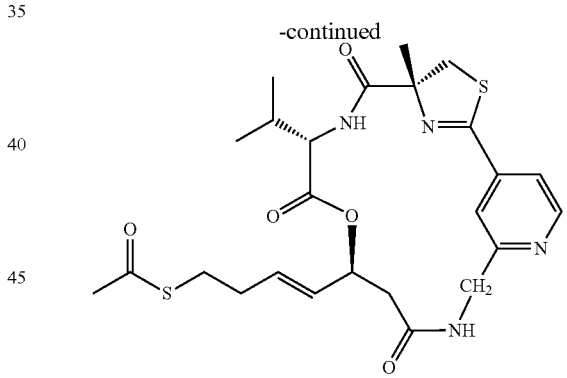

In the compounds of Formula III, IV, V, and VI, the designation of one line parallel to a dotted line represents an optional double bond. That is, the bond can be a single bond or a double bond. When a double bond is present, the alkene may have either a cis- or trans-configuration As used herein, "lower alkyl" or "lower alkyl moieties" contain from 1-12 carbon atoms, "lower aryl" or "lower aryl moieties" contain from 6-12 carbon atoms, and "lower arylalkyl" or "lower arylalkyl moieties" contain from 7-12 carbon atoms. In a preferred embodiment, lower alkyl refers to a $C_{1-7}$ alkyl, lower aryl refers to a $C_{6-10}$ aryl, and lower arylalkyl refers to a $C_{7-11}$ aralkyl. Included are substituted derivatives of lower chain alkyl, aryl and arylalkyl moieties, wherein the substituent is selected from (but are not limited to) one or more of the following chemical moieties: —OH, —OR, —COOH, —COOR, —CONH$_2$, —NH$_2$, —NHR, —NRR, —SH, —SR, —SO$_2$R, —SOR, —PO$_3$R, —OPO$_3$R, and halogen (including F, Cl, Br and I), wherein each occurrence of R is independently selected from a lower chain alkyl, aryl or arylalkyl moiety. Moreover, cyclic lower chain alkyl, aryl and arylalkyl moieties of the invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 J. Pharm. Sci. 66:1-19). Prodrugs can typically be prepared using well-known methods, such as those described in Burger's Medicinal Chemistry and Drug Discovery (1995, Manfred E. Wolff ed., 5th ed. 172-178, 931-932).

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Furthermore, some of the crystalline forms of the compounds of Formulas III to VI may exist as polymorphs, which are included in the present invention. In addition, some of the compounds of Formulas III to VI may also form solvates with water or other organic solvents. Such solvates are similarly included within the scope of this invention.

The present invention also includes pharmaceutical compositions where the KDAC inhibitor (i.e., a compound of Formulas IIa, IIb, IIc, IId, IIIa, IIIb, IVa, IVb, Va, Vb, VIa, VIb, or combination thereof) is radiolabeled. Radiolabeled compounds are useful for various diagnostic techniques.

In accordance with other aspects of the present invention, the compounds of the present invention can be formulated in a suitable pharmaceutical composition. Generally, the pharmaceutical composition comprises a therapeutically effective amount of at least one KDAC inhibitor (i.e., a compound of Formulas IIa, IIb, IIc, IId, IIIa, IIIb, IVa, IVb, Va, Vb, VIa, VIb, or combination thereof) and one or more excipients.

Pharmaceutical compositions containing the compounds of the present invention can be formulated in any conventional manner. Proper formulation is dependent in part upon the route of administration selected. Routes of administration include, but are not limited to, oral, parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable excipients for use in the compositions of the present invention are selected based upon a number of factors including the particular compound used, and its concentration, stability and intended bioavailability; the disease, disorder or condition being treated with the composition; the subject, its age, size and general condition; and the route of administration.

The pharmaceutical compositions can be formulated, for example, for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. Pharmaceutical compositions for oral administration can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

In another aspect, the pharmaceutical compositions can be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Pharmaceutically acceptable excipients are identified, for example, in *The Handbook of Pharmaceutical Excipients*, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

As described herein, the abbreviations of the naturally occurring amino acids are as follows:

| Amino acid | Three letter code | One letter code |
| --- | --- | --- |
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

As used herein, the term "effective amounts" of a therapeutic agent can be determined in many different ways, such as assaying for a reduction in tumor size or improvement of physiological condition of a subject. Effective amounts also can be determined through various in vitro, in vivo or in situ assays.

"Pharmaceutically acceptable salt" as used herein refers to salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate, and aryl sulfonate.

"Subject" as used herein refers to a mammal, including both human and non-human mammals. Subjects include veterinary subjects, including livestock such as cows and sheep, rodents (such as mice and rats), and non-human primates. Preferred subjects are human subjects.

"Treat", "treating", and "treatment" refer to a method of alleviating or abating a disease and/or its attendant symptoms.

As used herein, the following abbreviations and definitions are: "CTP" refers to cyclic tetrapeptide; "DPPA" refers to diphenylphosphoryl azide; "FITC" refers to fluoresceine isothiocyanate; "HAART" refers to highly active antiretroviral therapy; "KDAC" refers to lysine deacetylase; "OtBu" refers to ortho-tert-butyl; "EDC" refers to 1-ethyl-3-(3-(dimethylamino)-propyl)carbodiimide; "SAHA" refers to suberoylanilide hydroxamic acid; "SLA" refers to simplified largazole analogue; and "TSA" refers to trichostatin A.

Having described the invention in detail, it will be apparent that modifications and variations are possible without departing from the scope of the invention defined in the appended claims.

EXAMPLES

The following non-limiting examples are provided to further illustrate the present invention.

Example 1. Materials and Methods

All the reactions were performed in oven-dried apparatus and were stirred using magnetic stir bars. Starting materials, reagents, and solvents were purchased from commercial vendors unless otherwise noted. Chromatography grade ethylacetate, dichloromethane, acetonitrile, and hexanes were obtained from Sigma-Aldrich. Column chromatography was performed on silica gel (100-200 mess) purchased from Sorbent Technologies. Thin layer chromatography (TLC) was carried out on ANALTECH 200 microns silica-gel coated plastic-fiber sheets. All reactions were monitored by TLC carried out on Merck silica-gel plates (0.25 mm thick, 60F254), visualized by using UV (254 nm) or dyes such as ninhydrin, KMnO4, p-anisaldehyde or CAM (ceric ammonium molybdate). High-performance liquid chromatography (HPLC) was carried out on GILSON GX-281 using Waters C18 5 µM, 4.6*50 mm and Waters Prep C18 5 µM, 19*150 mm reverse phase columns. The mobile phases used were A: $H_2O$ with 0.05% TFA, B: $CH_3CN$ with 0.05% TFA using a solvent gradient of A-B over 30 minutes with a flow rate of 14.8 mL/min, with detection at 220 and 254 nm UV detectors. Purity assessment and mass spectra (MS) data were obtained using a Hewlett-Packard HPLC/MSD using electrospray ionization (ESI) for detection. $^1H$ and $^{13}C$ NMR spectra were measured on a Varian 400 MHz NMR instrument. Chemical shifts are expressed in parts per million (ppm) from the residual of nondeuterated solvents as internal standard. ($^1H$ NMR: TMS $\delta$=0.00 ppm, $CDCl_3$ $\delta$=7.26 ppm, DMSO-$d_6$ $\delta$=2.50 ppm, $D_2O$: 4.79 ppm; $^{13}C$ NMR (APT): TMS $\delta$=0.00 ppm, $CDCl_3$ $\delta$=77.16 ppm, DMSO-$d_6$ $\delta$=39.52 ppm). Coupling constants (J) are given in hertz (Hz). The following abbreviations were used to express the multiplicities: s=singlet; d=doublet; t=triplet; q=quartet; p=pentet; quin=quintet; sep=septet; hept=heptet; m=multiplet; dd=doublet of doublets; dt=doublet of triplet; td=triplet of doublet; bs=broad singlet. All compounds used for biological assays are >95% pure based on NMR and LC-MS by UV absorbance at 210 nm and 254 nm wavelengths.

$^{1}$H and $^{13}$C NMR spectra were recorded on a Varian 400 MHz NMR instrument and processed using ACD NMR lab software.

Example 2. General Procedures for Peptide Coupling

General Procedure for Mixed Anhydride Peptide Coupling Protocol

To a cold (−20° C.) solution of the carboxylic acid (1 mmol) and N-methyl morpholine (NMM) (1.5 mmol) in tetrahydrofuran (THF) (6 mL) was added ethylchloroformate (ECF) (1.03 mmol) under $N_2$ atmosphere and vigorously stirred. After 2 minutes of stirring, a solution of amino acid methyl ester hydrochloride (1.05 mmol) in a mixture of THF:DMF (1:4—v/v) was added to the mixture followed by NMM (2.5 mmol) and stirred. After 10 minutes, the mixture was warmed to 25° C. and stirred further until TLC indicated complete consumption of the starting acid. THF was removed under reduced pressure and the resulting viscous solution was diluted with water (5 mL) and thoroughly extracted with ethyl acetate (15 mL). The combined organic extracts were washed with 1 N HCl (5 mL), saturated aqueous sodium bicarbonate ($NaHCO_3$) (5 mL) and dried over anhydrous sodium sulphate ($Na_2SO_4$) and concentrated to give a residue, which was purified by silica gel (100-200 mesh) flash column chromatograph.

General Procedure for EDCl Peptide Coupling Protocol

To a solution (0° C.) of 1-(3-dimethylaminopropyl)-3-ethylcarbodiimide hydrochloride (1.3 mmol), 1-hydroxybenzotriazole (1.3 mmol), Boc-A1-OH (1 mmol) in dichloromethane (10 mL) added N,N-diisopropylethylamine (3 mmol) was stirred for 15 minutes. Then added solution of amino acid ester hydrochloride (1 mmol) in N,N-dimethylformamide (2 mL) flask and the reaction mixture was stirred at room temperature till the starting material was consumed completely. N,N-dimethylformamide and dichloromethane were removed under reduced pressure and the resulting viscous solution was diluted with water (5 mL) and thoroughly extracted with ethyl acetate (15 mL). The combined organic extracts were washed with 1 N HCl (5 mL), saturated aqueous sodium bicarbonate ($NaHCO_3$) (5 mL) and dried over anhydrous sodium sulphate ($Na_2SO_4$) and concentrated to give a residue, which was purified by silica gel (100-200 mesh) flash column chromatograph.

General Procedure for HATU Peptide Coupling Protocol

To a solution (0° C.) of 1-[bis(dimethylamino)methylene]-1H-1,2,3-triazolo[4,5-b]pyridinium 3-oxid hexafluorophosphate (HATU) (1.3 mmol) in dichloromethane (or) N,N-dimethylformamide (10 mL) added N,N-diisopropylethylamine (3 mmol) was stirred for 15 min. Then added solution of amino acid ester hydrochloride (1 mmol) in N,N-dimethylformamide (2 mL) flask and the reaction mixture was stirred at room temperature till the starting material was consumed completely. N,N-dimethylformamide and dichloromethane were removed under reduced pressure and the resulting viscous solution was diluted with water (5 mL) and thoroughly extracted with ethyl acetate (15 mL). The combined organic extracts were washed with 1 N HCl (5 mL), saturated aqueous sodium bicarbonate ($NaHCO_3$) (5 mL) and dried over anhydrous sodium sulphate ($Na_2SO_4$) and concentrated to give a residue, which was purified by silica gel (100-200 mesh) flash column chromatograph.

General Procedure for Diphenylphosphoryl Azide (DPPA) Peptide Coupling Protocol Diisopropylethylamine (1 mmol) was added dropwise over 1 min to a stirred solution of the amino acid in dimethylformamide (8 ml) at 25° C. under an atmosphere of nitrogen. The solution was stirred at 25° C. for 15 minutes and then diphenylphosphoryl azide (DPPA) (1.5 mmol) was added dropwise over 1 minute. The mixture was stirred at 25° C. for complete consumption of starting material. N,N-dimethylformamide was removed under reduced pressure and the resulting viscous solution was diluted with water (5 mL) and thoroughly extracted with ethyl acetate (15 mL). The combined organic extracts were washed with 1 N HCl (5 mL), saturated aqueous sodium bicarbonate ($NaHCO_3$) (5 mL) and dried over anhydrous sodium sulphate ($Na_2SO_4$) and concentrated to give a residue, which was purified by silica gel (100-200 mesh) flash column chromatograph.

Example 3. General Procedures for N and C Terminal Protecting Groups and Deprotection

General Procedure for Acidic Cleavage of N-Tert-Butyloxycarbonyl (Boc) and O$^t$Butylester (O$^t$Bu) Protecting Group The protected peptide (1.0 mmol) was dissolved in 30% trifluoroacetic acid in $CH_2Cl_2$ (5 mL) and stirred at 0° C. for 3 hours. Solvent was removed by rotary evaporation and the residue washed with hexane (3×10 mL) for removal of a trace amount of trifluoroacetic acid. The residue was dried in vacuo over KOH trap and used without further purification.

General Procedure for Base-Mediated Hydrolysis of Benzyl Ester (OBn)

To a stirred solution of lithium hydroxide (1.5 mmol) in of distill water (1 mL) was added the benzylester (1 mmol) in THF (3 mL) and then stirred at room temperature for 3.5 hours, then THF was removed under reduced pressure, acidified with 1N HCl until pH comes to 2-3 at 0° C. Then extracted with EtOAc, dried over anhydrous sodium sulphate ($Na_2SO_4$) and concentrated to give the desired acid.

General Procedure for Catalytic Hydrogenation of Benzyl Ester (OBn) Protecting Group A stirred solution of the benzyl ester (1 mmol) and 10% Palladium/Carbon (0.1 mmol) in EtOH (10 mL) at 25° C. was placed under an atmosphere of hydrogen. After 4 hours, the mixture was filtered through Celite using EtOH as eluent, and concentrated under reduced pressure and proceeded further without purification.

General Procedure for LiOH Base-Mediated Hydrolysis of Methyl Ester

To a stirred solution of lithium hydroxide (1.5 mmol) in of distill water (1 mL) was added to the methyl ester (1 mmol) in MeOH (3 mL) and then stirred at room temperature for 3.5 hours, then MeOH was removed under reduced pressure, acidified with 1N HCl until pH was between 2-3 at 0° C. Then extracted with EtOAc, dried over anhydrous sodium sulphate (Na$_2$SO$_4$) and concentrated to give the desired acid, which was used further without purification.

General Procedure for Fmoc Deprotection

The Fmoc protected peptide (1.0 mmol) was dissolved in 20% piperidine in dichloromethane (5 mL) and stirred at 25° C. for 3 hours. Solvent was removed by rotary evaporation and the residue washed with hexane (3×10 mL) for removal of trace amount of piperidine. The residue was dried in vacuo over a KOH trap and used without further purification.

Example 4: General Procedure for 3-Aminopropanethiol Hydrochloride Synthesis

Scheme 1 shows the synthetic scheme for 3-aminopropanethiol.

Scheme 1: Synthesis of 3-aminopropanethiol

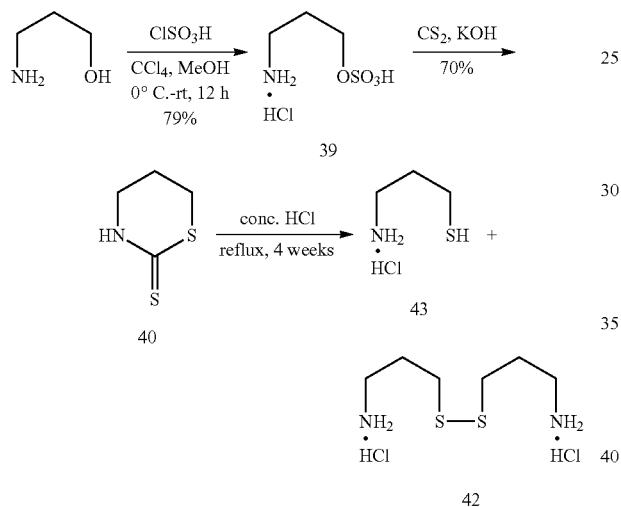

1-Amino-3-propylsulfate (39)

A mixture of 3-amino-1-propanol (5 g, 67 mmol) and carbon tetrachloride (20 mL) was cooled in an ice bath. Chlorosulfonic acid (4.43 mL, 67 mmol) was slowly added to the mixture. The reaction mixture was kept overnight, and carbon tetrachloride was removed in vacuo. The crude solid was crushed with methanol (40 mL), and isolated by filtration. A pure white powder of 1-amino-3-propylsulfate was obtained by recrystallization from water/methanol. Yield: 11.1 g, 87%. MS m/z for C$_3$H$_{10}$NO$_4$SN [M+H]$^+$ calcd 155.2, Found 155.4.

Tetrahydro-1,3-thiazine-2-thione (40)

To a suspension containing 1-amino-3-propylsulfate (10 g, 52 mmol) and carbon disulfide (3.76 mL, 62.5 mmol) in ethanol (20 mL) was added slowly in an ice bath, NaOH (4.6 g, 115 mmol) in water (20 mL). After the reaction mixture was heated to reflux at 75° C. for 3 hours, then cooled to 0° C. and slowly colorless crystals of tetrahydro-1,3-thiazine-2-thione were obtained and filtered through a Buckner funnel. The desired tetrahydro-1,3-thiazine-2-thione was obtained as a white crystalline solid (6.89 g, 99%). $^1$H NMR (DMSO-d6, 400 MHz) δ ppm: 10.24 (bs, 1H), 3.29 (dt, J=1.8, 5.2 Hz, 2H), 2.95 (t, J=5.8 Hz, 2H), 1.97 (p, J=5.8 Hz, 2H); $^{13}$C NMR (DMSO-d6, 100 MHz) δ ppm: 191.1, 43.9, 30.1, 20.6; MS m/z for C$_4$H$_7$NS$_2$N [M+H]$^+$ calcd 134.2, Found 132.2.

3-Aminopropanethiol Hydrochloride (42 and 43)

A suspension of tetrahydro-1,3-thiazine-2-thione (7 g, 53 mol) in conc. HCl (45 mL) was heated to reflux for 3 weeks and the reaction progress was monitored by $^1$H NMR. Conc. HCl was evaporated under reduced pressure the using KOH trap for quenching the HCl vapors until an oil remained, a white precipitate of aptH•HCl was obtained by the addition of ethanol/ether. Yield 5.12 g, 76%. minor product 43 (disulfide): $^1$H NMR (D$_2$O, 400 MHz) δ 3.17-3.04 (m, 2H), 3.00 (t, J=7.0 Hz, 2H), 2.15 (p, J=7.4 Hz, 2H); $^{13}$C NMR (D$_2$O, 100 MHz) δ 37.8, 33.3, 25.5; major product (42): $^1$H NMR (D$_2$O, 400 MHz) δ 3.17-3.04 (m, 2H), 2.79 (t, J=7.2 Hz, 2H), 2.08 (p, J=7.3 Hz, 2H); $^{13}$C NMR (D$_2$O, 100 MHz) δ 37.9, 33.5, 25.7.

Example 5: Synthesis, Purification and Spectral Characterization of Precursor Linear Peptides Fmoc-Pro-Val-O$^t$Bu (27)

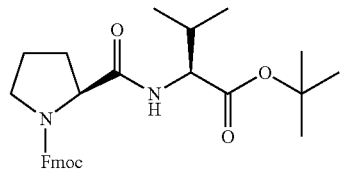

27

Dipeptide 27 was synthesized by following the above general procedure for EDCl peptide coupling and purified by silica gel column chromatography (EtOAc:Hexane—2:3) as a white solid (yield: 87%) trans/cis=1.1:1; trans isomer: $^1$H NMR (400 MHz, CDCl$_3$) δ ppm: 7.66 (d, J=7.4 Hz, 2H), 7.62 (d, J=7.4 Hz, 2H), 7.30 (t, J=7.5 Hz, 2H), 7.23 (t, J=7.5 Hz, 2H), 7.02 (d, J=7.0 Hz, 1H), 4.44-4.39 (m, 1H), 4.33 (dd, J=2.9, 8.2 Hz, 1H), 4.23-4.08 (m, 2H), 3.62-3.31 (m, 4H), 2.36-2.21 (m, 1H), 2.18-2.02 (m, 1H), 1.94-1.83 (m, 1H), 1.79 (td, J=7.5, 14.4 Hz, 1H), 1.70-1.60 (m, 1H), 1.59-1.48 (m, 1H), 1.41-1.37 (m, 1H), 1.38 (m, 9H), 0.83 (d, J=6.9 Hz, 4H), 0.82 (d, J=7.0 Hz, 3H); cis isomer: $^1$H NMR (400 MHz, CDCl$_3$) δ ppm: 7.69 (d, J=6.9 Hz, 2H), 7.62 (d, J=7.4 Hz, 2H), 7.30 (t, J=7.5 Hz, 2H), 7.23 (t, J=7.5 Hz, 2H), 6.51 (d, J=7.5 Hz, 2H), 4.44-4.39 (m, 1H), 4.33 (dd, J=2.9, 8.2 Hz, 1H), 4.23-4.08 (m, 2H), 3.62-3.31 (m, 4H), 2.18-2.02 (m, 2H), 1.94-1.83 (m, 1H), 1.79 (td, J=7.5, 14.4 Hz, 1H), 1.70-1.60 (m, 1H), 1.59-1.48 (m, 1H), 1.41-1.37 (m, 1H), 1.38 (m, 9H), 0.80 (d, J=6.9 Hz, 3H), 0.79 (d, J=7.3 Hz, 3H); $^{13}$C NMR (100 MHz, CDCl$_3$) δ ppm: 171.8, 171.4, 170.9, 170.7, 156.0, 141.2, 128.7, 127.7, 127.1, 127.0, 125.1, 121.0, 119.9, 119.7, 109.4, 107.7, 85.1, 81.8, 68.1, 67.7, 61.2, 61.1, 60.5, 60.4, 57.7, 57.2, 56.9, 50.4, 47.5, 47.2, 46.9, 36.0, 34.6, 34.5, 31.9, 31.6, 31.4, 29.7, 29.0, 28.2, 28.0, 27.8, 25.7, 25.3, 24.8, 24.7, 23.6, 22.6, 21.0, 20.7, 19.0, 18.8, 18.7, 17.5, 14.1; MS (ESI): found: [M+Na]⁺, 515.4.

Fmoc-ᴰPro-Val-OᵗBu (28)

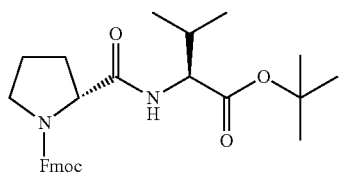

Dipeptide 28 was synthesized by following the above general procedure for EDCl peptide coupling and purified by silica gel column chromatography (EtOAc:Hexane—2:3) as a viscous oil (yield: 92%) Observed only trans isomer: ¹H NMR (400 MHz, CDCl₃) δ ppm: 7.77 (d, J=7.4 Hz, 2H), 7.60 (d, J=6.7 Hz, 2H), 7.40 (t, J=7.2 Hz, 2H), 7.32 (tt, J=1.6, 7.4 Hz, 2H), 7.01 (d, J=7.8 Hz, 3H), 4.49-4.36 (m, 4H), 4.32-4.23 (m, 1H), 4.23-4.11 (m, 1H), 3.70-3.52 (m, 1H), 3.52-3.37 (m, 1H), 2.41-2.27 (m, 1H), 2.27-2.09 (m, 2H), 2.07-1.88 (m, 1H), 1.43 (s, 9H), 0.86 (d, J=6.0 Hz, 6H); ¹³C NMR (100 MHz, CDCl₃) δ ppm: 171.3, 170.7, 161.2, 143.8, 141.3, 127.7, 127.1, 125.1, 120.0, 81.6, 67.8, 60.7, 57.5, 53.4, 47.1, 31.3, 28.8, 28.0, 24.6, 18.9, 17.5; MS (ESI): found: [M+Na]⁺, 515.4.

Fmoc-ᴰPro-Pro-Val-OᵗBu (29)

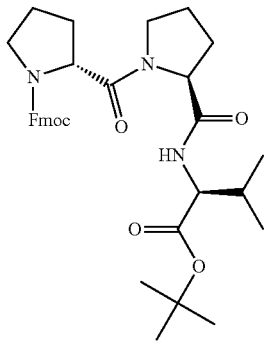

Tripeptide 29 was synthesized by following the above general procedure for EDCl peptide coupling as a viscous oil (yield: 83%). This tripeptide aggregated to form an insoluble material once solidified and decomposed on silica gel. To overcome this difficulty, we proceeded further without purification. trans/cis=3:1; trans isomer: ¹H NMR (400 MHz, CDCl₃) δ ppm: 8.09 (d, J=8.2 Hz, 1H), 7.68 (d, J=7.5 Hz, 2H), 7.63 (d, J=7.4 Hz, 2H), 7.29 (t, J=7.4 Hz, 2H), 7.22 (t, J=7.4 Hz, 2H), 4.34 (dd, J=4.7, 9.4 Hz, 1H), 3.97 (t, J=8.0 Hz, 1H), 3.69 (dd, J=4.9, 9.2 Hz, 1H), 3.02-2.92 (m, 6H), 2.55-2.45 (m, 2H), 2.40 (dd, J=3.1, 9.4 Hz, 1H), 2.16-2.01 (m, 2H), 1.89-1.77 (m, 1H), 1.74-1.69 (m, 1H), 1.67-1.58 (m, 3H), 1.47-1.44 (m, 1H), 1.40 (s, 9H), 0.85 (d, J=6.8 Hz, 3H), 0.82 (d, J=7.0 Hz, 3H). cis isomer: ¹H NMR (400 MHz, CDCl₃) δ ppm: 7.80 (d, J=8.8 Hz, 1H), 7.67 (d, J=7.3 Hz, 2H), 7.63 (d, J=7.4 Hz, 2H), 7.29 (t, J=7.4 Hz, 2H), 7.22 (t, J=7.4 Hz, 2H), 4.30 (dd, J=4.9, 8.7 Hz, 1H), 3.97 (t, J=8.0 Hz, 1H), 3.46-3.39 (m, 1H), 3.38-3.31 (m, 1H), 3.13 (dd, J=3.2, 9.9 Hz, 2H), 3.07 (dd, J=3.9, 9.5 Hz, 2H), 2.89 (t, J=6.2 Hz, 2H), 2.86 (t, J=5.9 Hz, 2H), 2.55-2.45 (m, 2H), 2.16-2.01 (m, 2H), 1.89-1.77 (m, 1H), 1.74-1.69 (m, 1H), 1.67-1.58 (m, 3H), 1.47-1.44 (m, 1H), 1.38 (s, 9H), 0.86 (d, J=6.9 Hz, 3H), 0.82 (d, J=7.0 Hz, 3H); MS (ESI): found: [M+Na]⁺, 612.5.

Fmoc-Pro-ᴰPro-Val-OᵗBu (30)

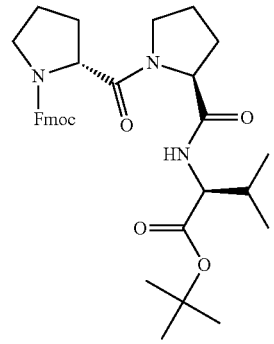

Tripeptide 30 was synthesized by following the above general procedure for EDCl peptide coupling as a viscous oil (yield: 76%). this tripeptide aggregated to form an insoluble material once solidified and decomposed on silica gel. To overcome this difficulty, we proceeded further without purification and characterization of the tripeptides. MS (ESI): found: [M+Na]+, 612.5

Boc-Asp(ᴰPro-Pro-Val-OᵗBu)-OBn (31a)

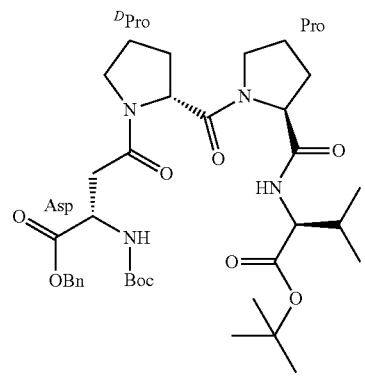

Tetrapeptide 31a was synthesized by following the above general procedure for mixed anhydride peptide coupling and purified by silica gel column chromatography (EtOAc: Hexane—3:1) as a viscous oil (yield: 75%). trans:cis=1:0.6 trans isomer: ¹H NMR (400 MHz, CDCl₃) δ ppm: 7.48 (d, J=8.2 Hz, 2H), 7.40-7.28 (m, 5H), 6.03 (d, J=7.4 Hz, 2H), 5.22 (d, J=12.4 Hz, 1H), 5.14 (d, J=14.5 Hz, 1H), 4.66 (d, J=7.4 Hz, 1H), 4.59 (dd, J=4.7, 7.8 Hz, 1H), 4.51-4.43 (m, 1H), 4.27 (dd, J=6.3, 8.6 Hz, 1H), 3.94 (td, J=4.5, 9.0 Hz, 1H), 3.72-3.62 (m, 1H), 3.62-3.51 (m, 1H), 3.44 (q, J=8.8 Hz, 1H), 2.98 (dd, J=5.1, 13.7 Hz, 2H), 2.50-2.43 (m, 1H), 2.35-2.07 (m, 5H), 2.04-1.80 (m, 4H), 1.41 (s, 9H), 0.90 (d, J=7.0 Hz, 6H); cis isomer: $^1$H NMR (400 MHz, CDCl$_3$) δ ppm: 7.40-7.28 (m, 5H), 6.37 (d, J=8.6 Hz, 1H), 5.70 (d, J=8.6 Hz, 1H), 5.21 (d, J=13.2 Hz, 1H), 5.11 (d, J=12.7 Hz, 1H), 5.07 (d, J=5.5 Hz, 1H), 4.56-4.51 (m, 1H), 4.51-4.43 (m, 1H), 4.35 (d, J=8.2 Hz, 1H), 4.30 (dd, J=6.3, 8.6 Hz, 1H), 3.72-3.62 (m, 1H), 3.62-3.51 (m, 1H), 3.44 (q, J=8.8 Hz, 1H), 2.94 (dd, J=4.1, 16.6 Hz, 1H), 2.80 (dd, J=4.1, 16.6 Hz, 1H), 2.35-2.07 (m, 5H), 2.04-1.80 (m, 4H), 1.46 (s, 9H), 0.88 (d, J=7.1 Hz, 3H), 0.88 (d, J=7.2 Hz, 3H); MS (ESI): found: [M+Na]$^+$, 695.6.

Boc-$^D$Asp($^D$Pro-Pro-Val-O$^t$Bu)-OBn (31b)

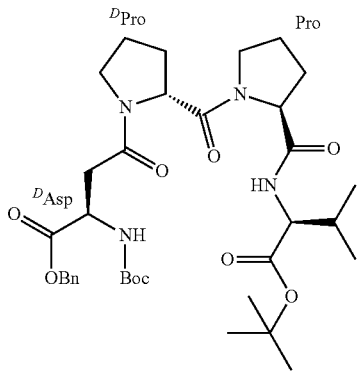

31b

Tetrapeptide 31b was synthesized by following the above general procedure for mixed anhydride peptide coupling and purified by silica gel column chromatography (EtOAc: Hexane—3:1) as a viscous oil (yield: 77%). trans:cis=1:0.3 trans isomer: $^1$H NMR (400 MHz, CDCl$_3$) δ ppm: 7.53 (d, J=8.2 Hz, 1H), 7.37-7.26 (m, 5H), 6.05 (d, J=9.0 Hz, 1H), 5.22 (d, J=12.1 Hz, 1H), 5.09 (d, J=12.9 Hz, 1H), 4.60 (d, J=7.8 Hz, 1H), 4.59-4.51 (m, 1H), 4.48 (dd, J=3.7, 8.4 Hz, 1H), 4.22 (dd, J=5.7, 8.4 Hz, 2H), 3.87 (dt, J=3.0, 8.4 Hz, 1H), 3.68-3.51 (m, 2H), 3.46-3.31 (m, 2H), 3.13 (dd, J=4.7, 16.4 Hz, 1H), 2.65 (dd, J=3.5, 16.7 Hz, 1H), 2.46 (dd, J=5.5, 12.1 Hz, 2H), 2.33-1.67 (m, 8H), 1.41 (s, 9H), 1.39 (s, 9H), 0.90 (d, J=7.0 Hz, 3H), 0.87 d, J=7.0 Hz, 3H); $^{13}$C NMR (100 MHz, CDCl$_3$) δ ppm: 171.7, 171.6, 170.6, 170.5, 169.1, 156.0, 135.8, 128.4, 128.1, 128.0, 81.1, 79.7, 66.8, 60.2, 58.2, 57.6, 53.4, 50.2, 47.4, 47.1, 35.9, 30.6, 28.3, 28.0, 27.5, 24.7, 24.6, 19.1, 17.8; cis isomer: $^1$H NMR (400 MHz, CDCl$_3$) δ ppm: 7.37-7.26 (m, 5H), 6.32 (d, J=8.6 Hz, 1H), 5.82 (d, J=9.8 Hz, 1H), 5.18 (d, J=13.0 Hz, 1H), 5.02 (d, J=12.5 Hz, 1H), 4.95 (dd, J=2.5, 8.7 Hz, 1H), 4.48 (dd, J=3.7, 8.4 Hz, 2H), 4.43 (dd, J=4.5, 8.8 Hz, 1H), 4.21 (dd, J=5.7, 8.4 Hz, 1H), 3.68-3.51 (m, 1H), 3.46-3.31 (m, 3H), 3.08 (dd, J=4.7, 16.4 Hz, 1H), 2.63 (dd, J=J=4.0, 16.6 Hz, 1H), 2.46 (dd, J=5.5, 12.1 Hz, 1H), 2.29-1.67 (m, 8H), 1.44 (s, 9H), 1.41 (s., 9H), 0.89 (d, J=7.0 Hz, 3H), 0.85 (d, J=7.0 Hz, 3H); $^{13}$C NMR (100 MHz, CDCl$_3$) δ ppm: 173.1, 172.1, 170.5, 170.5, 168.8, 155.8, 135.8, 128.4, 128.1, 128.0, 82.3, 79.7, 67.0, 61.7, 57.5, 57.1, 50.0, 47.5, 47.1, 36.3, 32.2, 31.5, 29.6, 28.6, 28.0, 25.0, 22.7, 19.0, 17.6; MS (ESI): found: [M+Na]$^+$, 695.6.

Boc-Asp(Pro-$^D$Pro-Val-O$^t$Bu)-OBn (32a)

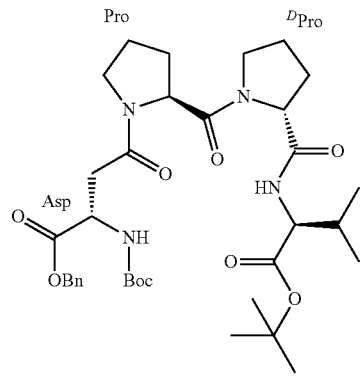

32a

Tetrapeptide 32a was synthesized by following the above general procedure for mixed anhydride peptide coupling and purified by silica gel column chromatography (EtOAc: Hexane—3:1) as a viscous oil (yield: 73%) trans:cis=1:0.2 trans isomer: $^1$H NMR (400 MHz, CDCl$_3$) δ ppm: 7.41-7.28 (m, 5H), 6.78 (d, J=8.6 Hz, 1H), 5.87 (d, J=9.4 Hz, 1H), 5.12 (d, J=14.0 Hz, 1H), 5.06 (d, J=12.5 Hz, 2H), 4.63 (dd, J=3.9, 9.0 Hz, 2H), 4.59 (dd, J=2.0, 6.8 Hz, 2H), 4.31 (dd, J=5.9, 8.6 Hz, 2H), 3.95 (t, J=7.7 Hz, 1H), 3.73-3.53 (m, 2H), 3.51-3.33 (m, 3H), 3.14 (dd, J=5.1, 16.4 Hz, 1H), 2.66 (dd, J=3.5, 16.4 Hz, 1H), 2.36-2.30 (m, 1H), 2.21-2.10 (m, 2H), 2.10-2.04 (m, 1H), 2.04-1.95 (m, 3H), 1.95-1.84 (m, 2H), 1.45 (s, 9H), 0.94 (d, J=7.0 Hz, 3H), 0.91 (d, J=6.7 Hz, 3H). $^{13}$C NMR (100 MHz, CDCl$_3$) δ ppm: 171.5, 171.2, 170.8, 170.7, 169.0, 155.8, 135.7, 128.4, 128.1, 128.0, 81.2, 79.8, 66.9, 60.7, 58.2, 57.8, 50.2, 47.5, 47.1, 36.1, 30.5, 29.5, 28.4, 28.3, 28.0, 24.8, 24.2, 19.0, 17.9; cis isomer: $^1$H NMR (400 MHz, CDCl$_3$) δ ppm: 7.41-7.28 (m, 5H), 6.24 (d, J=8.6 Hz, 1H), 6.05 (d, J=9.8 Hz, 1H), 5.25 (d, J=12.0 Hz, 2H), 5.12 (d, J=14.0 Hz, 1H), 5.06 (d, J=12.5 Hz, 2H), 4.99 (dd, J=2.6, 7.8 Hz, 1H), 4.79 (dd, J=2.3, 7.8 Hz, 1H), 4.59 (dd, J=2.0, 6.8 Hz, 2H), 4.31 (dd, J=5.9, 8.6 Hz, 2H), 4.12 (q, J=7.7 Hz, 1H), 3.73-3.53 (m, 2H), 3.51-3.33 (m, 3H), 3.17 (dd, J=5.1, 16.4 Hz, 1H), 2.73 (dd, J=3.5, 16.8 Hz, 1H), 2.36-2.30 (m, 1H), 2.21-2.10 (m, 2H), 2.10-2.04 (m, 1H), 2.04-1.95 (m, 3H), 1.95-1.84 (m, 2H), 1.46 (s, 9H), 0.95 (d, J=7.0 Hz, 3H), 0.91 (d, J=6.7 Hz, 3H); $^{13}$C NMR (100 MHz, CDCl$_3$) δ ppm: 171.8, 171.2, 170.8, 169.4, 168.9, 155.9, 135.8, 128.4, 128.3, 127.9, 81.2, 79.8, 66.8, 61.3, 57.5, 56.4, 50.0, 46.4, 36.2, 31.2, 31.1, 29.8, 29.0, 28.0, 26.3, 25.5, 24.9, 24.5, 17.8; MS (ESI): found: [M+Na]$^+$, 695.6.

Boc-$^D$Asp(Pro-$^D$Pro-Val-O$^t$Bu)-OBn (32b)

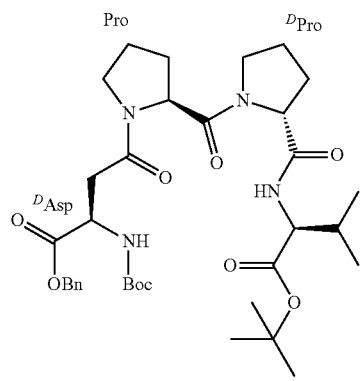

32b

Tetrapeptide 32b was synthesized by following the above general procedure for mixed anhydride peptide coupling and purified by silica gel column chromatography (EtOAc: Hexane—3:1) as a viscous oil (yield: 66%). $^1$H NMR (400 MHz, CDCl$_3$) δ ppm: 7.36-7.33 (m, 5H), 6.97 (d, J=8.6 Hz, 1H), 5.67 (d, J=8.2 Hz, 1H), 5.20 (d, J=12.2 Hz, 1H), 5.10 (d, J=12.0 Hz, 1H), 4.63 (d, J=5.5 Hz, 1H), 4.58-4.51 (m, 2H), 4.24 (dd, J=6.1, 8.0 Hz, 1H), 4.00 (t, J=7.8 Hz, 1H), 3.72-3.51 (m, 2H), 3.50-3.41 (m, 1H), 2.96 (dd, J=6.0, 16.0 Hz, 1H), 2.86 (dd, J=6.0, 16.2 Hz, 1H), 2.39-2.29 (m, 1H), 2.25-2.05 (m, 3H), 2.04-1.82 (m, 5H), 1.44 (s, 9H), 1.42 (s, 9H), 0.93 (d, J=6.7 Hz, 3H), 0.89 (d, J=6.7 Hz, 3H). $^{13}$C NMR (100 MHz, CDCl$_3$) δ ppm: 171.1, 171.0, 170.9, 170.8, 170.7, 155.5, 135.6, 128.5, 128.3, 128.2, 81.1, 77.2, 67.2, 60.6, 58.4, 58.1, 50.6, 47.6, 47.2, 36.3, 30.5, 29.6, 28.6, 28.3, 28.1, 25.0, 24.1, 18.9, 18.4. MS (ESI): found: [M+Na]$^+$, 695.6.

Example 6: Synthesis of Substrate A

Scheme 2 shows the synthetic scheme for preparing Substrate A, as described in WO 2013/06739, the contents of which are hereby incorporated by reference.

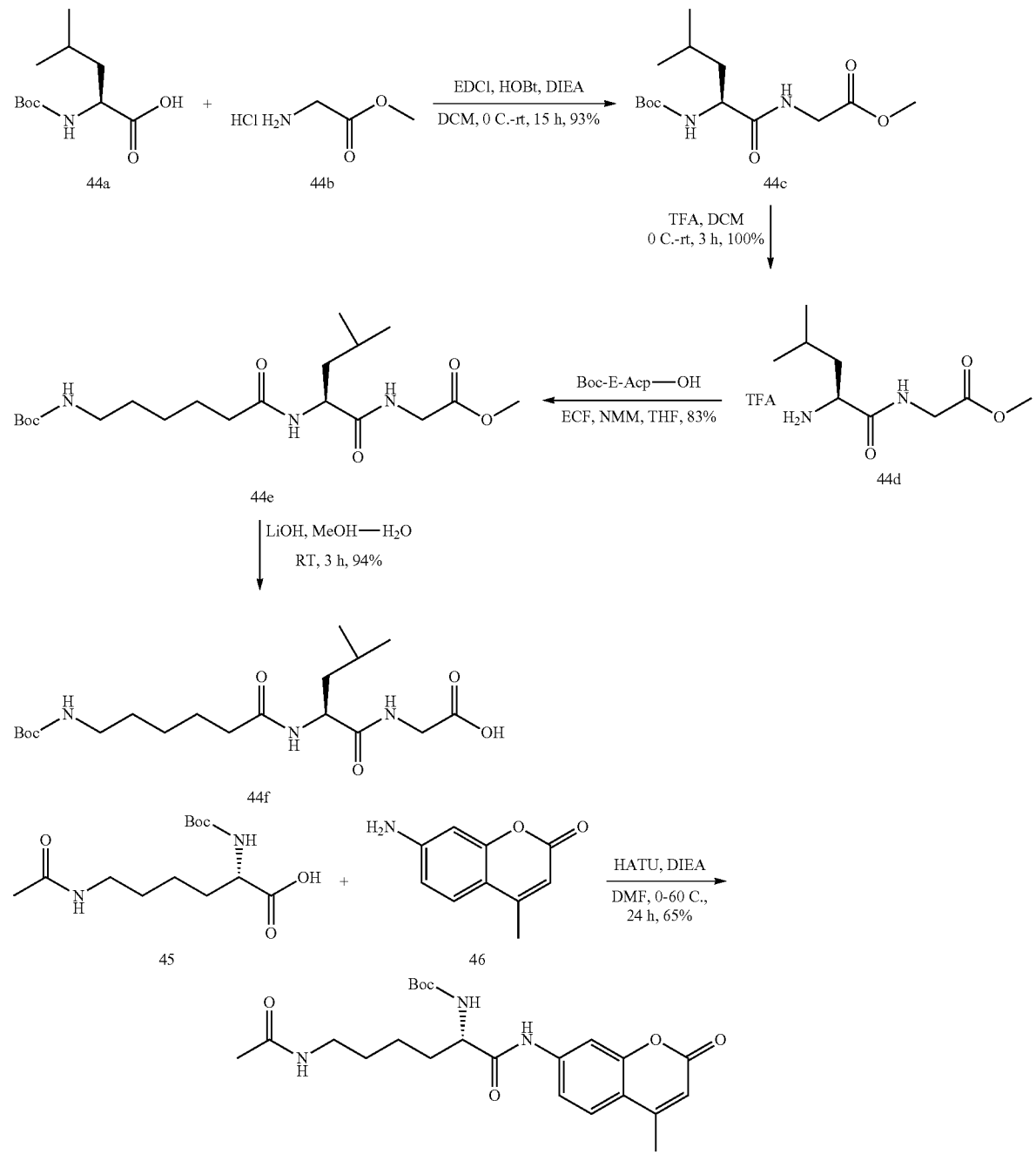

-continued
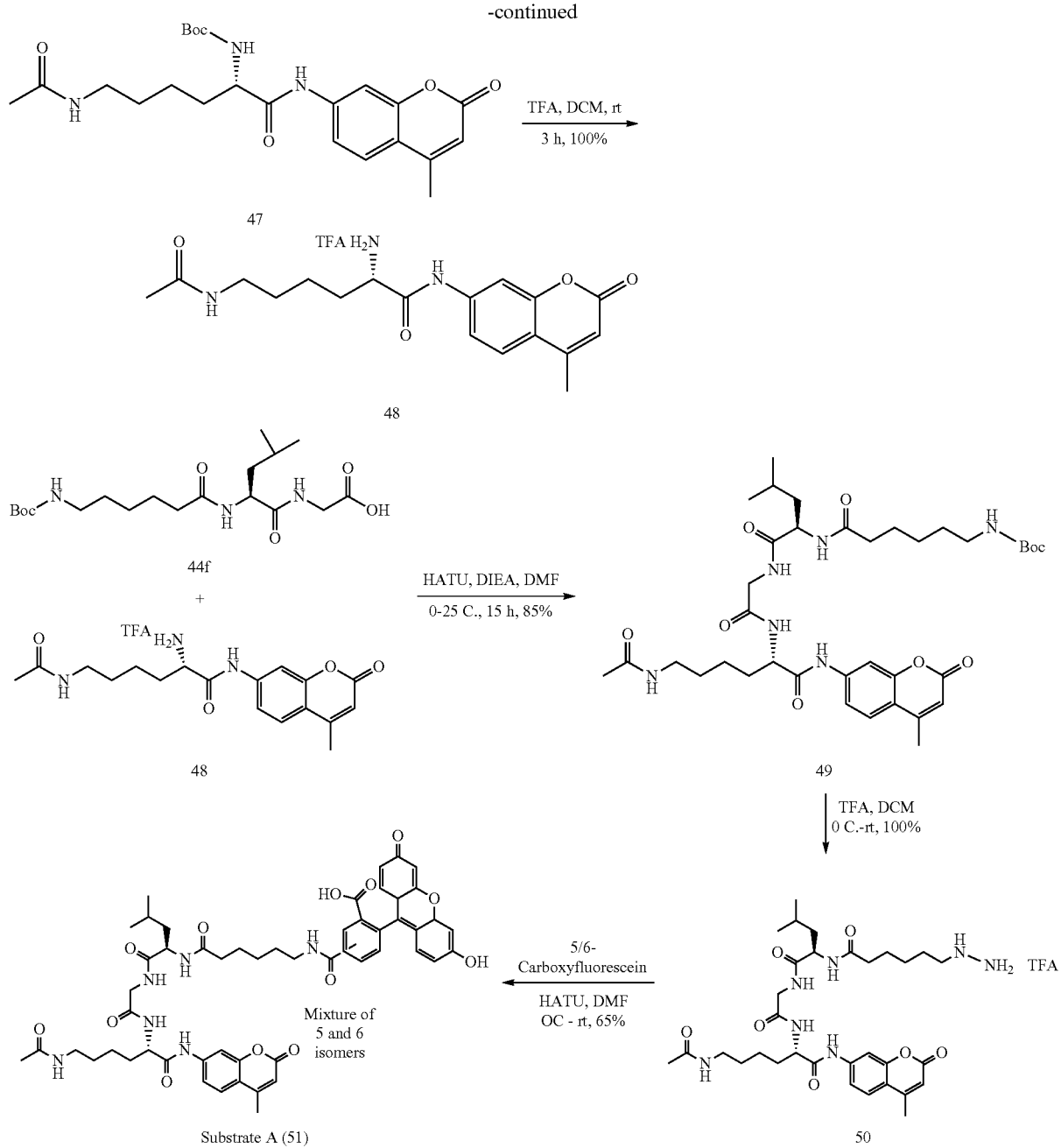
Boc-Leu-Gly-OMe (44c)
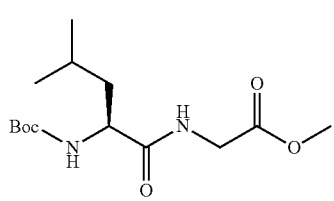
Dipeptide 44c was synthesized by following the above general procedure for EDCL peptide coupling and purified by silical gel column chromatography (EtOAc:Hexane—1:3) as a viscous oil (yield: 93%). $^1$H NMR (400 MHz, CDCl$_3$) δ ppm: 6.59 (bs, 1H), 4.83 (bs, 1H), 4.20-4.12 (m, 1H), 4.05 (d, J=5.5 Hz, 2H), 3.76 (s, 3H), 1.74-1.67 (m, 2H), 1.54-1.47 (m, 1H), 1.46-1.36 (s, 9H), 0.96 (d, J=6.2 Hz, 3H), 0.94 (d, J=6.3 Hz, 3H). MS (ESI): found: [M+Na]$^+$, 325.4.
TFA.Leu-Gly-OMe (44d)
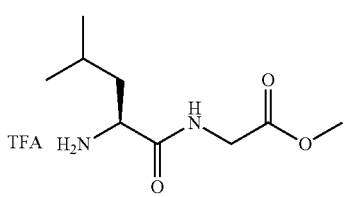

Dipeptide amine salt 44d was synthesized by following the above general procedure for acidic cleavage of N-tert-butyloxycarbonyl (Boc) and showed >98% purity by LC-MS used without further purification, obtained the desired peptide as a white solid (yield: 94%). MS (ESI): found: [M+H]+, 203.3.

Boc-Acp-Leu-Gly-OMe (44e)

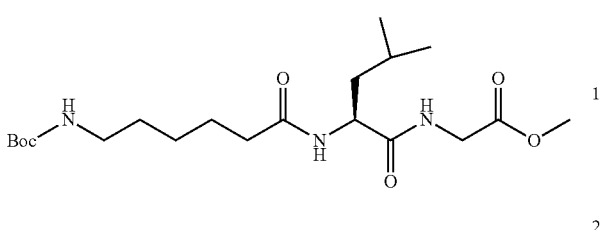

Tetrapeptide 44e was synthesized by following the above general procedure for mixed anhydride peptide coupling and purified by silica gel column chromatography (EtOAc:Hexane—2:1) as a white solid (yield: 83%). $^1$H NMR (400 MHz, CDCl$_3$) δ ppm: 6.78 (bs, 1H), 6.05 (d, J=8.2 Hz, 1H), 4.64 (bs, 1H), 4.51 (dt, J=5.7, 8.5 Hz, 1H), 4.03 (d, J=5.8 Hz, 2H), 3.76 (s, 3H), 3.16-3.04 (m, 2H), 2.66-2.40 (m, 3H), 2.23 (t, J=7.6 Hz, 2H), 1.75-1.59 (m, 3H), 1.58-1.46 (m, 2H), 1.38-1.30 (m, 1H), 1.45 (s, 9H), 0.95 (d, J=6.3 Hz, 3H), 0.93 (d, J=6.3 Hz, 3H); MS (ESI): found: [M+Na]+, 438.4.

Boc-Acp-Leu-Gly-OH (44f)

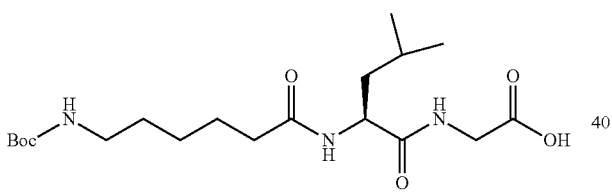

Tetrapeptide 44f having the carboxylic acid was synthesized by following the above general procedure for general procedure for LiOH base mediated hydrolysis of methyl ester and used without further purification, obtained the desired peptide as a fluffy solid (yield: 94%). MS (ESI): found: [M+Na]+, 424.4.

Boc-Lys(Ac)-Cumarin Dipeptide (47)

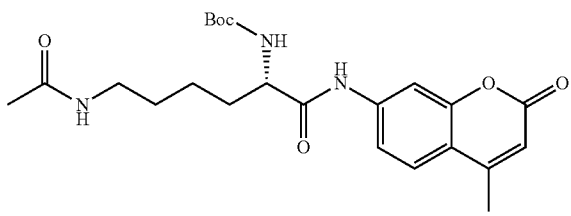

Dipeptide 47 was synthesized by following the above general procedure for HATU peptide coupling (0-60° C.) for 12 hours and purified by silica gel column chromatography (EtOAc:Hexane—3:1) as a white solid (yield: 65%). $^1$H NMR (400 MHz, CDCl$_3$) δ ppm: 9.34 (bs, 1H), 7.69 (s, 1H), 7.55-7.36 (m, 2H), 6.79 (bs, 1H), 5.55 (d, J=7.2 Hz, 1H), 4.41-4.16 (m, 1H), 3.35-3.26 (m, 2H), 2.39 (s, 3H), 2.07 (s, 3H), 2.00-1.87 (m, 1H), 1.74 (dd, J=4.9, 13.5 Hz, 1H), 1.65-1.54 (m, 3H), 1.53-1.47 (m, 1H), 1.45 (s, 9H), 1.30-1.20 (m, 1H), 1.20-1.11 (m, 1H). MS (ESI): found: [M+Na]+, 468.4.

TFA.Lys(Ac)-Cumarin Dipeptide (48)

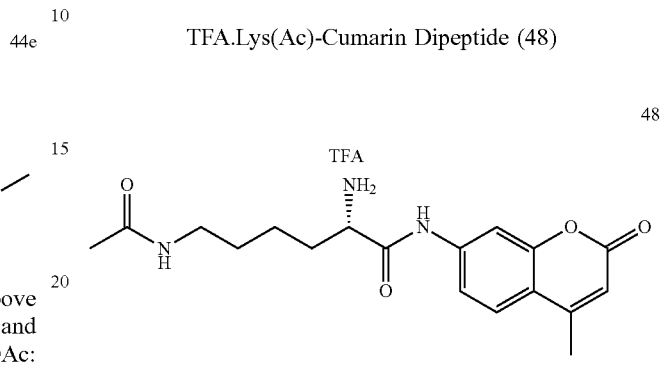

Dipeptide amine salt 48 was synthesized by following the above general procedure for acidic cleavage of N-tert-butyloxycarbonyl (Boc) and showed >98% purity by LC-MS and used without further purification, obtained the desired peptide as a white solid (yield: 94%). MS (ESI): found: [M+H]+, 346.4.

Boc-Acp-Leu-Gly-Lys(Ac)-Cumarin Tetrapeptide (49)

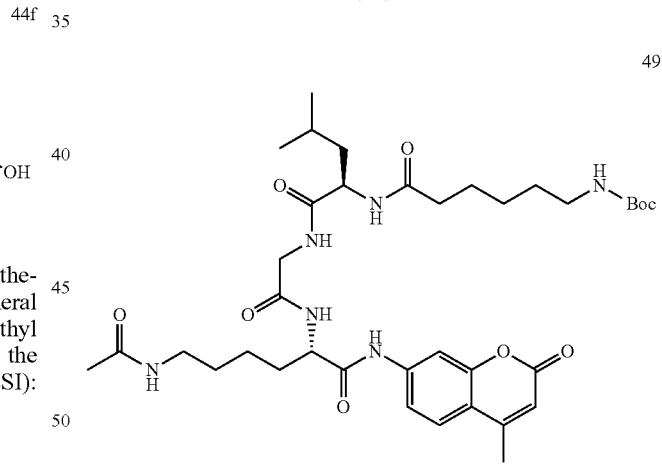

Tetrapeptide 49 was synthesized by following the above general procedure for HATU peptide coupling (0-25° C.) and purified by silica gel column chromatography (EtOAc) as a viscous oil (yield: 85%). $^1$H NMR (400 MHz, CDCl$_3$) δ ppm: 9.64 (bs, 1H), 8.03 (bs, 1H), 7.81 (bs, 1H), 7.71 (s, 1H), 7.60-7.48 (m, J=8.2 Hz, 1H), 7.48-7.37 (m, J=9.0 Hz, 1H), 7.06 (bs, 1H), 7.01 (bs, 1H), 6.14 (s, 1H), 4.92 (bs, 1H), 4.56 (q, J=5.9 Hz, 1H), 4.37-4.23 (m, 1H), 4.04 (dd, J=5.0, 17.0 Hz, 1H), 3.96 (dd, J=5.0, 17.0 Hz, 1H), 3.21 (quin, J=6.0 Hz, 2H), 3.03 (t, J=6.5 Hz, 2H), 2.37 (s, 3H), 2.24 (sxt, J=6.1 Hz, 4H), 2.00 (s, 3H), 1.85-1.83 (m, 1H), 1.75-1.47 (m, 9H), 1.45-1.37 (m, 1H), 1.42 (s, 9H), 1.28 (quin, J=6.0 Hz, 2H), 0.93 (d, J=5.9 Hz, 3H), 0.89 (d, J=5.9 Hz, 3H). MS (ESI): found: [M+Na]+, 751.5.

35
TFA.Acp-Leu-Gly-Lys(Ac)-Cumarin Tetrapeptide (50)

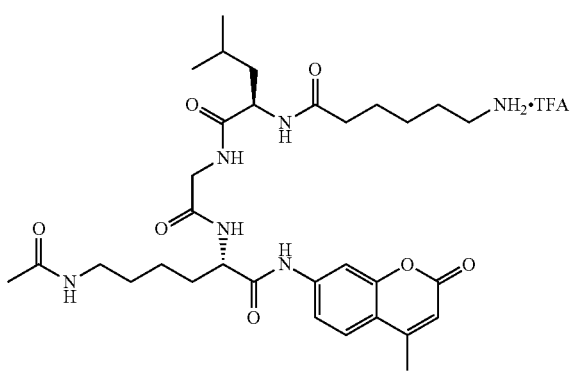

Tetrapeptide 50 was synthesized by following the above general procedure for acidic cleavage of N-tert-butyloxycarbonyl (Boc) and showed >98% purity by LC-MS and used without further purification, obtained the desired peptide as a white solid (yield: 97%). MS (ESI): found: [M+H]$^+$, 629.4.

5/6-Carboxyfluorescein-Acp-Leu-Gly-Lys(Ac)-Cumarin Tetrapeptide (51)

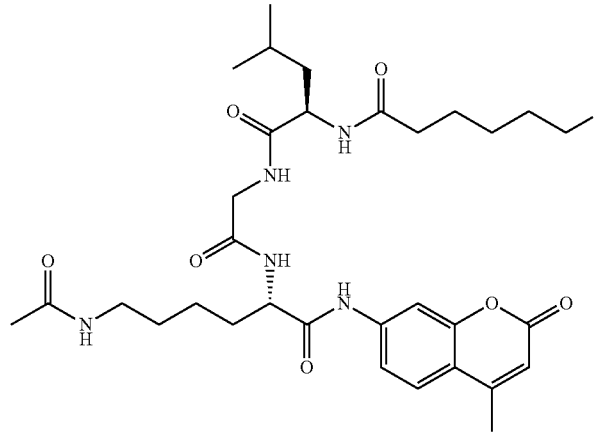

Substrate A (51)

Substrate A (51) (1:0.66 ratio of 5/6-carboxyfluorescein tetrapeptide nonseparable mixture) was synthesized by following the above general procedure for HATU peptide coupling (0-25° C.) and purified by HPLC using 20-60% acetonitrile gradient for 30 minutes (yield: 67%) $^1$H NMR (400 MHz, 5:2 mixture of CDCl$_3$-DMSO-d$_6$ (400 MHz) δ ppm: 9.71 (s, 1H), 9.64 (s, 1H), 8.56 (s, 1H), 8.32-8.09 (m, 2H), 8.01 (d, J=7.8 Hz, 1H), 7.79 (s, 1H), 7.77-7.65 (m, 2H), 7.51 (dd, J=3.7, 8.4 Hz, 1H), 7.41-7.38 (m, 2H), 7.23 (d, J=8.2 Hz, 1H), 7.00-6.88 (m, 1H), 6.80-6.64 (m, 1H), 6.61-6.50 (m, 2H), 6.17 (s, 1H), 6.12 (s, 1H), 4.61-4.49 (m, 1H), 4.37-4.29 (m, 1H), 4.09-3.96 (m, 2H), 3.83-3.68 (m, 1H), 3.55-3.44 (m, 1H), 3.38-3.27 (m, 1H), 3.18 (d, J=6.3 Hz, 2H), 3.13-3.05 (m, 1H), 2.59 (s, 3H), 2.41 (s, 3H), 2.30 (t, J=6.7 Hz, 1H), 2.21 (t, J=7.2 Hz, 1H), 2.05-1.98 (m, 1H), 1.95 (s, 3H), 1.85 (s, 3H), 1.75-1.48 (m, 9H), 1.48-1.37 (m, 3H), 0.96 (d, J=6.5 Hz, 3H), 0.92 (d, J=6.9 Hz, 3H), 0.87 (d, J=8.0 Hz, 3H), 0.84 (d, J=7.8 Hz, 3H); MS (ESI): found: [M+H]$^+$, 987.7.

Example 7: Synthesis of N-(2-Aminophenyl)-4-[1-(2-thiophen-3-ylethyl)-1H-[1,2,3]triazol-4-yl]benzamide (59)

Scheme 3 shows the synthesis scheme for Compound 59, as described by Suzuki, et al., PLoS One 2013, 8, e68669, the contents of which are hereby incorporated by reference.

Scheme 3: Synthesis of Compound 59

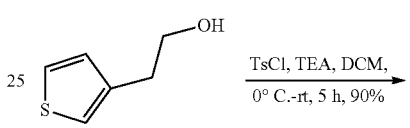

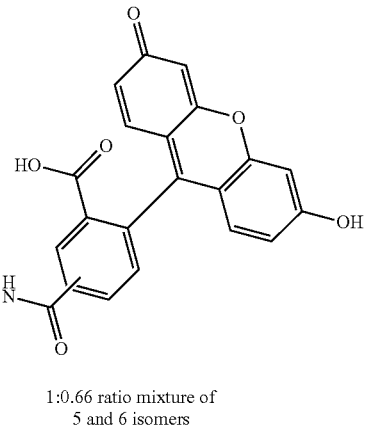

-continued

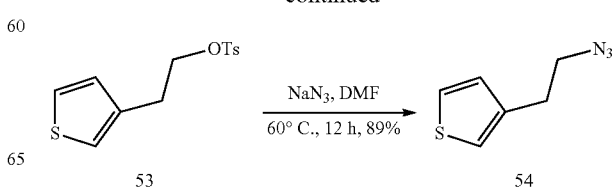

-continued

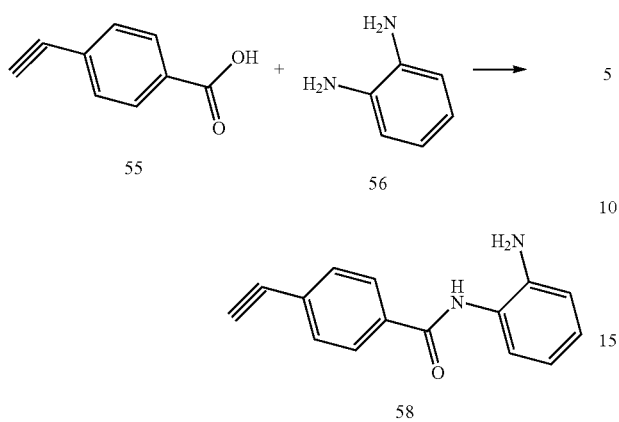

| Reagent | Base | Yeild (%) |
|---|---|---|
| SOCl₂ | NaHCO₃ | <30 |
| HATU | DIEA | 83 |

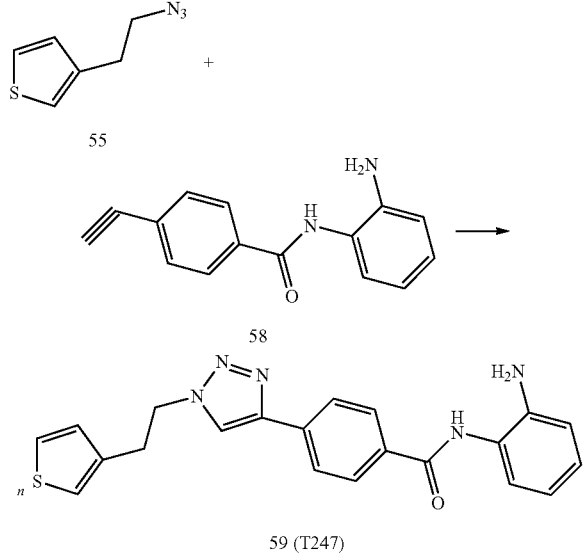

2-(thiophen-3-yl)ethyl 4-methylbenzenesulfonate (53)

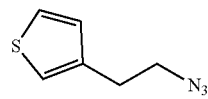

53

A round-bottomed flask was charged with 2-(thiophen-3-yl)ethyl alcohol (5 mmol, 1.00 eq.) and dichloromethane (15 mL). The resulting solution was stirred and cooled to 0° C. and added p-toluenesulfonyl chloride (1.143 g, 6 mmol, 1.20 eq.) portionwise and dropwise triethylamine (0.82 mL, 6 mmol, 1.2 eq.). The resulting solution was stirred at 0° C. until TLC showed complete consumption of starting material. The resulting viscous solution was diluted with water (5 mL) and thoroughly extracted with ethyl acetate (15 mL). The combined organic extracts were washed with saturated aqueous sodium bicarbonate (NaHCO₃) (5 mL) and dried over anhydrous sodium sulphate (Na₂SO₄) and concentrated to give a residue, which was purified by silica gel (100-200 mesh) flash column chromatograph (EtOAc-Hexane mixture-1:20), obtained desired compound as a viscous oil (yield: 90%). $^1$H NMR (400 MHz, CDCl₃) δ ppm: 7.72 (d, J=8.2 Hz, 2H), 7.31 (d, J=8.6 Hz, 2H), 7.22 (dd, J=2.9, 4.9 Hz, 1H), 6.96 (dd, J=0.8, 3.1 Hz, 1H), 6.87 (dd, J=1.2, 5.1 Hz, 1H), 4.21 (t, J=7.0 Hz, 2H), 2.99 (t, J=6.8 Hz, 2H), 2.44 (s, 3H). NMR (100 MHz, DMSO-d₆) δ ppm: 144.7, 136.4, 132.9, 129.8, 128.0, 127.8, 125.8, 122.1, 69.9, 29.8, 21.6; MS (ESI): found: [M+Na]⁺, 283.4.

3-(2-azidoethyl)thiophene (54)

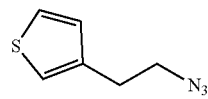

54

A round-bottomed flask was charged with 2-(thiophen-3-yl)ethyl 4-methylbenzenesulfonate (53) (5 mmol, 1.00 eq.) and sodium azide (10 mmol, 2.00 eq.) and N,N-dimethylformamide (15 mL). The resulting solution was stirred at 60° C. until TLC showed complete consumption of starting material. The resulting viscous solution was diluted with water (5 mL) and thoroughly extracted with ethyl acetate (15 mL). The combined organic extracts were washed with saturated aqueous sodium bicarbonate (NaHCO₃) (5 mL) and dried over anhydrous sodium sulphate (Na₂SO₄) and concentrated to give a residue, which was purified by silica gel (100-200 mesh) flash column chromatograph (EtOAc-Hexane mixture—1:20), obtained desired compound as a viscous oil (yield: 90%). $^1$H NMR (400 MHz, CDCl₃) δ ppm: 7.29 (dd, J=2.9, 4.9 Hz, 1H), 7.06 (dd, J=1.0, 1.8 Hz, 1H), 6.98 (d, J=4.7 Hz, 1H), 3.50 (t, J=7.0 Hz, 2H), 2.93 (t, J=7.0 Hz, 2H); $^{13}$C NMR (100 MHz, DMSO-d₆) δ ppm: 138.2, 127.9, 125.9, 121.8, 1.8, 29.8.

N-(2-aminophenyl)-4-ethynylbenzamide (58)

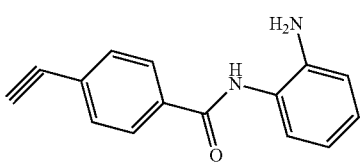

58

Dipeptide 58 was synthesized by following the above general procedure for HATU peptide coupling and purified by silica gel column chromatography (EtOAc:Hexane—4:1) as a white solid (yield: 83%). $^1$H NMR (400 MHz, 5:2 mixture of CDCl₃-DMSO-d₆) δ ppm: 9.97 (bs, 1H), 8.01 (d, J=8.2 Hz, 2H), 7.58 (d, J=7.5 Hz, 2H), 7.46 (d, J=8.0 Hz, 1H), 7.24-7.17 (m, 2H), 7.17-7.08 (m, 1H), 3.34 (s, 1H); $^{13}$C NMR (100 MHz, DMSO-d₆) δ ppm: 165.8, 133.8, 132.7, 131.9, 128.2, 127.9, 127.0, 126.7, 125.6, 124.3, 121.3, 82.6, 80.0; MS (ESI): found: [M+H]⁺, 237.2.

N-(2-Aminophenyl)-4-[1-(2-thiophen-3-ylethyl)-1H-[1,2,3]triazol-4-yl]benzamide (59)

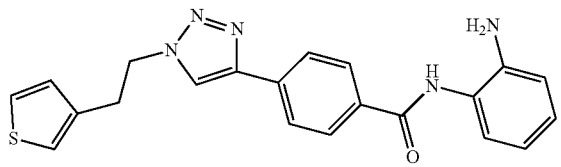

A mixture of 58 (34.0 mg, 0.14 mmol), 54 (22.0 mg, 0.14 mmol), $CuSO_4 \cdot 5H_2O$ (7.0 mg, 0.027 mmol), and sodium ascorbate (10.9 mg, 0.055 mmol) in water and EtOH (v/v=1/1) was stirred vigorously at 50° C. for 4 hours. The reaction mixture was poured into water and extracted with AcOEt. The AcOEt layer was washed with brine, and dried over $Na_2SO_4$. Filtration, concentration in vacuo, and purification by silica gel flash column chromatography (AcOEt/n-hexane=2/1) gave 32.2 mg (59%) of 58 as a pale yellow solid; $^1H$ NMR (400 MHz, DMSO-$d_6$) δ ppm: 9.69 (bs, 1H), 8.10 (d, J=8.2 Hz, 2H), 7.94 (s, 1H), 7.91 (d, J=7.8 Hz, 2H), 7.35 (d, J=7.8 Hz, 1H), 7.34-7.30 (m, 1H), 7.12-7.06 (m, 1H), 7.03 (bs, 1H), 6.97-6.94 (m, 1H), 6.94 (s, 1H), 6.86 (t, J=7.6 Hz, 1H), 4.69 (t, J=7.0 Hz, 2H), 3.33 (t, J=7.3 Hz, 2H), 3.30 (bs, 2H). MS (ESI): found: $[M+H]^P$, 390.3. $^1H$ NMR of compound 59 in DMSO-$d_6$ (400 MHz).

Example 8: General Synthesis of KDAC Inhibitors

Step (i) Synthesis of Cyclic Tetrapeptides-OBn

Cyclic tetrapeptides (CTP) 1a, 1b, 2a and 2b containing a pendant OBn-protected carboxylic acid on the alpha-carbon of Asp were synthesized as shown in Scheme 4.

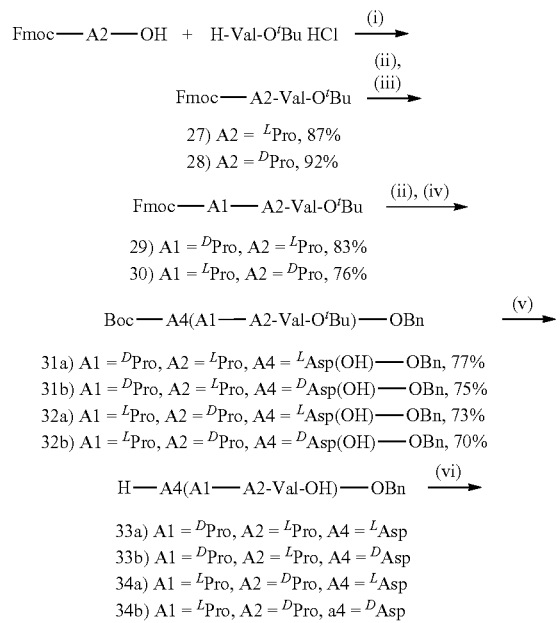

Scheme 4: Synthesis of cyclic tetrapeptide reverse-turn scaffolds

Cyclo-A4(A1—A2-Val)-OBn

1a) A1 = $^D$Pro, A2 = $^L$Pro, A4 = $^L$Asp, 79%
1b) A1 = $^D$Pro, A2 = $^L$Pro, A4 = $^D$Asp, 78%
2a) A1 = $^L$Pro, A2 = $^D$Pro, A4 = $^L$Asp, 67%
2b) A1 = $^L$Pro, A2 = $^D$Pro, A4 = $^D$Asp, 73%

Reagents and conditions: (i) EDC, HOBt, DIEA, DCM, 9 h;
(ii) 20% Piperidine/DCM, rt, 0.5 h, 100%;
(iii) Fmoc—D-Pro-OH, EDC, HOBt, DIEA, DCM, 12 h;
(iv) Boc—Zaa—OBn, EDC, HOBt, DIEA, DCM, 24 h;
(v) 30% TFA/DCM, 0° C. to rt, 3 h, 100%; (vi) DPPA, DIEA, DMF, 0° C. to rt, 72 h.

Using a solution-phase strategy, tert-butyl valine ester hydrochloride was coupled with Fmoc-L-Pro/D-Pro-OH using standard EDC coupling to give protected dipeptide 27 and 28 respectively. After removing the N-terminal Fmoc groups of the dipeptides using 20% piperidine in dichlorethane (DCM), they were coupled with Fmoc-D-Pro/L-Pro-OH to yield linear tripeptides 29 and 30. These tripeptides aggregated to form an insoluble material once solidified and decomposed on silica gel. To overcome this difficulty, the synthesis was continued without purification and characterization of the tripeptides. The Fmoc groups at the N-terminals of tripeptides 29 and 30 were removed, they were coupled with Boc-Asp(OH)-OBn or with Boc-D-Asp(OH)-OBn to give linear tetrapeptides 31a, 31b, 32a and 32b respectively. The N-terminal Boc and C-terminal tert-butyl ester protecting groups were removed quantitatively using 30% trifluoroacetic acid in DCM to obtain the desired products 33a, 33b, 34a, and 34b. Then, macrolactamization was achieved using 2 mM substrate in DMF, diphenylphosphoryl azide (DPPA) and diisopropylethylamine (DIPA) to give cyclic tetrapeptides 1a, 1b, 2a, and 2b in good yields. No epimerized or dimerized compounds was observed during cyclization under these conditions. By synthesizing four CTP scaffolds with a pendant carboxyl group, a variety of warheads could be attached through an amide bond to determine the relative affinities of different warheads in the same structural context against different KDAC isoforms.

General Procedure for Synthesis of CTPs by Using Macrolactamization (1a, 1b, 2a, and 2b)

To a cold (0° C.) stirred solution of N- and C-terminal deprotected tetrapeptide (1 mmol) in dry DMF (500 mL) was added N,N-diisopropylethylamine (6 mmol) dropwise over 1 min followed by diphenyl phosphorazidate (DPPA) (4 mmol) then slowly brought it to room temperature and stirred until the complete consumption of starting material, then DMF was removed under reduced pressure. The resulting viscous solution was diluted with water (5 mL) and thoroughly extracted with ethyl acetate (15 mL). The combined organic extracts were washed with 1 N HCl (5 mL), saturated aqueous sodium bicarbonate ($NaHCO_3$) (5 mL), and dried over anhydrous sodium sulfate ($Na_2SO_4$) and concentrated to give a residue, which was purified by silica gel (100-200 mesh) flash column chromatograph.

Step (ii) Deprotection of the Benzyl Ester

Diastereomerically pure cyclic tetrapeptides 3a and 3b containing free pendant carboxyl groups were obtained in quantitative yield by hydrogenation of the benzyl ester protecting group in compounds 1a and 1b, respectively. Similarly, diastereomerically pure cyclic tetrapeptides 4a and 4b were obtained by hydrogenation of the benzyl ester protecting group in compounds 2a and 2b, respectively. It was found that saponification of the benzyl ester using lithium hydroxide resulted in epimerization of the stereocenter at the ring carbon alpha to the Asp group. Scheme 5 shows the deprotection of the side chain benzyl ester in compound 1a.

material was consumed completely. N,N-Dimethylformamide and dichloromethane were removed under reduced pressure, and the resulting viscous solution was diluted with water (5 mL) and thoroughly extracted with ethyl acetate (15 mL). The combined organic extracts were washed with 1 N HCl (5 mL) and saturated aqueous sodium bicarbonate Scheme 5: Deprotection of side chain benzyl ester

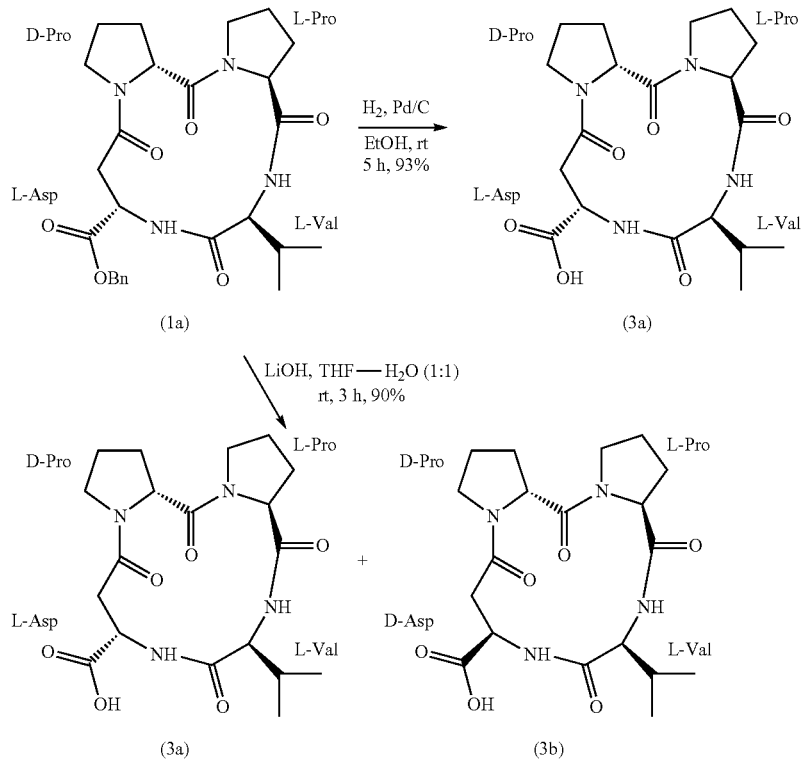

General Procedure for Catalytic Hydrogenation of Benzyl Ester (OBn) Protecting Group (3a, 3b, 4a, and 4b)

A stirred solution of the benzyl ester (1 mmol) and 10% Pd/C (0.1 mmol) in EtOH (10 mL) at 25° C. was placed under an atmosphere of hydrogen. After 4 hours, the mixture was filtered through Celite using EtOH as eluent and concentrated under reduced pressure and proceeded further without purification.

General Procedure for Introducing Warhead on Pendent Carboxylic Acid by Using EDCl Peptide Coupling (7a, 7b, 10a, 10b, 12a, 12b, 16a, 16b, 19a, 19b, 22a, 22b, 23a, and 23b)

To a solution (0° C.) of 1-(3-(dimethylamino)propyl)-3-ethylcarbodiimide hydrochloride (1.3 mmol), 1-hydroxybenzotriazole (1.3 mmol), and cyclo-A3(A1-A2-Val)-OH (1 mmol) in N,Ndimethylformamide (10 mL) added N,N-diisopropylethylamine (3 mmol) was stirred for 15 minutes. Then added solution of amino propyl linker (1 mmol) in N,N-dimethylformamide (2 mL) flask, and the reaction mixture was stirred at room temperature until the starting (NaHCO₃) (5 mL) and dried over anhydrous sodium sulfate (Na₂SO₄) and concentrated to give a residue, which was purified by HPLC.

Step (iii) Introduction of the Linker/Zinc Binding Group

The final step in the synthesis of KDAC inhibitors was to introduce the linker/zinc binding group on the CTP scaffold. Several KDAC inhibitors were prepared having a thiol zinc-binding group, as shown in Scheme 6. First, compounds 3a, 3b, 4a, and 4b were coupled to 2,2'-diaminodiethyl disulfide in the presence of 1-ethyl-3-(3-dimethylaminopropyl)carbodiimide (EDC) to give CTP tetrapeptides 35a, 35b, 36a, and 36b having a disulfide bridge. Similarly, coupling of compounds 3a, 3b, 4a, and 4b with 3,3'-diaminodipropyl disulfide in the presence of EDC yielded disulfides 37a, 37b, 38a, and 38b. In a second step, the abovementioned disulfides were reduced with dithiothreitol (DTT) to give compounds 5a, 5b, 17a, 17b, 6a, 6b, 18a, and 18b having a thiol zinc binding group (warhead). In addition, KDAC inhibitors 11a and 11b having a phosphamide warhead were prepared. As shown in Scheme 6, compounds 11a and 11b were obtained by coupling carboxylic acids 3a and 3b with 2,2'-diaminodiethyl disulfide in the presence of diphenoxyphosphoryl azide (DPPA).

Scheme 6: KDAC inhibitors with thiol or phosphamide warheads

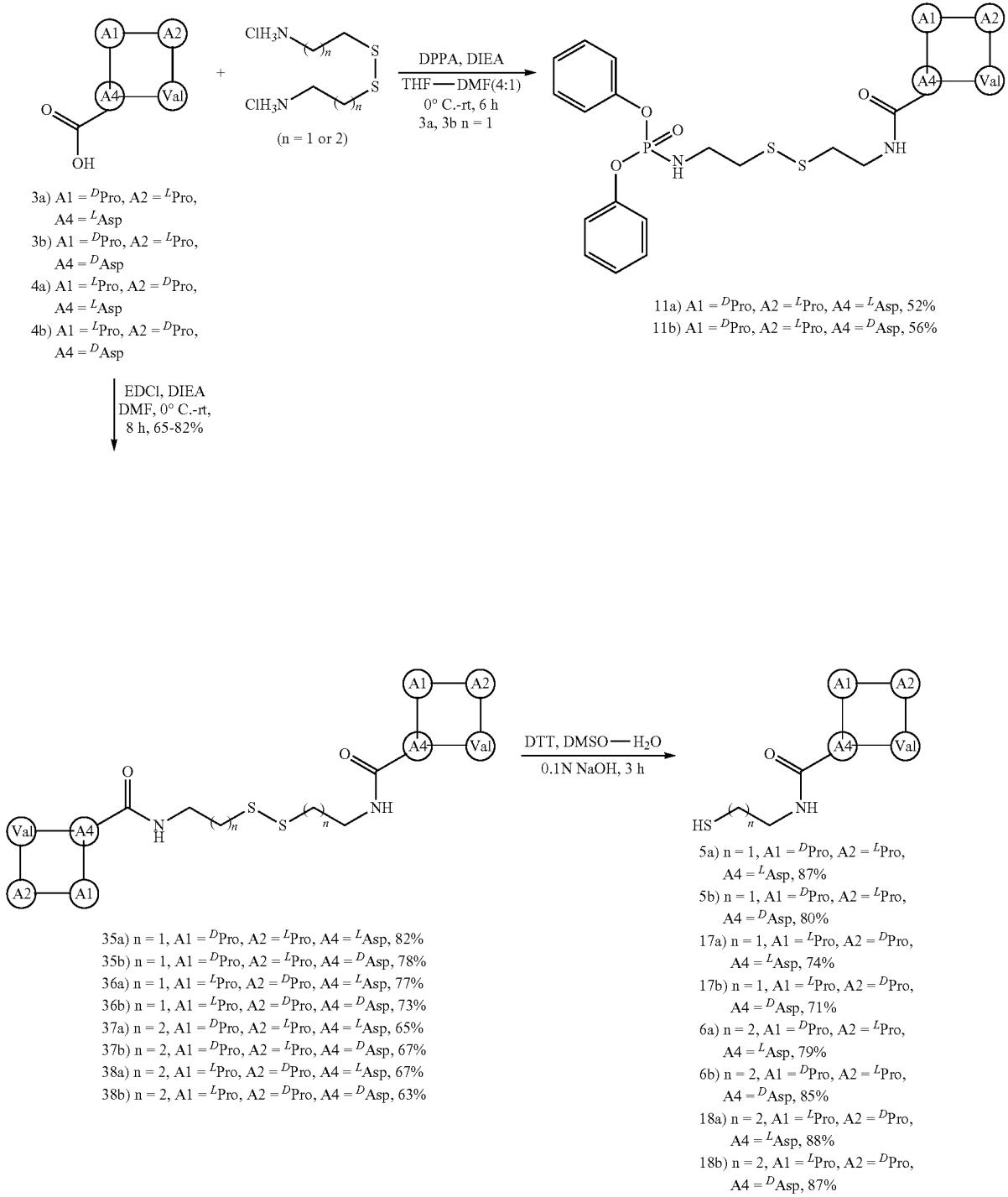

KDAC inhibitors with thioether, hydroxyl, amino, sulfoxide, or sulfone warheads were synthesized as shown in Scheme 7. Compounds 3a, 3b, 4a, and 4b were coupled with functionalized amines in the presence of EDC to generate amides with terminal thioether, hydroxyl or amino warheads. For example, coupling compound 4a with 1,3-diaminopropane gave KDAC inhibitor 16a with an amino warhead; coupling compound 4a with 3-amino-1-propanol gave KDAC inhibitor 22a with a hydroxyl warhead.

Sulfoxide or sulfone warheads were introduced via pH controlled selective oxidation of the corresponding thioethers. Thus, borax catalyzed oxidation of thioethers with hydrogen peroxide at acidic pH furnished sulfoxide 8a, 8b, 20a and 20b, whereas sulfones 9a, 9b, 21a and 21b were obtained at basic pH.

Scheme 7: KDAC inhibitors with thioether, hydroxyl, amino, sulfoxide, or sulfone warheads

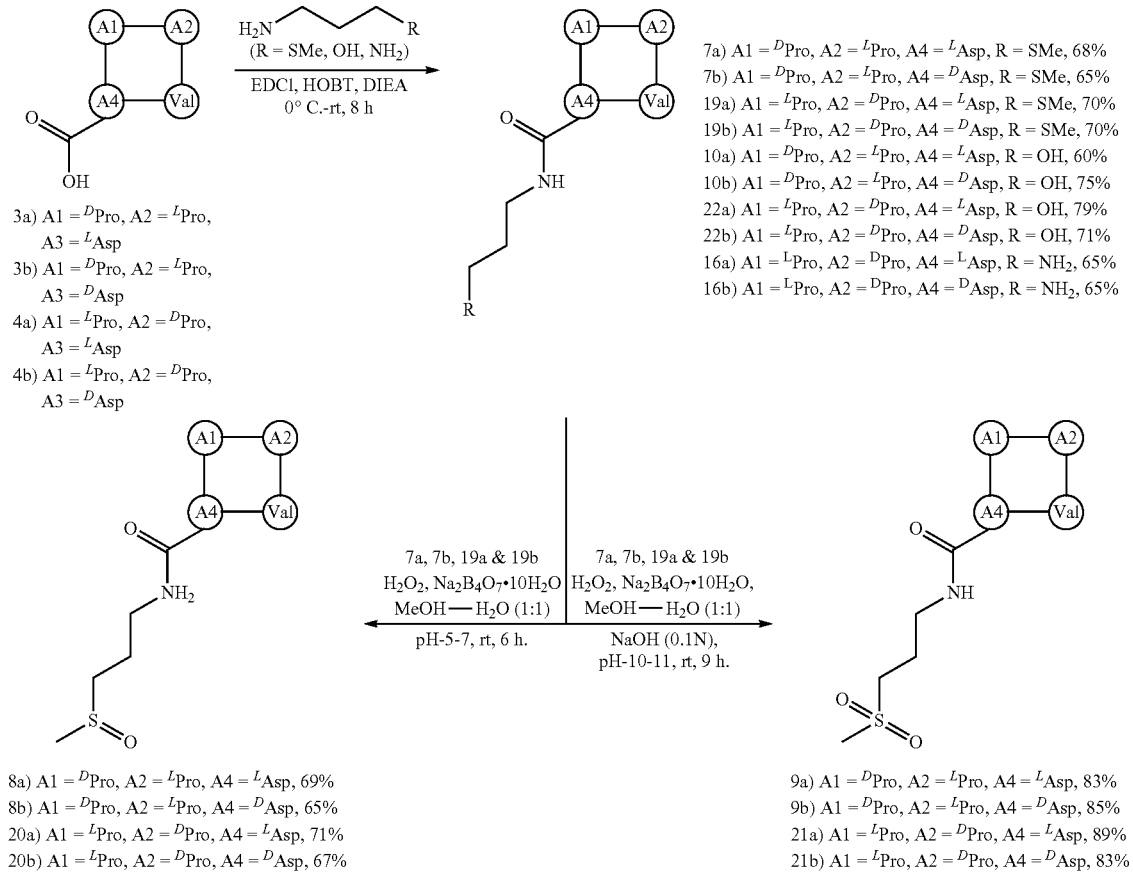

KDAC inhibitors with methyl ester, carboxylic acid, or hydroxamic acid warheads were synthesized as shown in Scheme 8. Compounds 3a, 3b, 4a, and 4b were coupled with methyl 4-aminobutanoate in the presence of EDC to give methyl esters 12a, 12b, 23a, and 23b, respectively. Saponification of the methyl esters with lithium hydroxide yielded KDAC inhibitors 13a, 13b, 24a, and 24b with carboxylic acid warheads. Similarly, reaction of the methyl esters with hydroxyl amine in the presence of potassium hydroxide gave KDAC inhibitors 14a, 14b, 25a, and 25b with hydroxamic acid warheads.

Scheme 8: KDAC inhibitors with methyl ester, carboxylic acid, or hydroxamic acid warheads

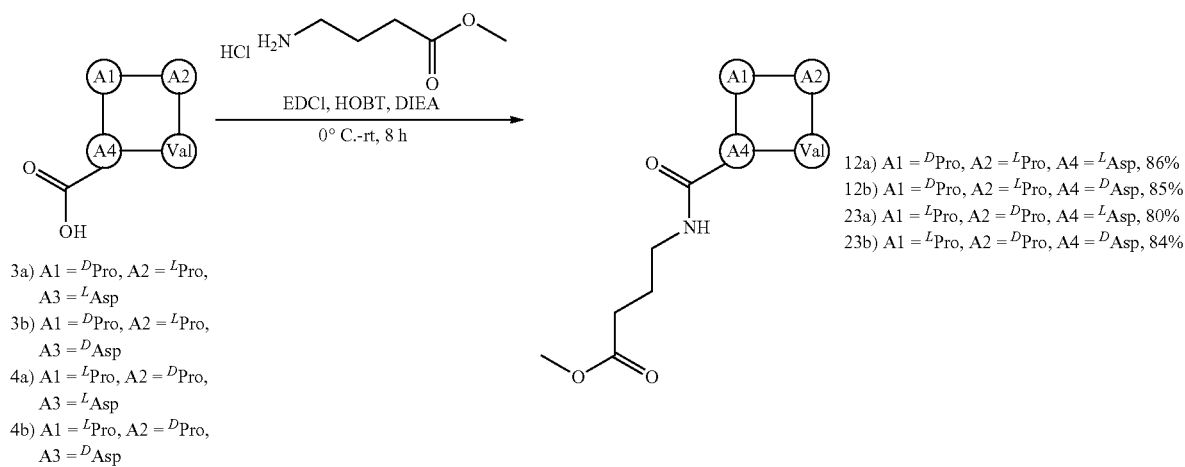

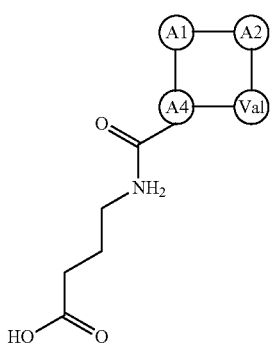

13a) A1 = $^D$Pro, A2 = $^L$Pro, A4 = $^L$Asp, 94%
13b) A1 = $^D$Pro, A2 = $^L$Pro, A4 = $^D$Asp, 95%
24a) A1 = $^L$Pro, A2 = $^D$Pro, A4 = $^L$Asp, 93%
24b) A1 = $^L$Pro, A2 = $^D$Pro, A4 = $^D$Asp, 95%

(1) LiOH, MeOH
H$_2$O, rt, 3 h
(2) 1N HCl, 0 C.-rt,
10 min, pH 2

NH$_2$OH HCl (10 eq.),
0.1N KOH (12 eq.)
MeOH—H$_2$O (3:1)
0 C.-rt, 0.5 h

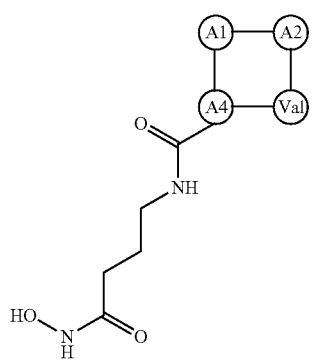

14a) A1 = $^D$Pro, A2 = $^L$Pro, A4 = $^L$Asp, 87%
14b) A1 = $^D$Pro, A2 = $^L$Pro, A4 = $^D$Asp, 85%
25a) A1 = $^L$Pro, A2 = $^D$Pro, A4 = $^L$Asp, 86%
25b) A1 = $^L$Pro, A2 = $^D$Pro, A4 = $^D$Asp, 87%

General Procedure for LiOH Base-Mediated Hydrolysis of Methyl Ester (13a, 13b, 24a, and 24b)

To a stirred solution of lithium hydroxide (1.5 mmol) in of distilled water (1 mL) was added to the methyl ester (1 mmol) in MeOH (3 mL) and then stirred at room temperature for 3.5 hours, then MeOH was removed under reduced pressure and acidified with 1 N HCl until pH was between 2 and 3 at 0° C. Then extracted with EtOAc, dried over anhydrous sodium sulfate (Na$_2$SO$_4$), and concentrated to give the desired acid, which was used further without purification.

General Procedure for Synthesis of Hydroxamic Acids from Corresponding Methyl Esters (14a, 14b, 25a, and 25b)

To a stirred solution of methyl ester (1 mmol) in MeOH (3 mL), hydroxylamine hydrochloride (10 mmol) was added followed by 0.1 N potassium hydroxide (12 mmol) in distilled water (1 mL) and then stirred at room temperature for 30 minutes, then MeOH was removed under reduced pressure and acidified with 1 N HCl until pH was between 2 and 3 at 0° C. The solution was extracted with EtOAc, dried over anhydrous sodium sulfate (Na$_2$SO$_4$), and concentrated to give the desired hydroxamic acid in high yield, which was further purified by HPLC.

General Procedure for Sulfoxide Synthesis from Organic Sulfides by H$_2$O$_2$/Borax (8a, 8b, 20a, and 20b)

In a typical experiment to a 25 mL flask equipped with a magnetic stirrer and 30% H2O2 (6.0 mmol) in water was added borax (0.2 mmol) and MeOH (5 mL), followed by methyl thioether containing peptide (1 mmol). The reaction was monitored by TLC. After complete disappearance of the reactant added Na$_2$S$_2$O$_5$ to destroy the excess amount of H$_2$O$_2$ and then removed MeOH, the product was extracted with EtOAc, dried over anhydrous sodium sulfate (Na$_2$SO$_4$), and concentrated to give a desired sulfoxide, which was purified by reverse phase HPLC.

General Procedure for Sulfones Synthesis from Organic Sulfides by H$_2$O$_2$/Borax (9a, 9b, 21a, and 21b)

In a typical experiment to a 25 mL flask equipped with a magnetic stirrer and 30% H2O2 (6.0 mmol) was added borax (0.2 mmol) and MeOH (5 mL), followed by methyl thioether containing peptide (1 mmol). To the resulting solution was added 0.1 N NaOH to maintain the pH of the solution at 10, and the mixture was stirred at room temperature for 12-15 hours and monitored by LC-MS. After complete disappearance of the reactant added Na$_2$S$_2$O$_5$ to destroy the excess amount of H$_2$O$_2$ and then removed MeOH, the product was extracted with EtOAc, dried over anhydrous sodium sulfate (Na$_2$SO$_4$), and concentrated to give a desired sulfone, which was purified by reverse phase HPLC.

General Procedure for Synthesis of Sulfhydryl from Corresponding Homodimer (5a, 5b, 6a, 6b, 17a, 17a, 18a, and 18b)

To a stirred solution of disulfide containing homodimer of SLA analogue (1 mmol) in DMSO-water (1:1) (4 mL), dithiothreitol (DTT) (20 mmol) was added followed by 0.1 N sodium hydroxide (0.01 mL) in distilled water and then stirred at room temperature for 2 hours. Then which was further purified by HPLC using 10-40 acetonitrile gradient over 30 minutes.

Cyclo-Asp($^D$Pro-Pro-Val)-OBn (1a)

Cyclic tetrapeptide 1a was synthesized by following the above general procedure for DPPA macrolactamization and purified by silica gel column chromatography (EtOAc) as a white solid (yield, 79%; purity by LC-MS, 99%). $^1$H NMR (400 MHz, CDCl$_3$) δ ppm: 7.50-7.41 (m, 2H), 7.41-7.28 (m, 3H), 7.03 (d, J=9.4 Hz, 1H), 6.48 (d, J=9.8 Hz, 1H), 5.28 (d, J=11.7 Hz, 1H), 5.19 (d, J=12.1 Hz, 1H), 5.12 (t, J=9.6 Hz, 1H), 4.58 (dd, J=3.6, 9.0 Hz, 1H), 4.56 (t, J=7.0 Hz, 1H), 4.45 (dd, J=3.9, 9.0 Hz, 1H), 4.18-4.09 (m, 1H), 3.63-3.54 (m, 1H), 3.31-3.22 (m, 1H), 3.12 (d, J=12.9 Hz, 1H), 3.01 (dt, J=5.7, 9.7 Hz, 1H), 2.79 (dd, J=9.8, 12.5 Hz, 1H), 2.53 (dt, J=3.3, 6.7 Hz, 1H), 2.41-2.29 (m, 1H), 2.17-2.02 (m, 4H), 1.93-1.79 (m, 2H), 1.76-1.63 (m, 1H), 0.93 (d, J=7.0

Hz, 3H), 0.89 (d, J=6.7 Hz, 3H). $^{13}$C NMR (100 MHz, CDCl$_3$) δ ppm: 173.7, 171.3, 171.1, 170.7, 169.9, 134.9, 129.2, 128.6, 128.5, 67.8, 62.6, 58.2, 56.0, 49.5, 47.8, 47.2, 35.8, 29.9, 29.1, 28.0, 26.1, 24.9, 20.2, 17.0. MS (ESI): found [M+H]+, 499.4.

Cyclo-$^D$Asp($^D$Pro-Pro-Val)-OBn (1b)

Cyclic tetrapeptide 1b was synthesized by following the above general procedure for DPPA macrolactamisation and purified by silica gel column chromatography (EtOAc) as a white solid (yield, 78%; purity by LC-MS, 99%). $^1$H NMR (400 MHz, CDCl$_3$) δ ppm: 7.42-7.28 (m, 5H), 7.09 (d, J=9.0 Hz, 1H), 6.51 (d, J=6.3 Hz, 1H), 5.24 (d, J=12.1 Hz, 1H), 5.14 (d, J=12.5 Hz, 1H), 4.69 (t, J=6.5 Hz, 1H), 4.52 (dd, J=4.1, 9.6 Hz, 1H), 4.48 (dd, J=4.3, 8.6 Hz, 1H), 4.28-4.14 (m, 2H), 3.99 (td, J=5.7, 11.6 Hz, 1H), 3.66-3.62 (m, 2H), 3.07 (t, J=12.3 Hz, 1H), 2.95 (dd, J=5.3, 12.7 Hz, 1H), 2.45-2.36 (m, 2H), 2.29-2.20 (m, 2H), 2.14-2.02 (m, 5H), 0.92 (d, J=5.1 Hz, 3H), 0.91 (d, J=5.1 Hz, 3H). $^{13}$C NMR (100 MHz, CDCl$_3$) δ ppm: 174.2, 172.4, 171.7, 171.5, 169.5, 135.4, 128.5, 128.4, 128.3, 67.5, 62.5, 58.2, 56.0, 50.4, 47.7, 47.5, 35.2, 29.7, 28.5, 28.0, 25.9, 24.9, 20.1, 17.0. MS (ESI): found [M+H]+, 499.4.

Cyclo-Asp($^D$Pro-Pro-Val)-OH (3a)

Cyclic tetrapeptide pendent carboxylic acid 3a was synthesized from 1a by following the above general procedure for catalytic hydrogenation of benzyl ester, obtained the desired pendent carboxylic acid as a white solid (yield, 96%; purity by LC-MS, >99%). $^1$H NMR (400 MHz, CDCl$_3$) δ ppm: 7.34 (bs, 1H), 7.21 (d, J=8.6 Hz, 1H), 6.53 (d, J=9.0 Hz, 1H), 5.03 (t, J=8.0 Hz, 1H), 4.63 (t, J=7.4 Hz, 1H), 4.48 (dd, J=4.7, 8.6 Hz, 1H), 4.44 (dd, J=4.7, 8.6 Hz, 1H), 4.24-4.15 (m, 1H), 3.71-3.52 (m, 3H), 3.22 (dd, J=2.1, 13.2 Hz, 1H), 2.90 (dd, J=9.0, 13.3 Hz, 1H), 2.51-2.33 (m, 2H), 2.24-1.96 (m, 6H), 1.89 (d, J=10.6 Hz, 1H), 0.94 (d, J=6.7 Hz, 3H), 0.90 (d, J=6.7 Hz, 3H). $^{13}$C NMR (100 MHz, CDCl$_3$) δ ppm: 174.0, 172.7, 172.5, 170.7, 170.3, 62.6, 58.4, 56.7, 49.5, 48.2, 47.4, 35.5, 29.7, 29.1, 27.9, 26.2, 24.9, 20.0, 17.2. MS (ESI): found [M+H]+, 409.4.

Cyclo-$^D$Asp($^D$Pro-Pro-Val)-OH (3b)

Cyclic tetrapeptide pendent carboxylic acid 3b was synthesized from 1b by following the above general procedure for catalytic hydrogenation of benzyl ester, obtained the desired pendent carboxylic acid as a white solid (yield, 94%; purity by LC-MS, >99%). $^1$H NMR (400 MHz, CDCl$_3$) δ ppm: 7.13 (d, J=9.4 Hz, 1H), 6.64 (d, J=5.9 Hz, 1H), 6.35 (bs, 1H), 4.69 (t, J=6.5 Hz, 1H), 4.56 (dd, J=3.9, 9.0 Hz, 1H), 4.48 (dd, J=4.7, 8.2 Hz, 1H), 4.24-4.08 (m, 2H), 3.76-3.68 (m, 2H), 3.67-3.60 (m, 1H), 2.46-2.34 (m, 2H), 2.34-2.18 (m, 2H), 2.17-2.10 (m, 2H), 2.10-1.99 (m, 3H), 0.93 (d, J=6.7 Hz, 3H), 0.92 (d, J=6.5 Hz, 3H). $^{13}$C NMR (100 MHz, CDCl$_3$) δ ppm: 174.8, 174.1, 172.3, 170.9, 62.5, 58.4, 56.2, 53.2, 47.8, 47.5, 35.3, 29.7, 28.4, 28.0, 25.9, 25.0, 20.1, 17.0. MS (ESI): found [M+H]+, 409.4.

Homodimer: [Cyclo-Asp($^D$Pro-Pro-Val)-NHCH$_2$CH$_2$S]$_2$ (35a)

The homodimer prodrug thioether 35a was synthesized from 3a by following the above general procedure for EDCl peptide coupling of pendent carboxylic acid with cysteamine diamine and purified by HPLC using 11-47% acetonitrile gradient, obtaining the deshomodimer as a white solid (yield, 82%; purity by LC-MS, >99%). $^1$H NMR (400 MHz, CDCl$_3$) δ ppm: 7.24 (t, J=5.9 Hz, 1H), 7.18 (d, J=9.4 Hz, 1H), 6.50 (d, J=10.2 Hz, 1H), 5.04 (t, J=9.0 Hz, 1H), 4.62 (t, J=6.8 Hz, 1H), 4.60 (dd, J=3.7, 9.0 Hz, 1H), 4.44 (dd, J=5.5, 8.6 Hz, 1H), 4.14 (td, J=6.7, 9.8 Hz, 1H), 3.70-3.56 (m, 4H), 3.49 (dd, J=2.0, 12.9 Hz, 1H), 2.81 (dt, J=1.6, 6.8 Hz, 2H), 2.63 (dd, J=9.4, 12.9 Hz, 1H), 2.57 (dd, J=3.7, 6.8 Hz, 1H), 2.48-2.35 (m, 1H), 2.22-2.09 (m, 4H), 2.09-2.00 (m, 1H), 2.00-1.83 (m, 2H), 0.92 (d, J=7.0 Hz, 3H), 0.88 (d, J=6.7 Hz, 3H). $^{13}$C NMR (100 MHz, CDCl$_3$) δ ppm: $^{13}$C NMR (101 MHz, CDCl$_3$) δ=174.6, 172.8, 172.2, 171.1, 170.8, 77.3, 77.0, 76.7, 62.7, 58.5, 56.8, 50.8, 48.3, 47.4, 39.3, 37.0, 34.9, 29.8, 29.0, 28.0, 26.0, 25.0, 19.8, 16.8. MS (ESI): found [M+Na]+, 955.7.

Cyclo-Asp($^D$Pro-Pro-Val)-NHCH$_2$CH$_2$SH (5a)

Thiol warhead having SLA analogue 5a was synthesized from 35a by following the above general procedure for synthesis of sulfhydryl from corresponding homodimer, obtaining the desired pendent thiol as a white solid (yield, 87%; purity by LC-MS, >99%). $^1$H NMR (400 MHz, CDCl$_3$) δ ppm: 7.31 (d, J=9.4 Hz, 1H), 7.08 (t, J=5.7 Hz, 1H), 6.46 (d, J=10.6 Hz, 1H), 5.04 (t, J=9.8 Hz, 1H), 4.67 (dd, J=3.1, 9.8 Hz, 1H), 4.63 (t, J=7.2 Hz, 1H), 4.48 (dd, J=5.3, 8.8 Hz, 1H), 4.15 (td, J=6.7, 9.8 Hz, 1H), 3.74-3.56 (m, 5H), 3.35 (qd, J=6.6, 13.1 Hz, 1H), 2.75-2.61 (m, 2H), 2.61-2.54 (m, 1H), 2.44 (td, J=7.9, 12.8 Hz, 1H), 2.24-2.01 (m, 6H), 1.97-1.87 (m, 2H), 1.84 (t, J=8.8 Hz, 1H), 0.93 (d, J=7.0 Hz, 3H), 0.89 (d, J=7.0 Hz, 3H). MS (ESI): found [M+H]+, 468.4.

Homodimer: [Cyclo-$^D$Asp($^D$Pro-Pro-Val)-NHCH$_2$CH$_2$S]$_2$ (35b)

The homodimer prodrug thioether 35b was synthesized from 3b by following the above general procedure for EDCl peptide coupling of pendent carboxylic acid with cysteamine diamine and purified by HPLC using 11-47% acetonitrile gradient, obtaining the desired homodimer as a white solid (yield, 78%; purity by LC-MS, 98%). $^1$H NMR (400 MHz, CDCl$_3$) δ ppm: 7.41 (t, J=4.9 Hz, 1H), 7.11 (d, J 10.2 Hz, 1H), 6.53 (d, J=6.3 Hz, 1H), 4.65 (t, J=6.8 Hz, 1H), 4.45 (t, J=5.2 Hz, 1H), 4.42 (t, J=4.6 Hz, 1H), 4.17 (td, J=6.3, 9.7 Hz, 1H), 4.10-4.01 (m, 1H), 3.68 (t, J=6.5 Hz, 2H), 3.65-3.44 (m, 3H), 3.05 (dd, J=3.9, 12.5 Hz, 1H), 2.92 (t, J=12.5 Hz, 1H), 2.85-2.65 (m, 2H), 2.42-2.19 (m, 3H), 2.19-1.90 (m, 6H), 0.93 (d, J=6.7 Hz, 3H), 0.91 (d, J=6.8 Hz, 3H). $^{13}$C NMR (100 MHz, CDCl$_3$) δ ppm: 173.8, 172.7, 172.5, 172.1, 170.0, 62.5, 58.2, 57.0, 52.5, 47.8, 47.4, 38.6, 37.5, 34.5, 29.7, 28.7, 28.1, 25.9, 24.9, 20.1, 17.4. MS (ESI): found [M+Na]+, 955.7.

Cyclo-$^D$Asp($^D$Pro-Pro-Val)-NHCH$_2$CH$_2$SH (5b)

Thiol warhead having SLA analogue 5b was synthesized from 35b by following the above general procedure for synthesis of sulfhydryl from corresponding homodimer, obtaining the desired pendent thiol as a white solid (yield, 80%; purity by LC-MS, >99%). $^1$H NMR (400 MHz, CDCl$_3$) δ ppm: 7.26 (bs, 1H), 7.17 (d, J=9.4 Hz, 1H), 6.43 (d, J=6.3 Hz, 1H), 4.73-4.64 (m, 1H), 4.54 (dd, J=4.1, 9.6 Hz, 1H), 4.46 (dd, J=4.1, 8.4 Hz, 1H), 4.15 (t, J=6.5 Hz, 1H), 4.02-3.95 (m, 1H), 3.74-3.50 (m, 5H), 3.32 (dd, J=6.8, 13.1 Hz, 1H), 3.08 (dd, J=4.3, 12.5 Hz, 1H), 2.95 (t, J=12.3 Hz, 1H), 2.74-2.60 (m, 2H), 2.38 (dt, J=3.5, 7.0 Hz, 2H), 2.22-2.15 (m, 2H), 2.14-2.05 (m 4H), 1.50 (t, J=8.6 Hz, 1H), 0.94 (d, J=3.1 Hz, 3H), 0.92 (d, J=3.1 Hz, 3H). MS (ESI): found [M+H]+, 468.4.

Homodimer: [Cyclo-Asp($^D$Pro-Pro-Val)-NHCH$_2$CH$_2$CH$_2$S]$_2$ Prodrug (37a)

The homodimer prodrug thioether 37a was synthesized 3a by following the above general procedure for EDCl peptide coupling of pendent carboxylic acid with cysteamine diamine and purified by HPLC using 11-47% acetonitrile gradient, obtaining the desired homodimer as a white solid (yield, 65%; purity by LC-MS, >99%). $^1$H NMR (400 MHz, CDCl$_3$) δ ppm: 7.09 (bs, 1H), 7.00 (d, J=8.6 Hz, 1H), 6.38 (d, J=5.0 Hz, 1H), 4.58 (t, J=6.7 Hz, 1H), 4.37 (dd, J=5.1, 8.2 Hz, 1H), 4.34 (dd, J=4.7, 8.2 Hz, 1H), 4.14-4.05 (m, 1H), 4.03-3.91 (m, 1H), 3.66-3.50 (m, 3H), 3.39-3.20 (m, 2H), 2.97 (dd, J=3.9, 12.5 Hz, 1H), 2.81 (t, J=12.5 Hz, 1H), 2.63 (t, J=6.8 Hz, 2H), 2.35-2.21 (m, 2H), 2.17 (dd, J=5.3, 10.8 Hz, 1H), 2.13-2.06 (m, 1H), 2.06-1.99 (m, 1H), 1.99-1.87 (m, 2H), 1.85-1.81 (m, 2H), 1.83 (td, J=6.6, 13.0 Hz, 2H), 0.85 (d, J=3.9 Hz, 3H), 0.84 (d, J=3.9 Hz, 3H). $^{13}$C NMR (100 MHz, CDCl$_3$) δ ppm: 174.2 173.2, 172.5, 172.2, 170.9, 65.5, 62.6, 58.4, 56.7, 53.0, 47.8, 47.5, 36.6, 34.4, 31.6, 29.7, 28.5, 28.1, 25.9, 25.0, 20.1, 17. MS (ESI): found [M+H]+, 961.8.

Cyclo-Asp($^D$Pro-Pro-Val)-NHCH$_2$CH$_2$CH$_2$SH (6a)

Thiol warhead having SLA analogue 6a was synthesized from 37a by following the above general procedure for synthesis of sulfhydryl from corresponding homodimer, obtaining the desired pendent thiol as a white solid (yield, 79%; purity by LC-MS, >99%). $^1$H NMR (400 MHz, CDCl$_3$) δ ppm: 7.31 (d, J=9.0 Hz, 1H), 7.15 (bs, 1H), 6.58 (d, J=10.2 Hz, 1H), 5.11-5.00 (m, 1H), 4.64 (t, J=7.2 Hz, 1H), 4.56 (dd, J=3.7, 9.2 Hz, 1H), 4.48 (dd, J=5.7, 8.4 Hz, 1H), 4.14 (td, J=7.0, 9.9 Hz, 1H), 3.73-3.55 (m, 3H), 3.54-3.41 (m, 2H), 3.36 (td, J=6.5, 13.2 Hz, 1H), 2.67 (dd, J=8.8, 13.1 Hz, 1H), 2.57 (q, J=7.2 Hz, 3H), 2.50-2.40 (m, 1H), 2.25-2.12 (m, 4H), 2.07 (td, J=6.2, 12.7 Hz, 1H), 1.99-1.92 (m, 2H), 1.89-1.79 (m, 2H), 1.43 (t, J=8.0 Hz, 1H), 0.92 (d, J=6.7 Hz, 3H), 0.90-0.86 (d, J=6.7 Hz, 3H). MS (ESI): found [M+H]+, 482.4.

Homodimer: [Cyclo-$^D$Asp($^D$Pro-Pro-Val)-NHCH$_2$CH$_2$CH$_2$S]$_2$ Prodrug (37b)

The homodimer prodrug thioether 37b was synthesized from 3b by following the above general procedure for EDCl peptide coupling of pendent carboxylic acid with cysteamine diamine and purified by HPLC using 11-47% acetonitrile gradient, obtaining the desired homodimer as a white solid (yield, 67%; purity by LC-MS, 99%). $^1$H NMR (400 MHz, CDCl$_3$) δ ppm: 7.07 (d, J=9.4 Hz, 1H), 6.72 (t, J=5.3 Hz, 1H), 6.34 (d, J=11.2 Hz, 1H), 4.91 (t, J=9.6 Hz, 1H), 4.58 (dd, J=2.7, 9.8 Hz, 1H), 4.53 (t, J=6.8 Hz, 1H), 4.34 (dd, J=4.9, 8.8 Hz, 1H), 4.11-4.02 (m, 1H), 3.62-3.38 (m, 6H), 3.26-3.14 (m, 1H), 2.64 (dt, J=2.3, 7.0 Hz, 2H), 2.54 (dt, J=2.9, 6.6 Hz, 1H), 2.46 (dd, J=9.4, 12.5 Hz, 1H), 2.37-2.28 (m, 1H), 2.08-2.02 (m, 4H), 2.02-1.93 (m, 2H), 1.84 (p, J=6.8 Hz, 12H), 1.82-1.75 (m, 1H), 0.84 (d, J=6.7 Hz, 3H), 0.80 (d, J=6.7 Hz, 3H). MS (ESI): found [M+H]+, 961.8.

Cyclo-$^D$Asp($^D$Pro-Pro-Val)-NHCH$_2$CH$_2$CH$_2$SH (6b)

Thiol warhead having SLA analogue 6b was synthesized from 37b by following the above general procedure for synthesis of sulfhydryl from corresponding homodimer, obtaining the desired pendent thiol as a white solid (yield, 85%; purity by LC-MS, >99%). $^1$H NMR (400 MHz, CDCl$_3$) δ ppm: 7.28 (d, J=7.4 Hz, 1H), 6.62 (bs, 1H), 6.51 (d, J=6.3 Hz, 1H), 4.72-4.65 (m, 1H), 4.51 (dd, J=4.3, 8.2 Hz, 1H), 4.47 (dd, J=5.0, 9.2 Hz, 1H), 4.17 (td, J=6.6, 9.9 Hz, 2H), 4.04-3.96 (m, 2H), 3.72-3.61 (m, 3H), 3.45 (td, J=6.7, 13.3 Hz, 1H), 3.37 (td, J=6.6, 13.0 Hz, 1H), 3.07 (dd, J=4.7, 12.5 Hz, 1H), 2.96 (t, J=12.5 Hz, 1H), 2.55 (d, J=7.8 Hz, 1H), 2.59-2.52 (m, 1H), 2.47-2.18 (m, 4H), 2.17-2.02 (m, 4H), 1.87-1.78 (m, 2H), 1.44 (t, J=8.0 Hz, 1H), 0.94 (d, J=6.9 Hz, 3H), 0.92 (d, J=6.7 Hz, 3H); MS (ESI): found [M+H]+, 482.4.

Cyclo-Asp($^D$Pro-Pro-Val)-NHCH$_2$CH$_2$CH$_2$SCH$_3$ (7a)

The cyclic peptide 7a having the methylthioether warhead on pendent carboxylic acid was synthesized from 3a by following the above general procedure for EDCl peptide coupling of pendent carboxylic acid with 3-(methylthio)propan-1-amine and purified by HPLC using 5-55% acetonitrile gradient, obtaining the desired peptide as a white solid (yield, 68%; purity by LC-MS, >99%). $^1$H NMR (400 MHz, CDCl$_3$) δ ppm: 7.17 (d, J=9.4 Hz, 1H), 6.78 (t, J=6.4 Hz, 1H), 6.41 (d, J=10.6 Hz, 1H), 5.00 (t, J=10.0 Hz, 1H), 4.66 (dd, J=3.1, 9.4 Hz, 1H), 4.61 (t, J=6.7 Hz, 1H), 4.44 (dd, J=4.9, 8.4 Hz, 1H), 4.20-4.11 (m, 1H), 3.70-3.60 (m, 3H), 3.57 (d, J=12.5 Hz, 1H), 3.48 (dt, J=6.7, 13.3 Hz, 1H), 3.33 (dt, J=6.7, 12.9 Hz, 1H), 2.63 (dt, J=2.9, 6.9 Hz, 1H), 2.60-2.49 (m, 2H), 2.47-2.35 (m, 1H), 2.21-2.11 (m, 3H), 2.08 (s, 3H), 2.07-1.99 (m, 1H), 1.98-1.88 (m, 2H), 1.83 (quin, J=7.0 Hz, 2H), 0.92 (d, J=6.7 Hz, 3H), 0.89 (d, J=6.7 Hz, 3H). $^{13}$C NMR (100 MHz, CDCl$_3$) δ ppm: 174.8, 172.5, 172.2, 171.3, 170.3, 62.8, 58.6, 56.5, 51.1, 48.4, 47.4, 39.1, 34.8, 31.2, 29.9, 29.0, 28.3, 28.1, 26.1, 25.0, 20.0, 16.8, 15.3. MS (ESI): found: [M+Na]+, 518.8.

Cyclo-$^D$Asp($^D$Pro-Pro-Val)-NHCH$_2$CH$_2$CH$_2$SCH$_3$ (7b)

The cyclic peptide 7b having the methylthioether warhead on pendent carboxylic acid was synthesized from 3b by following the above general procedure for EDCl peptide coupling of pendent carboxylic acid with 3-(methylthio)propan-1-amine and purified by HPLC using 5-55% acetonitrile gradient, obtaining the desired peptide as a white solid (yield, 65%; purity by LC-MS, 98%). $^1$H NMR (400 MHz, CDCl$_3$) δ ppm: 7.15 (d, J=9.4 Hz, 1H), 7.08 (t, J=6.4 Hz, 1H), 6.41 (d, J=6.3 Hz, 1H), 4.67 (t, J=9.8 Hz, 1H), 4.49 (dd, J=3.2, 9.2 Hz, 1H), 4.45 (dd, J=4.8, 8.7 Hz, 1H), 4.17 (td, J=6.3, 9.8 Hz, 1H), 3.97 (td, J=5.5, 11.2 Hz, 1H), 3.68 (t, J=6.4 Hz, 2H), 3.67-3.59 (m, 1H), 3.45-3.28 (m, 2H), 3.06 (dd, J=4.1, 12.7 Hz, 1H), 2.92 (t, J=12.5 Hz, 1H), 2.51 (t, J=7.2 Hz, 2H), 2.43-2.30 (m, 2H), 2.29-2.17 (m, 2H), 2.16-2.10 (m, 2H), 2.09 (s, 3H), 2.06-1.95 (m, 3H), 1.81 (dp, J=2.2, 7.0 Hz, 2H), 0.94 (d, J=3.5 Hz, 3H), 0.92 (d, J=3.1 Hz, 3H). $^{13}$C NMR (100 MHz, CDCl$_3$) δ ppm: 174.1, 173.2, 172.3, 172.1, 169.6, 62.6, 58.3, 56.6, 53.3, 47.8, 47.4, 38.7, 34.4, 31.4, 29.7, 28.6, 28.3, 28.1, 25.9, 24.9, 20.1, 17.2, 15.4. MS (ESI): found [M+H]+, 496.4.

Cyclo-Asp($^D$Pro-Pro-Val)-NHCH$_2$CH$_2$CH$_2$S(=O)CH$_3$ (8a)

The cyclic peptide 8a having the methylsulfoxide warhead on pendent carboxylic acid was synthesized from 7a by following the above general procedure for sulfoxide synthesis from organic sulfides by $H_2O_2$/borax and purified by HPLC using 5-50% acetonitrile gradient, obtaining the desired sulfoxide as a white solid (yield, 69%; purity by LC-MS, >99%). Nonseparable diastereomeric mixture=1.1:1. $^1$H NMR (400 MHz, CDCl$_3$) δ ppm: 7.20 (d, J=7.0 Hz, 1H), 7.18 (d, J=7.2 Hz, 1H), 6.97 (t, J=5.9 Hz, 1H), 6.95 (t, J=5.6 Hz, 1H), 6.37 (d, J=10.6 Hz, 1H), 6.31 (d, J=10.6 Hz, 1H), 4.98 (t, J=9.8 Hz, 2H), 4.65 (dd, J=3.1, 9.8 Hz, 2H), 4.61 (t, J=7.0 Hz, 2H), 4.42 (dd, J=4.7, 8.2 Hz, 1H), 4.39 (dd, J=4.5, 7.9 Hz, 1H), 4.20-4.09 (m, 2H), 3.73-3.54 (m, 8H), 3.38-3.21 (m, 2H), 2.91 (t, J=8.1 Hz, 2H), 2.81 (t, J=8.1 Hz, 2H), 2.67 (s, 3H), 2.65 (s, 3H), 2.64-2.59 (m, 2H), 2.53 (ddd, J=2.3, 9.6, 12.3 Hz, 2H), 2.47-2.35 (m, 2H), 2.20-2.09 (m, 9H), 2.09-2.00 (m, 7H), 1.98-1.83 (m, 4H), 0.92 (d, J=7.0 Hz, 6H), 0.89 (d, J=6.9 Hz, 6H). $^{13}$C NMR (100 MHz, CDCl$_3$) δ ppm: 175.0, 175.0, 172.4, 172.3, 172.3, 171.1, 170.6, 170.5, 62.8, 62.8, 58.6, 56.5, 53.4, 51.0, 50.7, 50.3, 48.5, 47.4, 38.4, 37.6, 34.4, 34.3, 31.6, 29.9, 28.8, 28.1, 28.0, 26.1, 25.0, 22.8, 22.6, 19.9, 16.7. MS (ESI): found [M+H]+, 512.4.

Cyclo-$^D$Asp($^D$Pro-Pro-Val)-NHCH$_2$CH$_2$CH$_2$S(=O)CH$_3$ (8b)

The cyclic peptide 8b having the methylsulfoxide warhead on pendent carboxylic acid was synthesized from 7b by following the above general procedure for sulfoxide synthesis from organic sulfides by $H_2O_2$/borax and purified by HPLC using 5-50% acetonitrile gradient, obtaining the desired sulfoxide as a white solid (yield, 65%; purity by LC-MS, 98%). Nonseparable diastereomeric mixture=1:1. $^1$H NMR (400 MHz, CDCl$_3$) δ ppm: 7.12 (d, J=7.0 Hz, 1H), 6.87 (bs, 1H), 6.41 (bs, 1H), 4.69 (t, J=6.7 Hz, 1H), 4.53 (td, J=3.2, 9.3 Hz, 1H), 4.44 (dd, J=4.5, 8.8 Hz, 1H), 4.16 (td, J=6.4, 9.6 Hz, 1H), 3.93-3.84 (m, 1H), 3.72-3.52 (m, 4H), 3.38-3.22 (m, 1H), 3.06 (dd, J=3.9, 12.5 Hz, 1H), 2.91 (t, J=11.9 Hz, 1H), 2.86-2.70 (m, 2H), 2.62 (s, 1.5H), 2.61 (s, 1.5H), 2.46-2.30 (m, 2H), 2.29-2.17 (m, 1H), 2.16-1.91 (m, 6H), 1.87-1.70 (m, 2H), 0.93 (d, J=6.7 Hz, 3H), 0.92 (d, J=6.6 Hz, 3H). MS (ESI): found [M+Na]+, 512.4.

Cyclo-Asp($^D$Pro-Pro-Val)-NHCH$_2$CH$_2$CH$_2$S(=O)$_2$CH$_3$ (9a)

The cyclic peptide 9a having the methylsulfone warhead on pendent carboxylic acid was synthesized from 7a by following the above general procedure for sulfones synthesis from organic sulfides by $H_2O_2$/borax and purified by HPLC using 5-48% acetonitrile gradient over 30 minutes, obtaining the desired sulfone as a white solid (yield, 83%; purity by LC-MS, >99%). $^1$H NMR (400 MHz, CDCl$_3$) δ ppm: 7.19 (d, J=9.4 Hz, 1H), 6.89 (t, J=9.4 Hz, 1H), 6.35 (d, J=10.4 Hz, 1H), 4.98 (t, J=10.0 Hz, 1H), 4.66 (dd, J=2.9, 9.6 Hz, 1H), 4.61 (t, J=7.4 Hz, 1H), 4.39 (dd, J=5.1, 8.6 Hz, 1H), 4.15 (td, J=6.7, 10.0 Hz, 1H), 3.76 (dd, J=5.5, 13.7 Hz, 1H), 3.69-3.58 (m, 2H), 3.34-3.23 (m, 1H), 3.23-3.11 (m, 2H), 3.11-2.93 (m, 2H), 2.90 (s, 3H), 2.63 (dt, J=3.1, 6.8 Hz, 1H), 2.52 (dd, J=9.6, 12.3 Hz, 1H), 2.46-2.35 (m, 1H), 2.21-2.10 (m, 3H), 2.10-1.95 (m, 2H), 1.95-1.83 (m, 1H), 0.92 (d, J=7.0 Hz, 3H), 0.89 (d, J=6.7 Hz, 3H). NMR (100 MHz, CDCl$_3$) δ ppm: 175.2, 172.4, 172.2, 171.1, 170.5, 62.8, 58.7, 56.5, 51.6, 51.0, 48.6, 47.4, 40.4, 37.9, 34.2, 29.9, 28.8, 28.0, 26.1, 25.0, 22.5, 19.9, 16.7. MS (ESI): found [M+H]+, 528.4.

Cyclo-$^D$Asp($^D$Pro-Pro-Val)-NHCH$_2$CH$_2$CH$_2$S(=O)$_2$CH$_3$ (9b)

The cyclic peptide 9b having the methylsulfone warhead on pendent carboxylic acid was synthesized from 7b by following the above general procedure for sulfones synthesis from organic sulfides by $H_2O_2$/borax and purified by HPLC using 5-48% acetonitrile gradient over 30 minutes, obtaining the desired sulfone as a white solid (yield, 85%; purity by LC-MS, 97%). $^1$H NMR (400 MHz, CDCl$_3$) δ ppm: 7.11 (d, J=9.4 Hz, 1H), 6.78 (t, J=4.7 Hz, 1H), 6.44 (d, J=6.3 Hz, 1H), 4.69 (t, J=11.2 Hz, 1H), 4.54 (dd, J=3.7, 9.6 Hz, 1H), 4.43 (dd, J=4.5, 8.8 Hz, 1H), 4.15 (dd, J=6.8, 10.0 Hz, 1H), 3.93-3.83 (m, 1H), 3.71-3.54 (m, 4H), 3.31-3.19 (m, 2H), 3.10-3.01 (m, 2H), 2.93 (s, 3H), 2.88 (d, J=4.7 Hz, 1H), 2.44-2.30 (m, 2H), 2.26-1.97 (m, 6H), 1.91 (d, J=7.0 Hz, 1H), 0.93 (d, J=4.3 Hz, 3H), 0.91 (d, J=3.9 Hz, 3H). $^{13}$C NMR (100 MHz, CDCl$_3$) δ ppm: 174.5, 173.7, 172.6, 171.5, 169.7, 62.7, 58.4, 56.0, 53.0, 51.5, 47.8, 47.4, 40.8, 37.6, 34.3, 29.7, 28.5, 28.1, 26.0, 25.0, 22.5, 20.3, 17.0. MS (ESI): found [M+Na]+, 528.4.

Cyclo-$^D$Asp($^D$Pro-Pro-Val)-NHCH$_2$CH$_2$CH$_2$OH (10a)

The cyclic peptide 10a having the n-propylalcohol warhead on pendent carboxylic acid was synthesized from 3a by following the above general procedure for EDCl peptide coupling of pendent carboxylic acid with 3-aminopropan-1-ol and purified by HPLC using 11-40% acetonitrile gradient over 30 minutes, obtaining the desired alcohol as viscous oil (yield, 60%; purity by LC-MS, >97%). $^1$H NMR (400 MHz, CDCl$_3$) δ ppm: 7.18 (t, J=5.7 Hz, 1H), 7.04 (d, J=9.6 Hz, 1H), 6.28 (d, J=10.4 Hz, 1H), 4.98 (t, J=10.0 Hz, 1H), 4.68 (dd, J=2.9, 9.8 Hz, 1H), 4.63 (t, J=6.7 Hz, 1H), 4.42 (dd, J=4.8, 8.7 Hz, 1H), 4.16 (td, J=6.6, 9.9 Hz, 1H), 3.79-3.69 (m, 3H), 3.67-3.56 (m, 4H), 3.38-3.27 (m, 1H), 2.69-2.59 (m, 1H), 2.52 (dd, J=9.5, 12.4 Hz, 1H), 2.46-2.34 (m, 1H), 2.17-2.02 (m, 4H), 1.97-1.83 (m, 4H), 1.73-1.71 (m, 1H), 0.92 (d, J=6.8 Hz, 3H), 0.89 (d, J=6.8 Hz, 3H). $^{13}$C NMR (100 MHz, CDCl$_3$) δ ppm: 175.0, 172.5, 172.0, 171.1, 170.9, 62.8, 60.5, 58.6, 56.6, 50.7, 48.3, 47.4, 38.0, 34.5, 31.1, 29.8, 28.8, 28.1, 26.0, 25.0, 19.9, 16.7. MS (ESI): found [M+H]+, 466.4.

Cyclo-$^D$Asp($^D$Pro-Pro-Val)-NHCH$_2$CH$_2$CH$_2$OH (10b)

The cyclic peptide 10b having the n-propylalcohol warhead on pendent carboxylic acid was synthesized from 3b by following the above general procedure for EDCl peptide coupling of pendent carboxylic acid with 3-aminopropan-1-ol and purified by HPLC using 11-40% acetonitrile gradient over 30 minutes, obtaining the desired alcohol as viscous oil (yield, 75%; purity by LC-MS, >99%). $^1$H NMR (400 MHz, CDCl$_3$) δ ppm: 7.38-7.17 (m, 2H), 6.51 (bs, 1H), 4.78-4.67 (m, 1H), 4.62-4.39 (m, 2H), 4.32-4.15 (m, 1H), 4.15-3.96 (m, 1H), 3.84-3.67 (m, 3H), 3.67-3.47 (m, 1H), 3.44-3.24 (m, 1H), 3.24-3.05 (m, 1H), 3.05-2.92 (m, 1H), 2.54-2.35 (m, 2H), 2.35-2.23 (m, 2H), 2.20-2.13 (m, 2H), 2.13-1.92 (m, 3H), 1.91-1.64 (m, 2H), 1.22-0.95 (m, 6H). $^{13}$C NMR (100 MHz, CDCl$_3$) δ ppm: 174.2, 173.2, 172.5, 172.1, 170.9, 170.0, 65.4, 62.5, 58.4, 56.6, 53.0, 47.8, 47.4, 34.4, 31.6, 29.7, 28.4, 28.1, 28.0, 25.9, 24.9, 20.1, 17.1. MS (ESI): found [M+H]+, 466.4.

Cyclo-Asp($^D$Pro-Pro-Val)-NHCH$_2$CH$_2$S—SCH$_2$CH$_2$NHP(O)(OPh) (11a)

The cyclic peptide 11a having the phosphate warhead on pendent carboxylic acid was synthesized by following from 3a the above general procedure for DPPA peptide coupling of coupling of pendent carboxylic acid with cysteamine diamine and purified by HPLC using 11-35% acetonitrile gradient over 30 minutes, obtaining the desired peptide as a white solid (yield, 52%; purity by LC-MS, >99%). $^1$H NMR (400 MHz, CDCl$_3$) δ ppm: 7.39-7.30 (m, 4H), 7.28-7.22 (m, 8H), 7.22-7.14 (m, 2H), 7.09 (d, J=9.8 Hz, 1H), 7.03 (t, J=5.3 Hz, 1H), 6.46 (d, J=10.4 Hz, 1H), 5.00 (t, J=10.0 Hz, 1H), 4.64 (dd, J=3.1, 9.4 Hz, 1H), 4.60 (t, J=7.0 Hz, 1H), 4.38 (dd, J=5.1, 8.2 Hz, 1H), 4.15-4.06 (m, 1H), 3.70-3.48 (m, 5H), 3.47-3.35 (m, 2H), 2.83-2.72 (m, 4H), 2.61 (dt, J=3.5, 6.8 Hz, 1H), 2.55 (dd, J=9.6, 12.7 Hz, 1H), 2.39-2.26 (m, 1H), 2.17-2.03 (m, 4H), 2.03-1.91 (m, 2H), 1.87 (dd, J=8.0, 12.3 Hz, 1H), 0.91 (d, J=7.0 Hz, 3H), 0.88 (d, J=6.7 Hz, 3H). $^{13}$C NMR (100 MHz, CDCl$_3$) δ ppm: 174.9, 172.5, 172.1, 171.0, 170.6, 150.6, 129.8, 125.2, 120.8, 62.8, 58.5, 56.5, 50.9, 48.3, 47.5, 40.2, 39.9, 37.3, 34.7, 29.9, 29.7, 28.9, 28.0, 26.0, 25.0, 19.9, 16.8. MS (ESI): found [M+Na]+, 775.5.

Cyclo-$^D$Asp($^D$Pro-Pro-Val)-NHCH$_2$CH$_2$S—SCH$_2$CH$_2$NHP(O)(OPh) (11b)

The cyclic peptide 11b having the phosphate warhead on pendent carboxylic acid was synthesized from 3b by following the above general procedure for DPPA peptide coupling of coupling of pendent carboxylic acid with cysteamine diamine and purified by HPLC using 11-35% acetonitrile gradient over 30 minutes, obtaining the desired peptide as a white solid (yield, 56%; purity by LC-MS, >99%). $^1$H NMR (400 MHz, CDCl$_3$) δ ppm: 7.35 (t, J=8.0 Hz, 4H), 7.28-7.23 (m, 4H), 7.18 (t, J=7.2 Hz, 3H), 7.12 (d, J=9.4 Hz, 1H), 6.47 (d, J=6.3 Hz, 1H), 4.66 (t, J=6.7 Hz, 1H), 4.49 (dd, J=4.7, 9.4 Hz, 1H), 4.44 (dd, J=4.7, 8.6 Hz, 1H), 4.21-4.14 (m, 1H), 4.14-4.05 (m, 1H), 4.04-3.95 (m, 1H), 3.64 (t, J=6.8 Hz, 2H), 3.62-3.56 (m, 1H), 3.55-3.44 (m, 1H), 3.39 (dd, J=5.9, 12.1 Hz, 2H), 3.03 (dd, J=4.3, 12.5 Hz, 1H), 2.94-2.85 (m, 1H), 2.79-2.72 (m, 2H), 2.71 (t, J=6.6 Hz, 2H), 2.43-2.26 (m, 2H), 2.26-2.14 (m, 2H), 2.14-2.04 (m, 3H), 2.04-1.91 (m, 2H), 0.91 (d, J=6.7 Hz, 6H). $^{13}$C NMR (100 MHz, CDCl$_3$) δ ppm: 174.1, 173.3, 172.2, 169.8, 167.0, 150.5, 129.8, 125.2, 120.2, 120.2, 62.6, 58.3, 56.6, 53.0, 47.7, 47.4, 40.4, 39.7, 38.4, 37.2, 34.4, 29.7, 28.5, 28.1, 25.9, 24.9, 20.1, 17.1. MS (ESI): found: [M+Na]+, 775.5.

Cyclo-Asp($^D$Pro-Pro-Val)-NHCH$_2$CH$_2$CH$_2$COOMe (12a)

The cyclic peptide 12a having the methylcarboxylate warhead on pendent carboxylic acid was synthesized from 3a by following the above general procedure for EDCl peptide coupling of coupling of pendent carboxylic acid with methyl 4-aminobutanoate and purified by HPLC using 11-45% acetonitrile gradient over 30 minutes, obtaining the desired peptide as a white solid (yield, 86%; purity by LC-MS, >99%). $^1$H NMR (400 MHz, CDCl$_3$) δ ppm: 7.18 (d, J=9.4 Hz, 1H), 6.85 (t, J=4.7 Hz, 1H), 6.41 (d, J=10.2 Hz, 1H), 5.00 (t, J=9.8 Hz, 1H), 4.67 (dd, J=2.3, 9.4 Hz, 1H), 4.61 (t, J=6.7 Hz, 1H), 4.45 (dd, J=5.1, 8.2 Hz, 1H), 4.20-4.11 (m, 1H), 3.67 (s, 3H), 3.63 (t, J=7.1 Hz, 2H), 3.56 (d, J=12.9 Hz, 1H), 3.44-3.34 (m, 1H), 3.34-3.23 (m, 1H), 2.68-2.60 (m, 1H), 2.56 (dd, J=10.0, 12.3 Hz, 1H), 2.47-2.36 (m, 3H), 2.21-2.02 (m, 5H), 1.99-1.81 (m, 4H), 0.93 (d, J=7.0 Hz, 3H), 0.89 (d, J=6.7 Hz, 3H). $^{13}$C NMR (100 MHz, CDCl$_3$) δ ppm: 174.8, 173.6, 172.5, 172.3, 171.2, 170.4, 62.7, 58.6, 56.5, 51.7, 51.0, 48.3, 47.4, 39.4, 34.8, 31.2, 29.9, 28.9, 28.1, 26.0, 25.0, 24.4, 19.9, 16.8. MS (ESI): found [M+H]+, 508.5.

Cyclo-$^D$Asp($^D$Pro-Pro-Val)-NHCH$_2$CH$_2$CH$_2$COOMe (12b)

The cyclic peptide 12b having the methylcarboxylate warhead on pendent carboxylic acid was synthesized from 3b by following the above general procedure for EDCl peptide coupling of coupling of pendent carboxylic acid with methyl 4-aminobutanoate and purified by HPLC using 11-45% acetonitrile gradient over 30 minutes, obtaining the desired peptide as a white solid (yield, 85%; purity by LC-MS, >99%). $^1$H NMR (400 MHz, CDCl$_3$) δ ppm: 7.11 (d, J=9.4 Hz, 1H), 6.92 (t, J=5.3 Hz, 1H), 6.37 (d, J=6.3 Hz, 1H), 4.68 (t, J=6.7 Hz, 1H), 4.52 (dd, J=4.3, 9.4 Hz, 1H), 4.44 (dd, J=4.3, 8.6 Hz, 1H), 4.22-4.11 (m, 1H), 3.94-3.85 (m, 1H), 3.72-3.68 (m, 1H), 3.67 (s, 3H), 3.66-3.59 (m, 2H), 3.39-3.22 (m, 2H), 3.07 (dd, J=4.1, 12.7 Hz, 1H), 2.93 (t, J=12.5 Hz, 1H), 2.43-2.33 (m, 1H), 2.36 (t, J=6.9 Hz, 2H), 2.29-2.19 (m, 1H), 2.16-2.06 (m, 3H), 2.06-1.98 (m, 2H), 1.83 (p, J=7.6 Hz, 2H), 1.82-1.71 (m, 2H), 0.93 (d, J=6.9 Hz, 3H), 0.93 (d, J=6.8 Hz, 3H). $^{13}$C NMR (100 MHz, CDCl$_3$) δ ppm: 174.3, 173.7, 173.5, 172.5, 171.6, 169.4, 62.7, 58.3, 56.2, 53.4, 51.7, 47.8, 47.4, 39.0, 34.3, 31.2, 29.8, 28.5, 28.1, 25.9, 25.0, 24.6, 20.2, 17.1. MS (ESI): found [M+H]+, 508.5.

Cyclo-Asp($^D$Pro-Pro-Val)-NHCH$_2$CH$_2$CH$_2$COOH (13a)

The cyclic peptide 13a having the carboxylic acid warhead on pendent carboxylic acid was synthesized from 12a by following the above general procedure for general procedure for LiOH base mediated hydrolysis of methyl ester and purified by HPLC using 11-35% acetonitrile gradient over 30 minutes, obtaining the desired peptide as a white solid (yield, 94%; purity by LC-MS, >99%). $^1$H NMR (400 MHz, CDCl$_3$) δ ppm: 7.68 (t, J=4.9 Hz, 1H), 7.16 (d, J=9.4 Hz, 1H), 6.21 (d, J=10.2 Hz, 1H), 5.08 (bs, 1H), 4.98 (t, J=10.0 Hz, 1H), 4.76 (dd, J=3.1, 9.4 Hz, 1H), 4.60 (t, J=6.8 Hz, 1H), 4.40 (dd, J=5.1, 8.6 Hz, 1H), 4.21-4.05 (m, 1H), 3.78-3.69 (m, 1H), 3.68-3.57 (m, 2H), 3.42-3.25 (m, 2H), 2.67-2.58 (m, 1H), 2.58-2.49 (m, 2H), 2.42 (dd, J=6.5, 13.1 Hz, 2H), 2.22-1.99 (m, 5H), 1.99-1.78 (m, 4H), 0.93 (d, J=6.7 Hz, 3H), 0.89 (d, J=7.0 Hz, 3H). $^{13}$C NMR (100 MHz, CDCl$_3$) δ ppm: 177.0, 174.8, 173.6, 171.5, 171.2, 170.4, 63.0, 58.4, 56.7, 50.5, 48.4, 47.4, 40.9, 34.1, 31.8, 29.9, 28.8, 28.1, 26.0, 25.0, 22.5, 19.9, 16.8. MS (ESI): found [M+H]+, 494.4.

Cyclo-$^D$Asp($^D$Pro-Pro-Val)-NHCH$_2$CH$_2$CH$_2$COOH (13b)

The cyclic peptide 13b having the carboxylic acid warhead on pendent carboxylic acid was synthesized from 12b by following the above general procedure for general procedure for LiOH base mediated hydrolysis of methyl ester and purified by HPLC using 11-35% acetonitrile gradient over 30 minutes, obtaining the desired peptide as a white solid (yield, 95%; purity by LC-MS, >99%). $^1$H NMR (400 MHz, CDCl$_3$) δ ppm: 7.20 (bs, 1H), 7.12 (d, J=9.0 Hz, 1H), 6.50 (d, J=5.9 Hz, 1H), 4.92 (bs, 1H), 4.67 (t, J=6.5 Hz, 1H), 4.48 (dd, J=4.9, 9.6 Hz, 1H), 4.42 (dd, J=4.5, 8.0 Hz, 1H), 4.19 (q, J=9.4 Hz, 1H), 4.07-3.98 (m, 1H), 3.69 (t, J=6.1 Hz, 2H), 3.64 (q, J=8.5 Hz, 1H), 3.39 (dd, J=6.3, 13.3 Hz, 1H), 3.30 (dd, J=6.3, 12.9 Hz, 1H), 3.06 (dd, J=3.7, 12.3 Hz, 1H), 2.92 (t, J=12.4 Hz, 1H), 2.40 (t, J=6.7 Hz, 2H), 2.38-2.29 (m, 2H), 2.27 (d, J=5.1 Hz, 1H), 2.15-2.08 (m, 4H), 2.04-1.95 (m, 4H), 1.85 (quin, J=6.6 Hz, 2H), 0.94 (br. d, J=6.3 Hz, 3H), 0.92 (d, J=6.3 Hz, 3H). ¹³C NMR (100 MHz, CDCl₃) δ ppm: 176.1, 174.0, 172.9, 172.3, 172.2, 170.0, 62.6, 58.2, 56.9, 52.6, 47.8, 47.5, 39.2, 34.5, 31.4, 29.7, 28.6, 28.1, 25.9, 25.0, 24.4, 20.1, 17.3. MS (ESI): found [M+H]+, 494.4.

Cyclo-Asp(ᴰPro-Pro-Val)-NHCH₂CH₂CH₂CONHOH (14a)

The cyclic peptide 14a having the hydroxamic acid warhead on pendent carboxylic acid was synthesized from 12a by following the above general procedure for general procedure for hydroxamic acid synthesis from the methyl ester and purified by HPLC using 11-35% acetonitrile gradient over 30 minutes, obtaining the desired hydroxamic acid peptide as a white solid (yield, 87%; purity by LC-MS, >99%). ¹H NMR (400 MHz, DMSO-d₆) δ ppm: 10.30 (bs, 1H), 8.00 (t, J=4.7 Hz, 1H), 6.91 (d, J=8.2 Hz, 1H), 6.50 (d, J=9.8 Hz, 1H), 4.68 (t, J=7.0 Hz, 1H), 4.59 (t, J=6.3 Hz, 1H), 4.24 (d, J=3.5 Hz, 1H), 4.16 (dd, J=5.3, 8.4 Hz, 1H), 3.96 (d, J=8.6 Hz, 1H), 3.74-3.64 (m, 1H), 3.63-3.53 (m, 4H), 3.16-3.06 (m, 2H), 3.06-2.97 (m, 1H), 2.51-2.40 (m, 1H), 2.36-2.30 (m, 1H), 2.29-2.25 (m, 1H), 2.19-2.08 (m, 1H), 2.06-1.99 (m, 2H), 1.95 (t, J=7.0 Hz, 2H), 1.85-1.71 (m, 3H), 1.67-1.59 (p, J=6.8 Hz, 2H), 0.84 (d, J=6.7 Hz, 3H), 0.79 (d, J=6.7 Hz, 3H). ¹³C NMR (100 MHz, DMSO-d₆) δ ppm: 173.7, 171.5, 171.0, 170.3, 170.2, 169.3, 62.5, 58.0, 56.4, 50.2, 47.9, 47.3, 39.0, 36.1, 30.2, 29.9, 29.1, 28.2, 25.8, 25.5, 24.9, 20.1, 17.6. MS (ESI): found [M+H]+, 509.5.

Cyclo-ᴰAsp(ᴰPro-Pro-Val)-NHCH₂CH₂CH₂CONHOH (14b)

The cyclic peptide 14b having the hydroxamic acid warhead on pendent carboxylic acid was synthesized from 12b by following the above general procedure for general procedure for hydroxamic acid synthesis from the methyl ester and purified by HPLC using 11-35% acetonitrile gradient over 30 minutes, obtaining the desired hydroxamic acid peptide as a white solid (yield, 85%; purity by LC-MS, 99%). ¹H NMR (400 MHz, DMSO-d₆) δ ppm: 10.29 (bs, 1H), 7.73 (t, J=4.9 Hz, 1H), 6.89 (d, J=5.5 Hz, 1H), 6.37 (d, J=9.8 Hz, 1H), 4.68-4.62 (m, 1H), 4.27-4.14 (m, 3H), 4.01-3.86 (m, 2H), 3.75-3.66 (m, 3H), 3.61-3.58 (m, 2H), 3.05-2.89 (m, 3H), 2.30-2.04 (m, 6H), 2.03-1.88 (m, 6H), 1.88-1.75 (m, 4H), 1.63-1.54 (m, 2H), 0.84 (d, J=6.8 Hz, 3H), 0.78 (d, J=6.9 Hz, 3H). ¹³C NMR (100 MHz, DMSO-d₆) δ ppm: 173.9, 172.0, 171.6, 171.5, 169.4, 169.4, 62.5, 58.0, 56.3, 51.5, 47.6, 47.5, 38.8, 34.9, 30.2, 29.9, 28.6, 28.3, 25.9, 25.6, 24.9, 20.6, 17.6. MS (ESI): found [M+Na]+, 509.5.

Cyclo-Asp(ᴰPro-Pro-Val)-NHCH₂CH₂S—SCH₂CH₂NH₂ (15a)

The amine-containing peptide 15a was synthesized from 3a by following the above general procedure for EDCl peptide coupling of pendent carboxylic acid with cysteamine diamine and purified by HPLC using 11-35% acetonitrile gradient over 30 minutes, obtaining the desired homodimer as a viscous oil (yield, 65%; purity by LC-MS, >99%). ¹H NMR (400 MHz, CDCl₃) δ ppm: 8.24 (br. s., 2H), 7.76 (t, J=6.1 Hz, 1H), 7.19 (d, J=9.0 Hz, 1H), 6.30 (d, J=10.6 Hz, 1H), 5.04 (t, J=10.0 Hz, 1H), 4.59 (t, J=7.2 Hz, 1H), 4.50 (dd, J=3.3, 9.6 Hz, 1H), 4.43 (dd, J=6.1, 8.0 Hz, 1H), 4.20-4.12 (m, 1H), 3.80-3.72 (m, 1H), 3.70-3.52 (m, 4H), 3.38-3.26 (m, 2H), 3.19-3.10 (m, 2H), 3.02-2.91 (m, 2H), 2.62-2.53 (m, 2H), 2.45-2.36 (m, 3H), 2.20-2.09 (m, 4H), 2.03-1.89 (m, 2H), 0.86 (d, J=6.9 Hz, 3H), 0.85 (d, J=7.0 Hz, 3H). MS (ESI): found [M+H]+, 543.5.

Cyclo-ᴰAsp(ᴰPro-Pro-Val)-NHCH₂CH₂S—SCH₂CH₂NH₂ (15b)

The amine-containing peptide 15b was synthesized from 3b by following the above general procedure for EDCl peptide coupling of pendent carboxylic acid with cysteamine diamine and purified by HPLC using 11-35% acetonitrile gradient over 30 minutes, obtaining the desired homodimer as a viscous oil (yield, 67%; purity by LC-MS, 97%). ¹H NMR (400 MHz, CDCl₃) δ ppm: 8.11 (t, J=6.5 Hz, 1H), 8.06 (bs, 2H), 6.76 (d, J=9.8 Hz, 1H), 6.54 (d, J=7.0 Hz, 1H), 4.61 (dd, J=6.1, 7.2 Hz, 1H), 4.47-4.39 (m, 1H), 4.35-4.29 (m, 1H), 4.20 (dd, J=7.0, 16.4 Hz, 1H), 3.75-3.59 (m, 3H), 3.39-3.28 (m, 3H), 3.10-2.90 (m, 3H), 2.76 (t, J=12.7 Hz, 1H), 2.41-2.31 (m, 1H), 2.31-2.21 (m, 1H), 2.20-2.08 (m, 3H), 2.06-1.92 (m, 3H), 1.82-1.72 (m, 3H), 0.97 (d, J=6.3 Hz, 3H), 0.92 (d, J=6.7 Hz, 3H). MS (ESI): found [M+H]+, 543.5.

Cyclo-Asp(ᴰPro-Pro-Val)-NHCH₂CH₂CH₂NH₂ (16a) and Cyclo-ᴰAsp(ᴰPro-Pro-Val)-NHCH₂CH₂CH₂NH₂ (16b)

The amine-containing unseparable peptides 16a and 16b were synthesized by following the above general procedure for EDCl peptide coupling of pendent carboxylic acid with 1,3-diaminopropane and purified by HPLC using 11-35% acetonitrile gradient over 30 minutes, obtaining the desired diastereomeric mixture (3:1) of amino propyl amide as a viscous oil (yield, 81%; purity by LC-MS, 99%); Diastereomer 16a: ¹H NMR (400 MHz, CDCl₃) δ ppm: 7.04 (d, J=9.0 Hz, 1H), 6.57 (d, J=10.2 Hz, 1H), 5.07 (dt, J=3.2, 9.8 Hz, 1H), 4.63 (t, J=7.0 Hz, 1H), 4.48 (dd, J=3.9, 8.6 Hz, 1H), 4.36 (dd, J=4.7, 8.6 Hz, 1H), 4.21-4.11 (m, 1H), 3.77 (dt, J=6.7, 9.4 Hz, 1H), 3.72-3.62 (m, 2H), 3.62-3.54 (m, 1H), 3.38-3.31 (m, 3H), 2.66 (dd, J=9.6, 13.5 Hz, 1H), 2.55-2.44 (m, 1H), 2.36 (qd, J=8.0, 12.3 Hz, 1H), 2.22-2.07 (m, 5H), 2.07-1.82 (m, 6H), 0.92 (d, J=6.7 Hz, 3H), 0.88 (d, J=6.7 Hz, 3H). ¹³C NMR (100 MHz, CDCl₃) δ ppm: 173.2, 170.8, 170.7, 169.3, 168.3, 167.9, 61.9, 57.5, 55.5, 48.4, 47.4, 46.4, 34.8, 29.1, 28.4, 27.8, 27.3, 25.2, 24.2, 20.0, 19.2, 16.4. Diastereomer 16b: ¹H NMR (400 MHz, CDCl₃) δ ppm: 6.99 (d, J=9.4 Hz, 1H), 6.50 (d, J=6.3 Hz, 1H), 5.02-4.95 (m, 1H), 4.69 (dd, J=6.3, 7.4 Hz, 1H), 4.52 (dd, J=3.5, 8.6 Hz, 1H), 4.42 (dd, J=4.7, 9.4 Hz, 1H), 4.12-4.07 (m, 1H), 3.72-3.62 (m, 2H), 3.62-3.54 (m, 1H), 3.38-3.31 (m, 2H), 3.01 (dd, J=4.9, 12.3 Hz, 17H), 2.89 (t, J=12.0 Hz, 16H) 2.55-2.36 (m, 2H), 2.22-2.07 (m, 5H), 2.07-1.82 (m, 6H), 0.91 (d, J=6.7 Hz, 3H), 0.88 (d, J=6.7 Hz, 3H). MS (ESI): found [M+Na]+, 465.4.

Cyclo-Asp(Pro-ᴰPro-Val)-OBn (2a)

Cyclic tetrapeptide 2b was synthesized by following the above general procedure for DPPA macrolactamisation and purified by silica gel column chromatography (EtOAc) as a white solid (yield, 67%; purity by LC-MS, >97%). ¹H NMR (400 MHz, CDCl₃) δ ppm: 7.74 (d, J=10.0 Hz, 1H), 7.41-7.27 (m, 5H), 6.70 (d, J=7.6 Hz, 1H), 5.31 (d, J=12.3 Hz, 1H), 5.13 (d, J=12.5 Hz, 1H), 4.78 (dd, J=4.7, 7.8 Hz, 1H), 4.75 (d, J=7.4 Hz, 3H), 4.71 (dt, J=2.7, 5.3 Hz, 3H), 4.39-4.24 (m, 2H), 3.71-3.55 (m, 1H), 3.55-3.39 (m, 2H), 3.12 (dd, J=5.7, 15.5 Hz, 1H), 3.01 (dd, J=3.3, 15.5 Hz, 1H), 2.90-2.84 (m, 1H), 2.56 (dd, J=6.8, 12.3 Hz, 1H), 2.37-2.18

(m, 3H), 2.18-2.05 (m, 2H), 2.03-1.90 (m, 2H), 1.83-1.73 (m, 1H), 0.92 (d, J=6.7 Hz, 3H), 0.89 (d, J=6.8 Hz, 3H). $^{13}$C NMR (100 MHz, CDCl$_3$) δ ppm: 172.5, 170.6, 170.2, 170.1, 168.9, 135.4, 128.5, 128.2, 128.0, 67.4, 59.0, 57.5, 57.3, 49.3, 47.3, 47.2, 36.2, 28.3, 27.3, 25.8, 25.5, 25.0, 19.8, 17.5. MS (ESI): found [M+H]+, 499.4.

Cyclo-$^D$Asp(Pro-$^D$Pro-Val)-OBn (2b)

Cyclic tetrapeptide 2b was synthesized by following the above general procedure for DPPA macrolactamisation and purified by silica gel column chromatography (EtOAc) as a white solid (yield, 73%; purity by LC-MS, >99%). $^1$H NMR (400 MHz, CDCl$_3$) δ ppm: 7.41-7.29 (m, 5H), 7.01 (d, J=8.6 Hz, 1H), 6.77 (d, J=8.6 Hz, 1H), 5.21 (s, 2H), 4.73-4.66 (m, 1H), 4.61 (dd, J=2.2, 8.8 Hz, 1H), 4.56 (dd, J=2.3, 8.2 Hz, 1H), 4.08 (dd, J=6.3, 9.0 Hz, 1H), 3.86-3.76 (m, 1H), 3.76-3.68 (m, 1H), 3.51 (td, J=7.6, 11.8 Hz, 2H), 3.04 (dd, J=5.1, 14.9 Hz, 1H), 2.83 (dd, J=0.8, 5.1 Hz, 1H), 2.57-2.44 (m, 1H), 2.42-2.37 (m, 1H), 2.32 (dd, J=3.3, 15.1 Hz, 1H), 2.16-2.00 (m, 4H), 1.99-1.91 (m, 2H), 1.02 (d, J=7.0 Hz, 3H), 1.00 (d, J=7.1 Hz, 3H). $^{13}$C NMR (100 MHz, CDCl$_3$) δ ppm: 173.1, 171.2, 170.4, 170.2, 168.8, 135.8, 128.4, 128.3, 128.0, 67.1, 61.6, 60.4, 60.1, 49.2, 46.9, 46.9, 36.0, 30.2, 29.5, 26.6, 25.7, 22.4, 19.3, 18.3. MS (ESI): found [M+H]+, 499.4.

Cyclo-Asp(Pro-$^D$Pro-Val)-OH (4a)

Cyclic tetrapeptide pendent carboxylic acid 4a was synthesized from 2a by following the above general procedure for catalytic hydrogenation of benzyl ester, obtaining the desired pendent carboxylic acid as a white solid (yield, 94%; purity by LC-MS, >99%). $^1$H NMR (400 MHz, CDCl$_3$) δ ppm: 7.78 (d, J=10.2 Hz, 1H), 7.10 (d, J=6.7 Hz, 1H), 5.06 (bs, 1H), 4.73 (t, J=7.0 Hz, 2H), 4.66 (q, J=5.6 Hz, 1H), 4.25 (dd, J=8.8, 9.3 Hz, 1H), 4.19 (dd, J=2.9, 10.0 Hz, 1H), 3.66 (q, J=8.5 Hz, 1H), 3.58-3.50 (m, 1H), 3.46 (q, J=8.5 Hz, 1H), 3.26 (dd, J=5.9, 15.7 Hz, 1H), 2.95 (dd, J=4.5, 15.5 Hz, 1H), 2.48 (dd, J=7.2, 12.3 Hz, 1H), 2.39-2.24 (m, 2H), 2.20 (q, J=7.2 Hz, 1H), 2.10 (q, J=7.0 Hz, 2H), 2.04-1.90 (m, 2H), 1.87-1.74 (m, 1H), 0.92 (d, J=6.7 Hz, 3H), 0.89 (d, J=6.7 Hz, 3H). $^{13}$C NMR (100 MHz, CDCl$_3$) δ ppm: 172.5, 172.2, 170.9, 170.4, 169.2, 59.1, 58.6, 57.7, 49.3, 47.5, 47.2, 35.7, 28.7, 27.4, 25.7, 25.5, 24.9, 19.5, 17.9. MS (ESI): found [M+H]+, 409.4.

Cyclo-DAsp(Pro-DPro-Val)-OH (4b)

Cyclic tetrapeptide pendent carboxylic acid 4b was synthesized from 2b by following the above general procedure for catalytic hydrogenation of benzyl ester, obtaining the desired pendent carboxylic acid as a white solid (yield, 91%; purity by LC-MS, 97%). $^1$H NMR (400 MHz, CDCl$_3$) δ ppm: 7.20 (d, J=8.2 Hz, 1H), 6.94 (d, J=8.2 Hz, 1H), 6.55 (bs, 1H), 4.74 (dd, J=4.5, 7.4 Hz, 1H), 4.65 (dd, J=2.6, 8.2 Hz, 1H), 4.60 (dd, J=2.7, 8.0 Hz, 1H), 4.22-4.14 (m, 1H), 4.08 (dd, J=6.7, 8.2 Hz, 1H), 3.77-3.70 (m, 1H), 3.57-3.45 (m, 2H), 3.10 (dd, J=4.9, 15.1 Hz, 1H), 2.54-2.33 (m, 2H), 2.35 (dd, J=3.2, 15.2 Hz, 1H), 2.19-1.71 (m, 7H), 1.05 (d, J=6.7 Hz, 3H), 1.03 (d, J=6.7 Hz, H). $^{13}$C NMR (100 MHz, CDCl$_3$) δ ppm: 173.2, 173.1, 173.1, 173.0, 169.7, 61.8, 60.7, 60.3, 51.2, 47.1, 47.0, 39.8, 34.5, 30.1, 29.4, 27.6, 26.7, 25.7, 22.4, 19.3, 17.9. MS (ESI): found [M+H]+, 409.4.

Homdimer: [Cyclo-Asp(Pro-$^D$Pro-Val)-NHCH$_2$CH$_2$S]$_2$ (36a)

The homodimer prodrug thioether 36a was synthesized 4a by following the above general procedure for EDCl peptide coupling of pendent carboxylic acid with cysteamine diamine and purified by HPLC using 11-47% acetonitrile gradient, obtaining the desired homodimer as a white solid (yield, 77%; purity by LC-MS, >99%). $^1$H NMR (400 MHz, CDCl$_3$) δ ppm: 7.77 (d, J=9.0 Hz, 1H), 7.25 (bs, 1H), 7.22 (bs, 1H), 4.82-4.74 (m, 1H), 4.73-4.66 (m, 2H), 4.27 (t, J=8.2 Hz, 1H), 4.19 (t, J=7.6 Hz, 1H), 4.13-4.00 (m, 1H), 3.72-3.60 (m, 2H), 3.59-3.44 (m, 2H), 3.01 (dd, J=8.0, 14.0 Hz, 1H), 2.92 (dd, J=6.2, 14.4 Hz, 1H), 2.78 (t, J=6.5 Hz, 2H), 2.50-2.39 (m, 1H), 2.37-2.18 (m, 3H), 2.12 (q, J=6.8 Hz, 2H), 2.06-1.90 (m, 2H), 1.89-1.76 (m, 1H), 0.92 (d, J=6.7 Hz, 3H), 0.89 (d, J=7.0 Hz, 3H). $^{13}$C NMR (100 MHz, CDCl$_3$) δ ppm: 172.5, 171.7, 170.8, 169.7, 59.3, 58.9, 57.9, 49.8, 47.5, 47.3, 47.2, 38.6, 37.6, 36.7, 29.3, 27.6, 25.9, 25.8, 25.0, 19.7, 17.6. MS (ESI): found [M+H]+, 933.7.

Cyclo-Asp(Pro-$^D$Pro-Val)-NHCH$_2$CH$_2$SH (17a)

Thiol warhead having SLA analogue 17a was synthesized by following the above general procedure for synthesis of sulfhydryl from corresponding homodimer (36a), obtaining the desired pendent thiol as a white solid (yield, 74%; purity by LC-MS, >99%). $^1$H NMR (400 MHz, CDCl$_3$) δ ppm: 8.02 (bs, 1H), 7.75 (d, J=9.4 Hz, 1H), 7.08 (t, J=5.0 Hz, 1H), 4.78 (dt, J=5.1, 8.2 Hz, 1H), 4.73-4.64 (m, 2H), 4.25-4.07 (m, 2H), 3.75-3.60 (m, 2H), 3.57-3.46 (m, 2H), 3.42 (quin, J=6.5 Hz, 1H), 3.04 (dd, J=5.5, 14.5 Hz, 1H), 2.89 (dd, J=8.4, 14.7 Hz, 1H), 2.68-2.59 (m, 2H), 2.49-2.20 (m, 3H), 2.20-2.11 (m, 2H), 2.11-1.84 (m, 4H), 1.52 (t, J=8.6 Hz, 1H), 0.95 (d, J=7.0 Hz, 3H), 0.91 (d, J=6.7 Hz, 3H). MS (ESI): found [M+H]+, 468.4.

Homodimer: [Cyclo-$_D$Asp(Pro-$_D$Pro-Val)-NHCH$_2$CH$_2$S]$_2$ (36b)

The homodimer prodrug thioether 36b was synthesized from 4b by following the above general procedure for EDCl peptide coupling of pendent carboxylic acid with cysteamine diamine and purified by HPLC using 11-47% acetonitrile gradient, obtaining the desired homodimer as a white solid (yield, 73%; purity by LC-MS, >99%). $^1$H NMR (400 MHz, CDCl$_3$) δ ppm: 7.65 (d, J=8.5 Hz, 2H), 6.85 (bs, 1H), 4.74-4.67 (m, 3H), 4.59-4.41 (m, 1H), 4.14-4.04 (m, 1H), 3.78-3.65 (m, 2H), 3.57-3.49 (m, 3H), 3.21-3.15 (m, 1H), 3.09-2.90 (m, 1H), 2.79 (t, J=6.3 Hz, 2H), 2.48-2.40 (m, 1H), 2.33-2.25 (m, 2H), 2.20-2.14 (m, 1H), 2.06-1.98 (m, 4H), 1.91-1.78 (m, 1H), 0.97 (d, J=7.2 Hz, 3H), 0.94 (d, J=7.1 Hz, 3H). MS (ESI): found [M+H]+, 933.7.

Cyclo-$^D$Asp(Pro-$^D$Pro-Val)-NHCH$_2$CH$_2$SH (17b)

Thiol warhead having SLA analogue 17b was synthesized by following the above general procedure for synthesis of sulfhydryl from corresponding homodimer (36b), obtaining the desired pendent thiol as a white solid (yield, 71%; purity by LC-MS, >99%). $^1$H NMR (400 MHz, CDCl$_3$) δ ppm: 7.64 (d, J=9.8 Hz, 1H), 7.45 (t, J=5.3 Hz, 1H), 6.87 (d, J=6.7 Hz, 1H), 4.76-4.69 (m, 2H), 4.68-4.57 (m, 1H), 4.17-4.09 (m, 2H), 3.85-3.65 (m, 1H), 3.61-3.47 (m, 4H), 3.27 (dd, J=11.3, 16.0 Hz, 1H), 2.87 (dd, J=5.1, 16.0 Hz, 1H), 2.74-2.68 (m, 1H), 2.67-2.61 (m, 1H), 2.50-2.42 (m, 1H), 2.35-2.29 (m, 1H), 2.22-1.99 (m, 7H), 1.45 (t, J=8.6 Hz, 1H), 0.96 (d, J=6.9 Hz, 3H), 0.94 (d, J=6.9 Hz, 6H). MS (ESI): found [M+H]+, 468.4.

Homodimer: [Cyclo-Asp(Pro-$^D$Pro-Val)-NHCH$_2$CH$_2$CH$_2$S]$_2$ Prodrug (38a)

The homodimer prodrug thioether 38a was synthesized from 4a by following the above general procedure for EDCl peptide coupling of pendent carboxylic acid with cysteamine diamine and purified by HPLC using 11-47% acetonitrile gradient, obtaining the desired homodimer as a white solid (yield, 67%; purity by LC-MS, >99%). $^1$H NMR (400 MHz, CDCl$_3$) δ ppm: 7.60 (d, J=9.0 Hz, 1H), 7.53 (t, J=7.2 Hz, 1H), 6.57 (bs, 1H), 4.74-4.61 (m, 2H), 4.68 (dd, J=7.6, 14.7 Hz, 1H), 4.12-4.08 (m, 1H), 4.07 (t, J=7.2 Hz, 1H), 3.80-3.65 (m, 1H), 3.60-3.39 (m, 2H), 3.29-3.19 (m, 1H), 3.15-3.06 (m, 1H), 2.80 (dd, J=5.0, 16.0 Hz, 1H), 2.72 (t, J=7.0 Hz, 2H), 2.41-2.28 (m, 4H), 2.15-1.89 (m, 5H), 1.88 (quin, J=6.8 Hz, 2H), 0.96 (t, J=6.7 Hz, 6H). MS (ESI): found [M+H]+, 961.7.

Cyclo-Asp(Pro-$^D$Pro-Val)-NHCH$_2$CH$_2$CH$_2$SH (18a)

Thiol warhead having SLA analogue 18a was synthesized by following the above general procedure for synthesis of sulfhydryl from corresponding homodimer (38a), obtaining the desired pendent thiol as a white solid (yield, 88%; purity by LC-MS, >99%). $^1$H NMR (400 MHz, CDCl$_3$) δ ppm: 7.62 (d, J=9.8 Hz, 1H), 7.21 (t, J=5.5 Hz, 1H), 6.61 (d, J=6.7 Hz, 1H), 4.80-4.62 (m, 3H), 4.62-4.48 (m, 1H), 4.16 (t, J=9.4 Hz, 1H), 3.69 (q, J=8.1 Hz, 1H), 3.61-3.44 (m, 2H), 3.38 (tdd, J=6.8, 13.2, 19.8 Hz, 2H), 3.27 (dd, J=11.0, 16.0 Hz, 1H), 2.81 (dd, J=5.3, 15.8 Hz, 1H), 2.54 (q, J=7.2 Hz, 2H), 2.47 (dd, J=7.0, 12.5 Hz, 1H), 2.32 (td, J=7.8, 11.3 Hz, 2H), 2.16-2.14 (m, 1H), 2.13-1.84 (m, 7H), 1.80 (quin, J=6.8 Hz, 2H), 1.45 (t, J=8.0 Hz, 1H), 0.95 (d, J=7.1 Hz, 3H), 0.93 (d, J=7.1 Hz, 3H). MS (ESI): found [M+H]+, 482.4.

Homodimer: [Cyclo-$^D$Asp(Pro-$^D$Pro-Val)-NHCH$_2$CH$_2$CH$_2$S]$_2$ Prodrug (38b)

The homodimer prodrug thioether 38b was synthesized from 4b by following the above general procedure for EDCl peptide coupling of pendent carboxylic acid with cysteamine diamine and purified by HPLC using 11-47% acetonitrile gradient, obtaining the desired homodimer as a white solid (yield, 63%; purity by LC-MS, >99%). $^1$H NMR (400 MHz, CDCl$_3$) δ ppm: 7.79 (d, J=9.0 Hz, 1H), 6.83 (bs, 1H), 6.68 (bs, 1H), 4.74-4.64 (m, 3H), 4.54-4.48 (m, 1H), 4.32-4.25 (m, 1H), 4.24-4.17 (m, 1H), 3.78-3.38 (m, 5H), 3.34 (dd, J=6.5, 13.5 Hz, 1H), 2.94-2.68 (m, 3H), 2.49 (d, J=7.8 Hz, 1H), 2.42-2.28 (m, 2H), 2.16-1.88 (m, 8H), 0.94 (d, J=6.9 Hz, 3H), 0.89 (d, J=7.0 Hz, 3H). MS (ESI): found [M+H]+, 961.7.

Cyclo-$^D$Asp(Pro-$^D$Pro-Val)-NHCH$_2$CH$_2$CH$_2$SH (18b)

Thiol warhead having SLA analogue 18b was synthesized by following the above general procedure for synthesis of sulfhydryl from corresponding homodimer (38b), obtaining the desired pendent thioether as a white solid (yield, 87%; purity by LC-MS, >99%). $^1$H NMR (400 MHz, CDCl$_3$) δ ppm: 7.79 (d, J=9.4 Hz, 1H), 6.89 (d, J=8.2 Hz, 1H), 6.67 (t, J=5.3 Hz, 1H), 4.75-4.65 (m, 3H), 4.62-4.55 (m, 1H), 4.26 (dd, J=5.9, 9.4 Hz, 1H), 3.67-3.56 (m, 2H), 3.56-3.41 (m, 2H), 3.38-3.27 (m, 1H), 3.09 (dd, J=5.5, 14.9 Hz, 1H), 2.84 (dd, J=5.7, 15.1 Hz, 1H), 2.57 (q, J=7.0 Hz, 2H), 2.54-2.45 (m, 1H), 2.43-2.27 (m, 3H), 2.18-2.09 (m, 3H), 2.09-1.96 (m, 2H), 1.86-1.79 (m, 2H), 1.49 (t, J=8.0 Hz, 1H), 0.95 (d, J=7.0 Hz, 3H), 0.90 (d, J=7.1 Hz, 3H). MS (ESI): found [M+H]+, 482.4.

Cyclo-Asp(Pro-$^D$Pro-Val)-NHCH$_2$CH$_2$CH$_2$SCH$_3$ (19a)

The cyclic peptide 19a having the methylthioether warhead on pendent carboxylic acid was synthesized from 4a by following the above general procedure for EDCl peptide coupling of pendent carboxylic acid with 3-(methylthio)propan-1-amine and purified by HPLC using 5-55% acetonitrile gradient, obtaining the desired peptide as a white solid (yield, 70%; purity by LC-MS, 97%). $^1$H NMR (400 MHz, CDCl$_3$) δ ppm: 7.72 (d, J=9.4 Hz, 1H), 7.01 (d, J=8.6 Hz, 1H), 6.82 (t, J=4.8 Hz, 1H), 4.74-4.62 (m, 2H), 4.23 (dd, J=6.8, 9.0 Hz, 2H), 3.69-3.55 (m, 2H), 3.54-3.46 (m, 2H), 3.43-3.28 (m, 2H), 2.98 (dd, J=6.9, 14.8 Hz, 1H), 2.89 (dd, J=5.3, 14.5 Hz, 1H), 2.52 (t, J=7.1 Hz, 2H), 2.39-2.23 (m, 3H), 2.17-2.06 (m, 2H), 2.09 (s, 3H), 2.06-1.83 (m, 4H), 1.81 (p, J=7.2 Hz, 2H), 0.93 (d, J=6.8 Hz, 3H), 0.90 (d, J=6.8 Hz, 3H). $^{13}$C NMR (100 MHz, CDCl$_3$) δ ppm: 172.5, 171.6, 170.7, 170.4, 169.9, 59.6, 59.5, 58.8, 58.1, 49.9, 47.6, 47.3, 38.8, 36.1, 31.3, 28.9, 28.3, 27.5, 26.1, 25.7, 25.0, 19.5, 17.4. MS (ESI): found [M+Na]+, 518.4.

Cyclo-$^D$Asp(Pro-$^D$Pro-Val)-NHCH$_2$CH$_2$CH$_2$SCH$_3$ (19b)

The cyclic peptide 19b having the methylthioether warhead on pendent carboxylic acid was synthesized from 4b by following the above general procedure for EDCl peptide coupling of pendent carboxylic acid with 3-(methylthio)propan-1-amine and purified by HPLC using 5-55% acetonitrile gradient, obtaining the desired peptide as a white solid (yield, 70%; purity by LC-MS, 98%). $^1$H NMR (400 MHz, CDCl$_3$) δ ppm: 7.63 (d, J=10.2 Hz, 1H), 7.16 (t, J=5.7 Hz, 2H), 6.54 (d, J=6.7 Hz, 2H), 4.79-4.71 (m, 1H), 4.72 (t, J=6.7 Hz, 2H), 4.58-4.48 (m, 2H), 4.20-4.09 (m, 1H), 3.90-3.77 (m, 1H), 3.73-3.61 (m, 1H), 3.59-3.50 (m, 2H), 3.49-3.42 (m, 1H), 3.41-3.31 (m, 2H), 3.27 (dd, J=10.6, 16.0 Hz, 1H), 2.81 (dd, J=5.1, 16.0 Hz, 1H), 2.64-2.41 (m, 1H), 2.51 (t, J=6.7 Hz, 2H), 2.31 (tdd, J=4.3, 7.8, 11.5 Hz, 2H), 2.16-2.07 (m, 2H), 2.08 (s, 3H), 2.05-1.95 (m, 2H), 1.87-1.80 (m, 2H), 1.79 (p, J=2.7 Hz, 2H), 0.95 (d, J=2.7 Hz, 3H), 0.93 (d, J=2.7 Hz, 3H). $^{13}$C NMR (100 MHz, CDCl$_3$) δ ppm: 173.4, 172.4, 171.0, 169.7, 169.3, 59.9, 59.2, 58.2, 52.5, 47.6, 47.1, 38.7, 34.3, 31.3, 29.7, 28.4, 27.6, 26.0, 25.6, 24.8, 22.8, 19.3, 18.5. MS (ESI): found [M+H]+, 496.4.

Cyclo-Asp(Pro-$^D$Pro-Val)-NHCH$_2$CH$_2$CH$_2$S(=O)CH$_3$ (20a)

The cyclic peptide 20a having the methylsulfoxide warhead on pendent carboxylic acid was synthesized from 19a by following the above general procedure for sulfoxide synthesis from organic sulfides by H$_2$O$_2$/Borax and purified by HPLC using 5-50% acetonitrile gradient, obtaining the desired sulfoxide as a white solid (yield, 71%; purity by LC-MS, 98%). Nonseparable diastereomeric mixture=1.1:1. $^1$H NMR (400 MHz, CDCl$_3$) δ ppm: 7.87 (d, J=9.0 Hz, 1H), 7.50 (t, J=7.0 Hz, 1H), 7.45 (d, J=6.0 Hz, 1H), 4.74-4.61 (m, 3H), 4.22-4.16 (m, 1H), 3.74-3.64 (m, 1H), 3.64-3.55 (m, 1H), 3.55-3.43 (m, 1H), 3.28 (dd, J=6.1, 12.7 Hz, 1H), 3.14 (t, J=7.8 Hz, 2H), 2.94 (dd, J=1.8, 4.0 Hz, 1H), 2.92 (s, 3H), 2.90-2.86 (m, 2H), 2.39 (d, J=9.8 Hz, 1H), 2.36-2.20 (m, 3H), 2.17-2.08 (m, 2H), 2.08-1.96 (m, 5H), 0.93 (d, J=6.8 Hz, 3H), 0.91 (d, J=6.8 Hz, 3H). $^{13}$C NMR (100 MHz, CDCl$_3$) δ ppm: 172.4, 171.0, 171.0, 170.7, 169.2, 59.3, 58.9, 57.7, 51.8, 50.1, 47.4, 47.1, 37.6, 37.0, 29.5, 28.8, 27.4, 26.1, 25.6, 25.0, 22.6, 19.5, 17.6. MS (ESI): found [M+H]+, 512.4.

Cyclo-$^D$Asp(Pro-$^D$Pro-Val)-NHCH$_2$CH$_2$CH$_2$S(=O)CH$_3$ (20b)

The cyclic peptide 20b having the methylsulfoxide warhead on pendent carboxylic acid was synthesized from 19b by following the above general procedure for sulfoxide synthesis from organic sulfides by $H_2O_2$/borax and purified by HPLC using 5-50% acetonitrile gradient, obtaining the desired sulfoxide as a white solid (yield, 67%; purity by LC-MS, >99%). Nonseparable diastereomeric mixture=1.1:1. $^1$H NMR (400 MHz, CDCl$_3$) δ ppm: 7.80 (t, J=8.0 Hz, 1H), 6.92 (bs, 1H), 6.82 (t, J=9.4 Hz, 1H), 4.79-4.68 (m, 2H), 4.68-4.61 (m, 1H), 4.31-4.26 (m, 2H), 3.65-3.47 (m, 2H), 3.42-3.28 (m, 1H), 3.25-3.11 (m, 2H), 2.92-2.75 (m, 2H), 2.63 (s, 3H), 2.49-2.38 (m, 1H), 2.40 (td, J=6.8, 12.9 Hz, 1H), 2.36-2.22 (m, 2H), 2.18-2.10 (m, 2H), 2.09-1.93 (m, 6H), 1.91-1.82 (m, 1H), 0.95 (d, J=7.0 Hz, 3H), 0.90 (d, J=7.0 Hz, 3H). $^{13}$C NMR (100 MHz, CDCl$_3$) δ ppm: 172.3, 171.1, 170.8, 170.8, 169.1, 59.3, 58.9, 57.7, 51.4, 50.0, 47.4, 47.0, 38.4, 38.1, 37.1, 28.9, 27.5, 26.1, 25.6, 25.0, 22.7, 19.5, 17.8. MS (ESI): found [M+H]+, 512.4.

Cyclo-Asp(Pro-$^D$Pro-Val)-NHCH$_2$CH$_2$CH$_2$S(=O)$_2$CH$_3$ (21a)

The cyclic peptide 21a having the methylsulfone warhead on pendent carboxylic acid was synthesized from 19a by following the above general procedure for sulfones synthesis from organic sulfides by $H_2O_2$/borax and purified by HPLC using 5-48% acetonitrile gradient over 30 minutes, obtaining the desired sulfone as a white solid (yield, 89%; purity by LC-MS, >99%). $^1$H NMR (400 MHz, CDCl$_3$) δ ppm: 7.81 (d, J=9.2 Hz, 1H), 6.70 (t, J=6.0 Hz, 1H), 6.57 (d, J=8.8 Hz, 1H), 4.79 (t, J=6.7 Hz, 1H), 4.72 (d, J=7.4 Hz, 1H), 4.61 (ddd, J=3.3, 5.8, 8.9 Hz, 1H), 4.37-4.33 (m, 1H), 4.33-4.28 (m, 1H), 3.68-3.47 (m, 4H), 3.32-3.22 (m, 1H), 3.22-3.11 (m, 2H), 2.90 (s, 3H), 2.73 (dd, J=6.0, 15.0 Hz, 1H), 2.55-2.43 (m, 2H), 2.38-2.26 (m, 2H), 2.17-2.13 (m, 1H), 2.14 (p, J=6.8 Hz, 2H), 2.09-1.95 (m, 3H), 1.92-1.82 (m, 1H), 0.97 (d, J=6.8 Hz, 3H), 0.90 (d, J=6.8 Hz, 3H). $^{13}$C NMR (100 MHz, CDCl$_3$) δ ppm: 173.0, 171.1, 170.9, 170.8, 170.0, 59.4, 58.6, 58.1, 51.8, 50.3, 47.7, 47.6, 40.5, 37.8, 35.8, 29.7, 28.5, 27.4, 26.1, 25.8, 25.3, 22.9, 19.8, 16.9. MS (ESI): found [M+H]+, 528.4.

Cyclo-$^D$Asp(Pro-$^D$Pro-Val)-NHCH$_2$CH$_2$CH$_2$S(=O)$_2$CH$_3$ (21b)

The cyclic peptide 21b having the methylsulfone warhead on pendent carboxylic acid was synthesized from 19b by following the above general procedure for sulfones synthesis from organic sulfides by $H_2O_2$/borax at 60° C. for 24 h and purified by HPLC using 5-48% acetonitrile gradient over 30 minutes, obtaining the desired sulfone as a white solid (yield, 83%; purity by LC-MS, 99%). $^1$H NMR (400 MHz, CDCl$_3$) δ ppm: 7.82 (d, J=8.9 Hz, 1H), 6.83 (t, J=5.7 Hz, 1H), 6.75 (d, J=8.6 Hz, 1H), 4.76 (t, J=6.7 Hz, 1H), 4.71 (dd, J=1.8, 7.9 Hz, 1H), 4.67-4.61 (m, 1H), 4.33-4.26 (m, 2H), 3.65-3.50 (m, 2H), 3.36-3.26 (m, 1H), 3.19-3.11 (m, 2H), 2.94 (d, J=3.9 Hz, 1H), 2.91 (s, 3H), 2.80 (dd, J=5.9, 14.9 Hz, 1H), 2.52-2.40 (m, 2H), 2.37-2.30 (m, 2H), 2.14 (t, J=7.0 Hz, 2H), 2.10-1.99 (m, 3H), 1.89-1.75 (m, 2H), 1.64 (p, J=6.8 Hz, 2H), 0.96 (d, J=7.0 Hz, 3H), 0.90 (d, J=6.7 Hz, 3H). $^{13}$C NMR (100 MHz, CDCl$_3$) δ ppm: 171.5, 171.3, 170.9, 170.9, 165.6, 59.4, 58.7, 58.1, 51.8, 50.2, 47.6, 40.5, 37.8, 36.0, 31.9, 29.7, 28.6, 27.4, 26.1, 25.8, 25.3, 22.7, 19.7, 17.0. MS (ESI): found [M+H]+, 528.4.

Cyclo-Asp(Pro-$^D$Pro-Val)-NHCH$_2$CH$_2$CH$_2$OH (22a) and Cyclo-$^D$Asp(Pro-$^D$Pro-Val)-NHCH$_2$CH$_2$CH$_2$OH (22b)

The cyclic peptide 22a and 22b having the n-propylalcohol warhead on pendent carboxylic acid was synthesized by following the above general procedure for EDCl peptide coupling of pendent carboxylic acid with 3-aminopropan-1-ol and purified by HPLC using 11-40% acetonitrile gradient over 30 minutes, obtaining the desired alcohol as viscous oil (yield, 75%; purity by LC-MS, >96%). Nonseparable diastereomeric mixture (1:0.65). Diastereomer 22a: $^1$H NMR (400 MHz, CDCl$_3$) δ ppm: 7.81 (d, J=9.0 Hz, 1H), 6.72 (d, J=8.5 Hz, 1H), 6.65 (t, J=5.5 Hz, 1H), 4.75 (t, J=7.0 Hz, 2H), 4.70-4.64 (m, 1H), 4.42 (t, J=6.5 Hz, 1H), 4.39-4.28 (m, 1H), 3.72-3.67 (m, 1H), 3.65-3.39 (m, 5H), 3.37-3.26 (m, 1H), 3.19 (dd, J=4.3, 14.9 Hz, 1H), 2.75 (t, J=6.5 Hz, 2H), 2.57-2.40 (m, 2H), 2.38-2.20 (m, 2H), 2.18-2.10 (m, 2H), 2.10-1.80 (m, 5H), 0.96 (d, J=6.9 Hz, 3H), 0.94 (d, J=7.0 Hz, 3H). Diastereomer 22b: $^1$H NMR (400 MHz, CDCl$_3$) δ ppm: 7.99 (d, J=9.8 Hz, 1H), 7.02 (t, J=6.5 Hz, 1H), 6.75 (d, J=8.4 Hz, 1H), 4.73 (t, J=7.0 Hz, 2H), 4.63-4.59 (m, 1H), 4.39-4.28 (m, 2H), 3.65-3.39 (m, 5H), 3.37-3.26 (m, 2H), 2.71 (t, J=7.0 Hz, 1H), 2.57-2.40 (m, 2H), 2.38-2.20 (m, 2H), 2.18-2.10 (m, 2H), 2.10-1.80 (m, 3H), 1.71 (quin, J=5.7 Hz, 2H), 0.90 (d, J=6.9 Hz, 3H), 0.88 (d, J=7.0 Hz, 3H). MS (ESI): found [M+H]+, 466.4.

Cyclo-Asp(Pro-$^D$Pro-Val)-NHCH$_2$CH$_2$CH$_2$COOMe (23a)

The cyclic peptide 23a having the methylcarboxylate warhead on pendent carboxylic acid was synthesized from 4a by following the above general procedure for EDCl peptide coupling of coupling of pendent carboxylic acid with methyl 4-aminobutanoate and purified by HPLC using 11-45% acetonitrile gradient over 30 minutes, obtaining the desired peptide as a white solid (yield, 86%; purity by LC-MS, 98%). $^1$H NMR (400 MHz, CDCl$_3$) δ ppm: 7.79 (d, J=9.0 Hz, 1H), 6.91 (bs, 1H), 6.78 (bs, 1H), 4.72 (t, J=6.5 Hz, 2H), 4.69-4.63 (m, 1H), 4.36-4.22 (m, 2H), 3.68 (s, 3H), 3.65-3.55 (m, 2H), 3.50 (q, J=8.6 Hz, 1H), 3.34-3.25 (m, 2H), 2.83 (dd, J=5.1, 14.9 Hz, 1H), 2.50 (dd, J=7.0, 11.0 Hz, 1H), 2.44-2.35 (m, 4H), 2.35-2.24 (m, 2H), 2.14 (q, J=6.8 Hz, 2H), 2.09-1.91 (m, 2H), 1.84 (p, J=6.3 Hz, 2H), 0.94 (d, J=6.7 Hz, 3H), 0.90 (d, J=6.7 Hz, 3H). $^{13}$C NMR (100 MHz, CDCl$_3$) δ ppm: 173.7, 172.7, 171.6, 170.5, 170.4, 170.0, 59.4, 58.5, 58.1, 51.7, 49.8, 47.5, 47.3, 39.1, 35.9, 31.2, 28.8, 27.5, 26.0, 25.7, 25.0, 24.4, 19.6, 17.2. MS (ESI): found: [M+H]+, 508.5.

Cyclo-$^D$Asp(Pro-$^D$Pro-Val)-NHCH$_2$CH$_2$CH$_2$COOMe (23b)

The cyclic peptide 23b having the methylcarboxylate warhead on pendent carboxylic acid was synthesized from 4b by following the above general procedure for EDCl peptide coupling of coupling of pendent carboxylic acid with methyl 4-aminobutanoate and purified by HPLC using 11-45% acetonitrile gradient over 30 minutes, obtaining the desired peptide as a white solid (yield, 85%; purity by LC-MS, >98%). $^1$H NMR (400 MHz, CDCl$_3$) δ ppm: 7.62 (d, J=10.2 Hz, 1H), 7.13 (t, J=5.6 Hz, 1H), 6.74 (d, J=6.7 Hz, 1H), 4.71 (t, J=8.5 Hz, 1H), 4.72 (dd, J=3.1, 7.7 Hz, 1H), 4.55-4.49 (m, 1H), 4.23-4.12 (m, 2H), 3.77-3.67 (m, 1H), 3.67 (s, 3H), 3.59-3.45 (m, 2H), 3.31-3.25 (m, 4H), 2.77 (dd, J=5.1, 16.0 Hz, 1H), 2.53-2.39 (m, 2H), 2.35 (t, J=7.2 Hz, 2H), 2.33-2.22 (m, 2H), 2.20-2.10 (m, 1H), 2.09-1.90 (m, 6H), 1.81 (quin, J=7.2 Hz, 2H), 0.94 (d, J=4.7 Hz, 3H), 0.93 (d, J=4.7 Hz, 3H). $^{13}$C NMR (100 MHz, CDCl$_3$) δ ppm: 173.6, 173.3, 172.3, 170.9, 169.7, 169.2, 77.3, 77.0, 76.7, 59.9, 59.1, 58.0, 52.4, 51.7, 47.5, 47.0, 38.8, 34.2, 31.2, 29.7, 27.7, 26.0, 25.6, 24.8, 24.5, 19.3, 18.5. MS (ESI): found [M+H]+, 508.5.

Cyclo-Asp(Pro-$^D$Pro-Val)-NHCH$_2$CH$_2$CH$_2$COOH (24a)

The cyclic peptide 24a having the carboxylic acid warhead on pendent carboxylic acid was synthesized from 23a by following the above general procedure for general procedure for LiOH base mediated hydrolysis of methyl ester and purified by HPLC using 11-35% acetonitrile gradient over 30 minutes, obtaining the desired peptide as a white solid (yield, 93%; purity by LC-MS, >99%). $^1$H NMR (400 MHz, CDCl$_3$) δ ppm: 8.28 (d, J=10.2 Hz, 1H), 7.01 (t, J=5.2 Hz, 1H), 6.84 (d, J=9.0 Hz, 1H), 4.82 (d, J=7.8 Hz, 1H), 4.73 (t, J=6.8 Hz, 1H), 4.68 (dd, J=4.5, 10.0 Hz, 2H), 4.35 (dt, J=2.0, 9.4 Hz, 1H), 3.65-3.57 (m, 1H), 3.57-3.39 (m, 3H), 3.32 (dd, J=2.0, 16.0 Hz, 1H), 3.29-3.20 (m, 1H), 2.75 (dd, J=6.3, 16.0 Hz, 1H), 2.60-2.44 (m, 3H), 2.40 (dd, J=2.7, 10.2 Hz, 1H), 2.33-2.21 (m, 2H), 2.18-2.10 (m, 2H), 2.10-1.91 (m, 3H), 1.90-1.76 (m, 2H), 0.95 (d, J=6.7 Hz, 3H), 0.88 (d, J=6.7 Hz, 3H). $^{13}$C NMR (100 MHz, CDCl$_3$) δ ppm: 174.1, 174.0, 171.1, 170.0, 168.3, 167.7, 58.1, 58.0, 56.5, 48.6, 46.4, 45.9, 37.8, 36.5, 30.4, 28.6, 26.6, 24.8, 24.7, 23.9, 23.5, 18.5, 17.1. MS (ESI): found [M+H]+, 494.4.

Cyclo-$^D$Asp(Pro-$^D$Pro-Val)-NHCH$_2$CH$_2$CH$_2$COOH (24b)

The cyclic peptide 24b having the carboxylic acid warhead on pendent carboxylic acid was synthesized from 23b by following the above general procedure for general procedure for LiOH base mediated hydrolysis of methyl ester and purified by HPLC using 11-35% acetonitrile gradient over 30 minutes, obtaining the desired peptide as a white solid (yield, 95%; purity by LC-MS, >99%). $^1$H NMR (400 MHz, CDCl$_3$) δ ppm: 7.49 (d, J=10.2 Hz, 1H), 6.95 (t, J=5.7 Hz, 1H), 6.70 (d, J=7.4 Hz, 1H), 5.57 (bs, 1H), 4.76 (d, J=7.0 Hz, 1H), 4.73-4.60 (m, 2H), 4.32 (dd, J=8.4, 10.0 Hz, 1H), 4.19 (dt, J=3.0, 9.0 Hz, 1H), 3.69-3.40 (m, 3H), 3.32 (dd, J=8.4, 15.1 Hz, 1H), 3.27-3.17 (m, 1H), 2.75 (dd, J=6.5, 15.1 Hz, 1H), 2.56-2.30 (m, 4H), 2.25 (td, J=3.9, 7.5 Hz, 1H), 2.20-2.10 (m, 2H), 2.08-1.90 (m, 4H), 1.86 (quin, J=7.0 Hz, 2H), 0.95 (d, J=7.0 Hz, 6H). $^{13}$C NMR (100 MHz, CDCl$_3$) δ ppm: 176.3, 173.7, 172.1, 170.9, 169.4, 169.3, 59.8, 59.5, 58.2, 51.2, 47.6, 47.0, 39.3, 34.0, 31.8, 29.7, 27.7, 26.1, 25.8, 24.7, 24.7, 19.4, 18.5. MS (ESI): found [M+H]+, 494.4.

Cyclo-Asp(Pro-$^D$Pro-Val)-NHCH$_2$CH$_2$CH$_2$CONHOH (25a)

The cyclic peptide 25a having the hydroxamic acid warhead on pendent carboxylic acid was synthesized from 23a by following the above general procedure for general procedure for hydroxamic acid synthesis from the methyl ester and purified by HPLC using 11-35% acetonitrile gradient over 30 minutes, obtaining the desired hydroxamic acid peptide as a white solid (yield, 86%; purity by LC-MS, 99%). $^1$H NMR (400 MHz, DMSO-d$_6$) δ ppm: 10.08 (bs, 1H), 8.27 (d, J=8.2 Hz, 1H), 7.51 (t, J=5.5 Hz, 1H), 6.94 (d, J=5.5 Hz, 1H), 4.83 (dd, J=2.1, 8.1 Hz, 1H), 4.63 (dd, J=2.0, 7.7 Hz, 1H), 4.54 (t, J=7.2 Hz, 1H), 4.16 (t, J=6.1 Hz, 1H), 3.88 (t, J=7.8 Hz, 1H), 3.77-3.69 (m, 1H), 3.53-3.43 (m, 3H), 3.40-3.38 (m, 1H), 3.26 (td, J=7.6, 11.3 Hz, 1H), 3.03-2.93 (m, 2H), 2.89 (dd, J=5.1, 14.5 Hz, 1H), 2.41-2.05 (m, 4H), 1.99-1.60 (m, 5H), 1.54 (quin, J=6.8 Hz, 2H), 0.83 (d, J=7.0 Hz, 3H), 0.78 (d, J=6.7 Hz, 3H). $^{13}$C NMR (100 MHz, DMSO-d$_6$) δ ppm: 173.0, 172.0, 171.0, 170.4, 69.5, 168.0, 60.0, 59.7, 57.2, 52.2, 47.0, 46.8, 40.8, 38.7, 30.1, 29.7, 28.0, 25.6, 25.6, 24.8, 22.5, 19.9, 17.9. MS (ESI): found [M+H]+, 509.5.

Cyclo-$^D$Asp(Pro-$^D$Pro-Val)-NHCH$_2$CH$_2$CH$_2$CONHOH (25b)

The cyclic peptide 25b having the hydroxamic acid warhead on pendent carboxylic acid was synthesized from 23b by following the above general procedure for general procedure for hydroxamic acid synthesis from the methyl ester and purified by HPLC using 11-35% acetonitrile gradient over 30 minutes, obtaining the desired hydroxamic acid peptide as a white solid (yield, 87%; purity by LC-MS, >99%). $^1$H NMR (400 MHz, CDCl$_3$) δ ppm: 10.33 (s, 1H), 7.79 (d, J=9.8 Hz, 1H), 7.77 (d, J=7.4 Hz, 1H), 7.72 (t, J=5.3 Hz, 1H), 4.73-4.60 (m, 2H), 4.46-4.32 (m, 1H), 3.92-3.87 (m, 1H), 3.84 (t, J=9.2 Hz, 1H), 3.63 (t, J=6.5 Hz, 1H), 3.58-3.38 (m, 3H), 3.16-2.89 (m, 3H), 2.80 (dd, J=4.0, 16.0 Hz, 1H), 2.60 (dd, J=4.3, 15.7 Hz, 1H), 2.37-2.20 (m, 1H), 2.16 (dd, J=3.0, 16.0 Hz, 1H), 2.08-1.55 (m, 9H), 0.85 (d, J=6.7 Hz, 3H), 0.83 (d, J=6.7 Hz, 3H). $^{13}$C NMR (100 MHz, DMSO-d$_6$) δ ppm: 171.9, 171.1, 170.6, 170.3, 169.2, 169.2, 59.5, 59.1, 58.7, 49.3, 47.2, 46.6, 38.8, 38.3, 30.2, 29.7, 27.7, 26.3, 25.5, 24.8, 22.5, 19.7, 18.8. MS (ESI): found [M+H]+, 509.5.

Cyclo-Asp(Pro-$^D$Pro-Val)-NHCH$_2$CH$_2$S—SCH$_2$CH$_2$NH$_2$ (26a)

The amine-containing peptide 26a was synthesized from 4a by following the above general procedure for EDCl peptide coupling of pendent carboxylic acid with cysteamine diamine and purified by HPLC using 11-35% acetonitrile gradient over 30 minutes, obtaining the desired homodimer as a viscous oil (yield, 69%; purity by LC-MS, 96%). $^1$H NMR (400 MHz, CDCl$_3$) δ ppm: 8.39 (bs, 2H), 7.87 (d, J=9.0 Hz, 1H), 7.72 (t, J=5.7 Hz, 1H), 7.45 (d, J=8.6 Hz, 1H), 4.72-4.67 (m, 3H), 4.31-4.21 (m, 1H), 4.17 (t, J=8.2 Hz, 1H), 3.69-3.61 (m, 1H), 3.55-3.49 (m, 3H), 3.35-3.15 (m, 5H), 3.01-2.90 (m, 2H), 2.89-2.76 (m, 1H), 2.46-2.36 (m, 1H), 2.36-2.16 (m, 3H), 2.16-1.91 (m, 4H), 1.90-1.77 (m, 1H), 0.91 (d, J=4.3 Hz, 3H), 0.89 (d, J=4.3 Hz, 3H). MS (ESI): found [M+H]+, 543.5.

Cyclo-$^D$Asp(Pro-$^D$Pro-Val)-NHCH$_2$CH$_2$S—SCH$_2$CH$_2$NH$_2$ (26b)

The amine-containing peptide 26b was synthesized from 4b by following the above general procedure for EDCl peptide coupling of pendent carboxylic acid with cysteamine diamine and purified by HPLC using 11-35% acetonitrile gradient over 30 minutes, obtaining the desired homodimer as a viscous oil (yield, 65%; purity by LC-MS, 97%). $^1$H NMR (400 MHz, CDCl$_3$) δ ppm: 8.27 (t, J=4.7 Hz, 1H), 7.77 (br. s., 2H), 7.37 (d, J=8.2 Hz, 1H), 6.77 (d, J=7.0 Hz, 1H), 4.97-4.84 (m, 1H), 4.70-4.53 (m, 2H), 3.95 (t, J=9.2 Hz, 1H), 3.90-3.80 (m, 1H), 3.79-3.69 (m, 1H), 3.69-3.58 (m, 1H), 3.58-3.45 (m, 2H), 3.36-3.18 (m, 4H), 3.14-3.04 (m, 1H), 3.02-2.89 (m, 3H), 2.73 (dd, J=4.5, 16.2 Hz, 1H), 2.37-2.17 (m, 4H), 2.11-1.87 (m, 5H), 0.98 (d, J=6.3 Hz, 6H). MS (ESI): found [M+H]+, 543.5.

Example 9: KDAC Inhibition Assays

A selection of largazole analogs was assayed for inhibitory activity against three human KDACs to clarify how the different CTPs can derive isoform selectivity (Tables 1 and 2; FIG. 1A, FIG. 1B, FIG. 1C, and FIG. 1D). In vitro assays were performed on recombinant human KDACs 1, 3 and 8 (Class I KDACs) and KDAC 6 (Class II KDACs) using the Caliper EZ Reader II system (Life Sciences, USA).

Fluorescent substrates were purchased from PerkinElmer: two (FITC)-labeled peptides (p53 Acetylated Peptide and Histone 4 Acetylated Peptide, Product Number 760512 and 760513, respectively) were used as substrates to test compounds against KDAC 3 and 6, respectively; a (FAM)-labeled peptide (Broad Substrate B, Product Number CLS960007) was employed as substrate for KDAC8 assays.

As reference compounds, KDAC inhibitors: Entinostat (MS-275), Trichostatin A (TSA), Tubastatin A, Vorinostat (SAHA, MK0683)(purchased from Selleck Chemicals), and PCI-34051 (purchased from Cayman Chemical Company), and T247 were used. Largazole and one of its analogs (herein named SD-L-256), were generously supplied by Prof. Robert Williams of the Department of Chemistry at Colorado State University. The structures of these compounds are provided below:

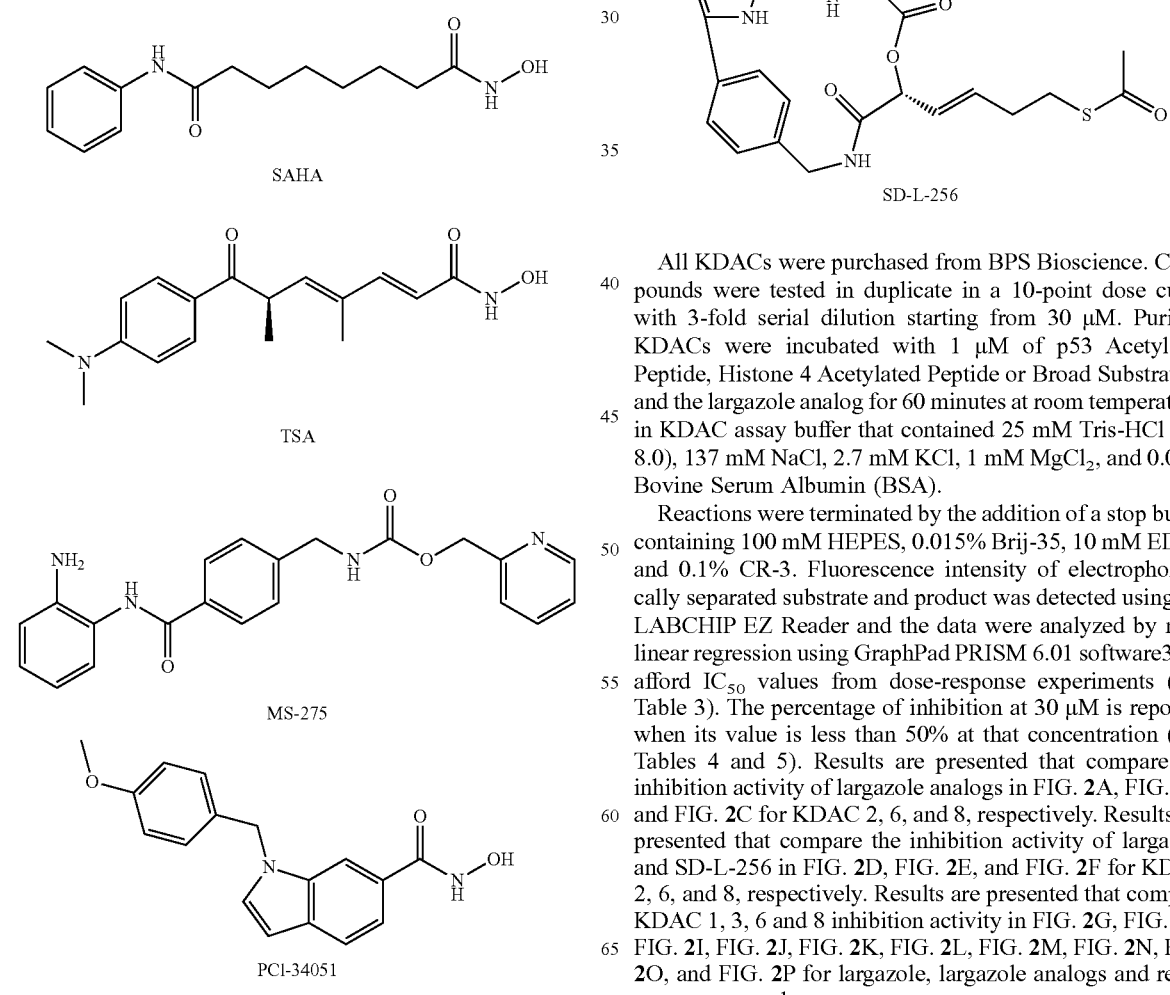

All KDACs were purchased from BPS Bioscience. Compounds were tested in duplicate in a 10-point dose curve with 3-fold serial dilution starting from 30 µM. Purified KDACs were incubated with 1 µM of p53 Acetylated Peptide, Histone 4 Acetylated Peptide or Broad Substrate B and the largazole analog for 60 minutes at room temperature, in KDAC assay buffer that contained 25 mM Tris-HCl (pH 8.0), 137 mM NaCl, 2.7 mM KCl, 1 mM $MgCl_2$, and 0.01% Bovine Serum Albumin (BSA).

Reactions were terminated by the addition of a stop buffer containing 100 mM HEPES, 0.015% Brij-35, 10 mM EDTA and 0.1% CR-3. Fluorescence intensity of electrophoretically separated substrate and product was detected using the LABCHIP EZ Reader and the data were analyzed by non-linear regression using GraphPad PRISM 6.01 software33 to afford $IC_{50}$ values from dose-response experiments (See Table 3). The percentage of inhibition at 30 µM is reported when its value is less than 50% at that concentration (See Tables 4 and 5). Results are presented that compare the inhibition activity of largazole analogs in FIG. 2A, FIG. 2B, and FIG. 2C for KDAC 2, 6, and 8, respectively. Results are presented that compare the inhibition activity of largazole and SD-L-256 in FIG. 2D, FIG. 2E, and FIG. 2F for KDAC 2, 6, and 8, respectively. Results are presented that compare KDAC 1, 3, 6 and 8 inhibition activity in FIG. 2G, FIG. 2H, FIG. 2I, FIG. 2J, FIG. 2K, FIG. 2L, FIG. 2M, FIG. 2N, FIG. 2O, and FIG. 2P for largazole, largazole analogs and reference compounds.

TABLE 1

KDAC Inhibition Activity (pIC₅₀) of Largazole Analogs of Formula IIa and IIb, wherein $R^1$ = L-Val % Inhibition at 30 μM (left structure: D-Pro, L-Pro, L-Asp, L-Val) | % Inhibition at 30 μM (right structure: D-Pro, L-Pro, D-Asp, L-Val)

| Cmpd | KDAC1 | KDAC3 | KDAC6 | KDAC8 | R | Cmpd | KDAC1 | KDAC3 | KDAC6 | KDAC8 |
|------|-------|-------|-------|-------|---|------|-------|-------|-------|-------|
| 1a | Not active | Not active | 6% | 9% | OBn | 1b | 7% | 10% | 8% | 9% |
| 3a | Not active | 1% | Not active | Not active | OH | 3b | 2.5% | 3% | Not active | Not active |
| 5a | Not active | Not active | 14% | 12% | —NH—CH₂CH₂—SH | 5b | Not active | Not active | 23% | 6% |
| 6a | 8% | 17-31% 24% average | 15-36% 26% average | 6% | —NH—(CH₂)₃—SH | 6b | Not active | 9% | Not active | 8% |
| 7a | Not active | Not active | 6% | 5% | —NH—(CH₂)₃—SMe | 7b | 1.5% | Not active | Not active | 28% |
| 8a | Not active | Not active | Not active | 30% | —NH—(CH₂)₃—S(O)Me | 8b | 3.5% | 5% | 3% | 38% |
| 9a | Not active | 4% | Not active | 17% | —NH—(CH₂)₃—S(O)₂Me | 9b | 4% | 3% | 1% | 22% |
| 10a | Not active | 1% | 1% | 26% | —NH—(CH₂)₃—OH | 10b | 1% | 9% | 1% | 25% |
| 11a | 2.5% | 10% | Not active | 31% | disulfide with NHP(O)(OPh)₂ | 11b | Not active | 4% | 16% | 10% |
| 12a | 54.6% | 2% | Not active | Not active | —HN—(CH₂)₃—CO₂Me | 12b | 5% | Not active | Not active | Not active |
| 13a | Not active | Not active | Not active | 3% | —NH—(CH₂)₃—CO₂H | 13b | 2.5% | Not active | Not active | Not active |
| 14a | 4.5% | 67% | 82% | 31% | —NH—(CH₂)₃—C(O)NHOH | 14b | 12.5% | 27% | 53% | 21% |

TABLE 1-continued

KDAC Inhibition Activity (pIC$_{50}$) of Largazole Analogs of Formula IIa and IIb, wherein R$^1$ = L-Val

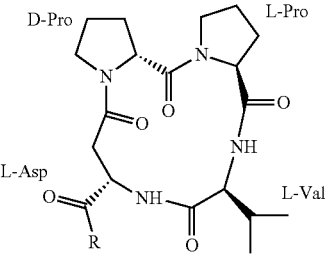

% Inhibition at 30 μM

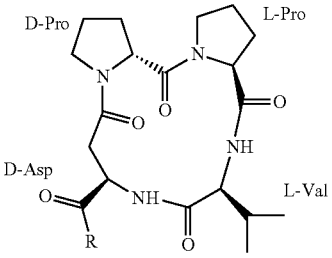

% Inhibition at 30 μM

| Cmpd | KDAC1 | KDAC3 | KDAC6 | KDAC8 | R | Cmpd | KDAC1 | KDAC3 | KDAC6 | KDAC8 |
|---|---|---|---|---|---|---|---|---|---|---|
| 15a | Not active | Not active | Not active | 1% | 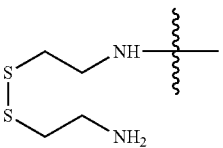 [SMILES: *NCCSSCCN] | 15b | 5% | 7% | 7% | Not active |
| 16a | Not active | 14%$^a$ | 2%$^a$ | 22%$^a$ | 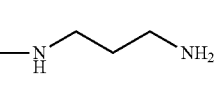 | 16b | 4.5% | 14%$^a$ | 2%$^a$ | 22%$^a$ |
| 35a | Not active | 2% | Not active | Not active | disulfide | 35b | Not active | Not active | 6% | 9% |
| 37a | Not active | Not active | 9% | 6% | disulfide | 37b | 1% | 53% | 8% | Not active |

$^a$A mixture of non-separable diastereomers.

TABLE 2

KDAC inhibition activity (pIC$_{50}$) of Largazole Analogs of Formula IIc and IId, wherein R$^1$ = L-Val

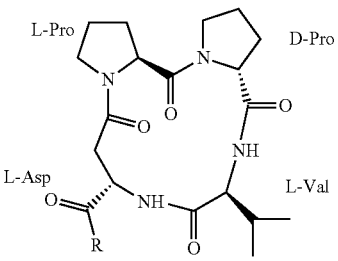

% Inhibition at 30 μM

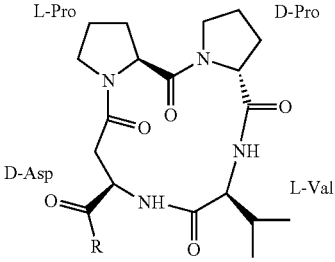

% Inhibition at 30 μM

| Cmpd | KDAC1 | KDAC3 | KDAC6 | KDAC8 | R | Cmpd | KDAC1 | KDAC3 | KDAC6 | KDAC8 |
|---|---|---|---|---|---|---|---|---|---|---|
| 2a | Not active | Not active | Not active | 14% | OBn | 2b | 1.5% | 1% | 10% | Not active |
| 4a | Not active | 24% | Not active | Not active | OH | 4b | Not active | 5% | 10% | 4% |
| 17a | Not active | 2% | 15% | 5% | 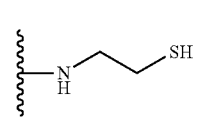 [SMILES: *NCCS] | 17b | Not active | Not active | 18% | Not active |
| 18a | Not active | 1% | 19% | 4% | 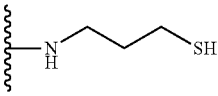 [SMILES: *NCCCS] | 18b | 9.5% | 15% | 48% | Not active |

TABLE 2-continued

KDAC inhibition activity (pIC$_{50}$) of Largazole Analogs of Formula IIc and IId, wherein R$^1$ = L-Val % Inhibition at 30 μM (left: L-Pro/D-Pro/L-Asp/L-Val structure; right: L-Pro/D-Pro/D-Asp/L-Val structure)

| Cmpd | KDAC1 | KDAC3 | KDAC6 | KDAC8 | R | Cmpd | KDAC1 | KDAC3 | KDAC6 | KDAC8 |
|---|---|---|---|---|---|---|---|---|---|---|
| 19a | 2% | Not active | Not active | 25% | —NH—(CH₂)₃—SMe | 19b | 1% | Not active | Not active | 27% |
| 20a | Not active | Not active | Not active | 19% | —NH—(CH₂)₃—S(O)Me | 20b | 1% | 16% | 1% | 10% |
| 21a | Not active | Not active | Not active | 23% | —NH—(CH₂)₃—S(O)₂Me | 21b | Not active | Not active | 12% | 8% |
| 22a | Not active | 7% | Not active | Not active | —NH—(CH₂)₃—OH | 22b | Not active | 5% | Not active | 12% |
| 23a | Not active | 7% | Not active | Not active | —NH—(CH₂)₃—CO₂Me | 23b | 1% | Not active | 5% | 7% |
| 24a | 4% | 8% | Not active | 36% | —NH—(CH₂)₃—CO₂H | 24b | Not active | 9% | Not active | 38% |
| 25a | 25% | 45% | 80% | 34% | —NH—(CH₂)₃—C(O)NHOH | 25b | Not active | 13% | 6% | 31% |
| 26a | 15% | 5% | 10% | 10% | cystamine-linked (S—S—CH₂CH₂—NH₂) | 26b | Not active | Not active | 13% | 4% |
| 36a | Not active | Not active | Not active | 2% | disulfide | 36b | Not active | Not active | 4% | 2% |
| 38a | Not active | 10% | 21% | Not active | disulfide | 38b | Not active | 19% | 40% | 3% |

[a]A mixture of non-separable diastereomers.

TABLE 3

KDAC Inhibition Activity (IC$_{50}$) of Most Active Largazole Analogs and Standard Compounds (% inhibition at 30 μM)

| | IC$_{50}$ μM | | | |
|---|---|---|---|---|
| Compound | KDAC1 | KDAC3 | KDAC6 | KDAC8 |
| 14a | 25.1 | 13.7 | 5.07 | >30 |
| 25a | >30 | >30 | 7.66 | >30 |
| MS-275 | 1.48 | 0.79 | >30 | >30 |
| Largazole | 2.33 | 1.36 | 9.29 | >30 |
| PCI-34051 | 14.41 | >30 | 4.57 | 0.49 |
| SAHA | 0.0070 | 0.0014 | 0.0014 | 0.50 |
| SD-L-256 | 3.48 | 0.47 | 1.61 | >30 |
| T247 | 1.11 | 3.94 | >30 | >30 |
| TSA | 0.015 | 0.020 | 0.038 | 4.55 |
| Tubastatin A | 2.87 | 0.77 | 0.014 | 2.34 |

TABLE 4

KDAC Inhibition Activity (pIC$_{50}$) of Standard Compounds (% inhibition at 30 μM)

| | pIC$_{50}$ | | |
|---|---|---|---|
| Compound | KDAC3 | KDAC6 | KDAC8 |
| Entinostat | 6.10 | Not Active | 4.61 |
| SAHA(Vorinostat) | 8.92 | 8.85 | 6.31 |
| Tubastatin A | 6.11 | 7.84 | 5.63 |
| Trichostatin A | 7.70 | 7.42 | 5.34 |
| PCI-34051 | 25%[b] | 5.34 | 6.31 |

TABLE 5

KDAC Inhibition Activity (pIC$_{50}$) of largazole and analog SDL256 (% inhibition at 30 μM)

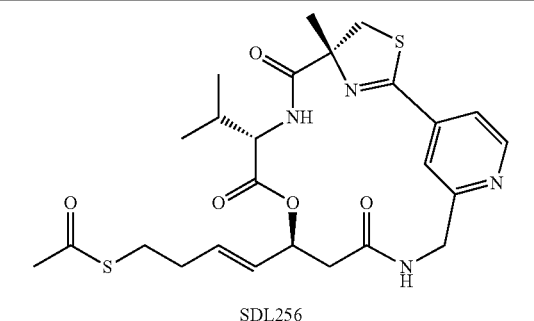

LARGAZOLE

| | pIC$_{50}$ | | |
|---|---|---|---|
| KDAC1 | KDAC3 | KDAC6 | KDAC8 |
| | 5.87 | 5.03 | 28%[a] |

SDL256

TABLE 5-continued

KDAC Inhibition Activity (pIC$_{50}$) of largazole and analog SDL256 (% inhibition at 30 μM)

| pIC$_{50}$ | | | |
|---|---|---|---|
| KDAC1 | KDAC3 | KDAC6 | KDAC8 |
| | 6.32 | 5.79 | 39%[a] |

Example 10: Largazoles Reactivate HIV from Latency

Figure 3A:
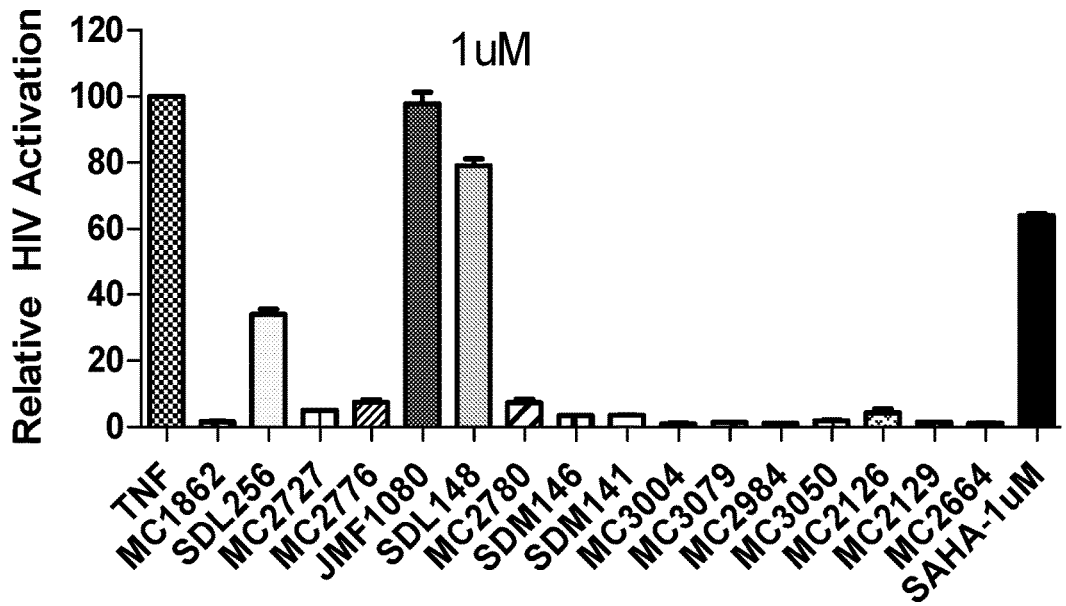
FIG. 3A: Results of an experiment to show that largazole (SDL148) and largazole analogs reactivate HIV from latency in cells.
Figure 3B:
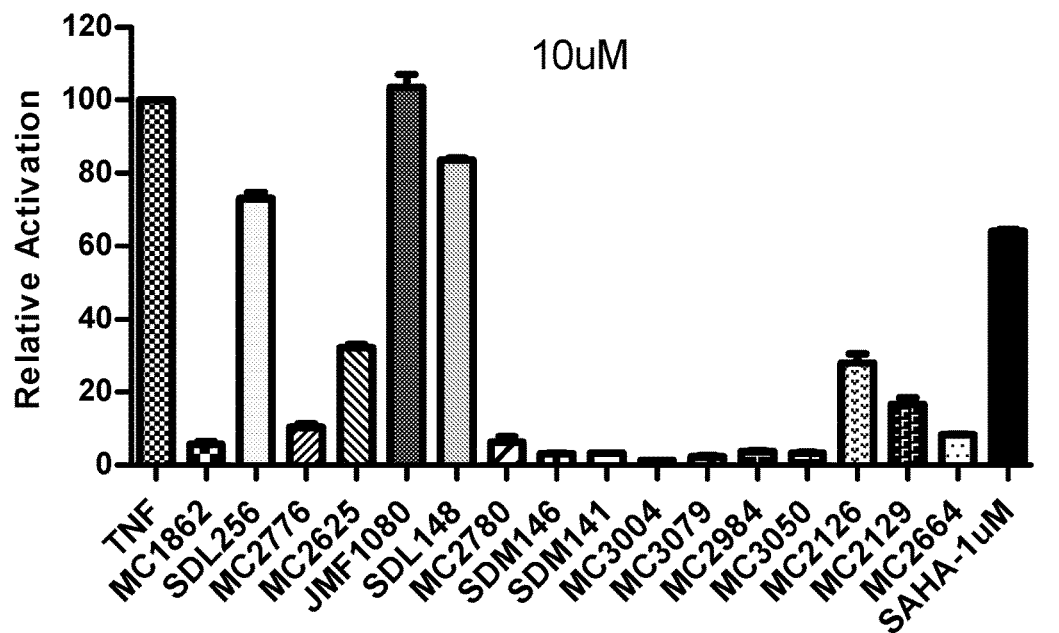
FIG. 3B: Results of an experiment to show that largazole (SDL148) and largazole analogs reactivate HIV from latency in cells.

JLAT 10.6 cells, which have HIV-1-GFP stably integrated, were incubated with the indicated compounds for 24 hours. At baseline cells do not produce HIV. Upon stimulation with an appropriate agent, they can produce HIV as measured by GFP recognition with fluorescent-activated cell sorting (FACS). Cells were fixed and FACS performed for GFP as a surrogate for HIV production using TNF alpha as positive control. Largazoles are SDL256, JMF 1080, and SDL148. Relative activation is normalized to TNF alpha. These results are presented in FIG. 3A and FIG. 3B.

Figure 3C:
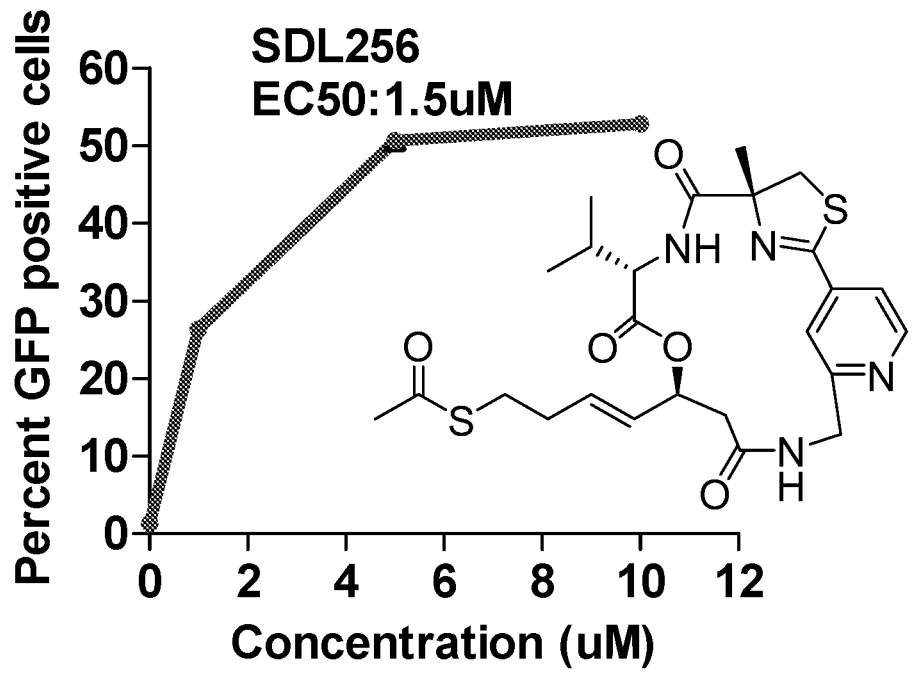
FIG. 3C: Graph of effective concentration (EC$_{50}$) of a largazole analog (SDL256) tested on reactivate HIV from latency in cells.
Figure 3D:
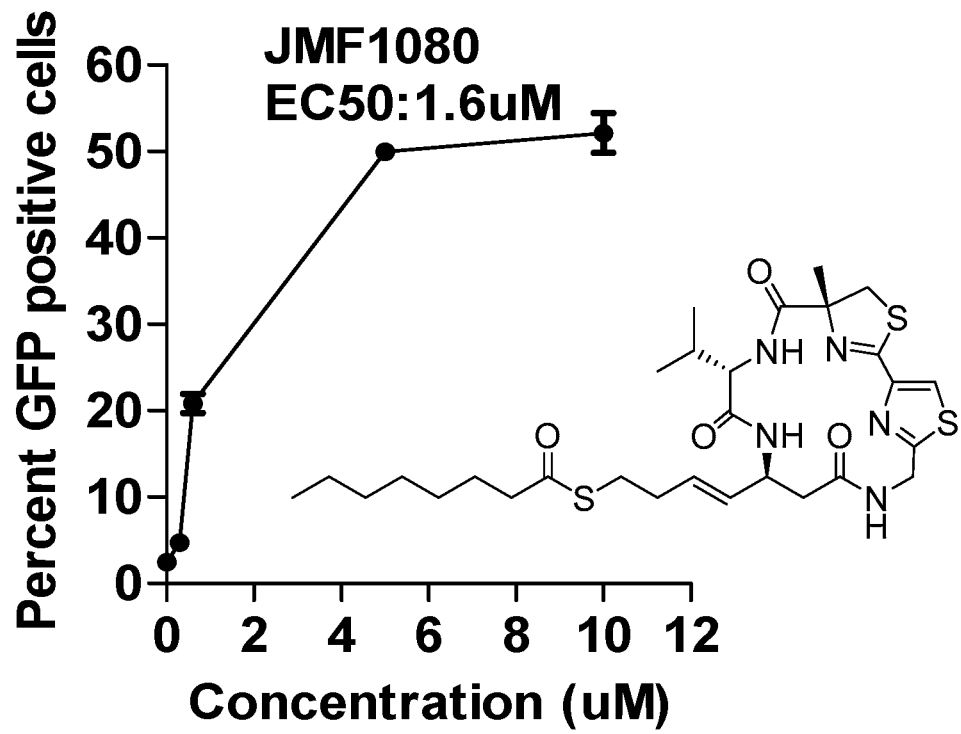
FIG. 3D: Graph of effective concentration (EC$_{50}$) of a largazole analog (JMF1080) tested on reactivate HIV from latency in cells.
Figure 3E:
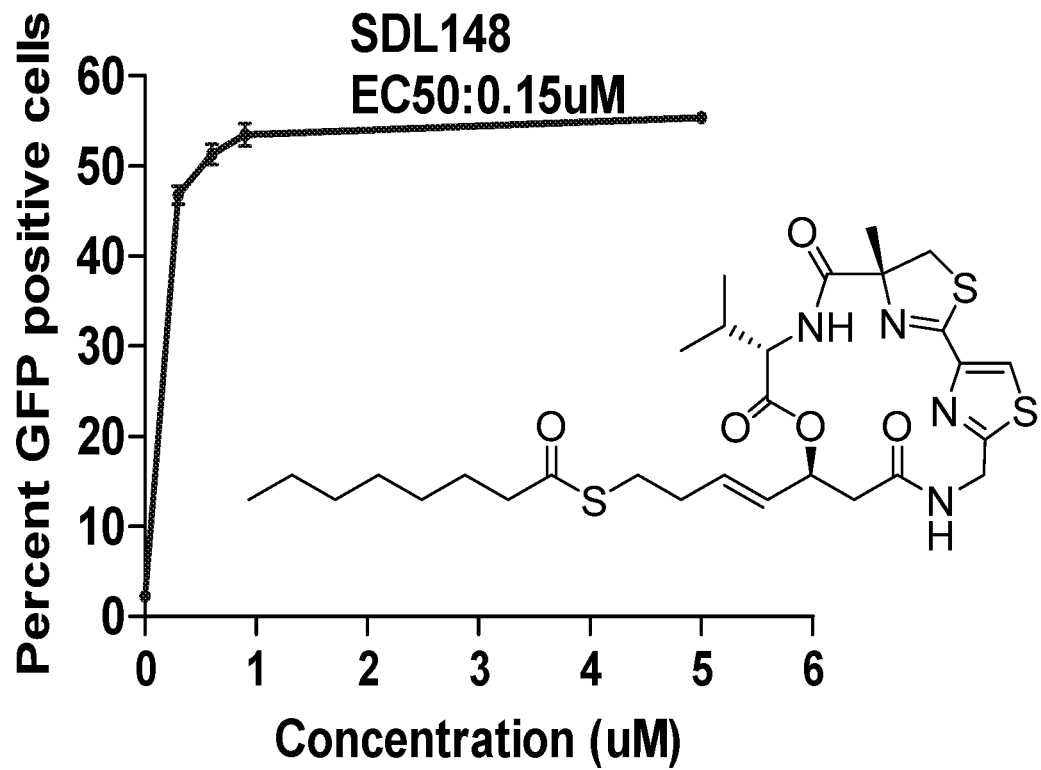
FIG. 3E: Graph of effective concentration (EC$_{50}$) of largazole (SDL148) tested on reactivate HIV from latency in cells.

Three compounds: SDL148 (largazole), JMF1080 and SDL256 (largazole analogs) were found comparable to, or more potent than vorinostat in reactivating HIV from latency, with EC50 values of 0.15, 1.6 and 1.6 μM respectively. These results are presented in FIG. 3C, FIG. 3D, and FIG. 3E.

Figure 2A:
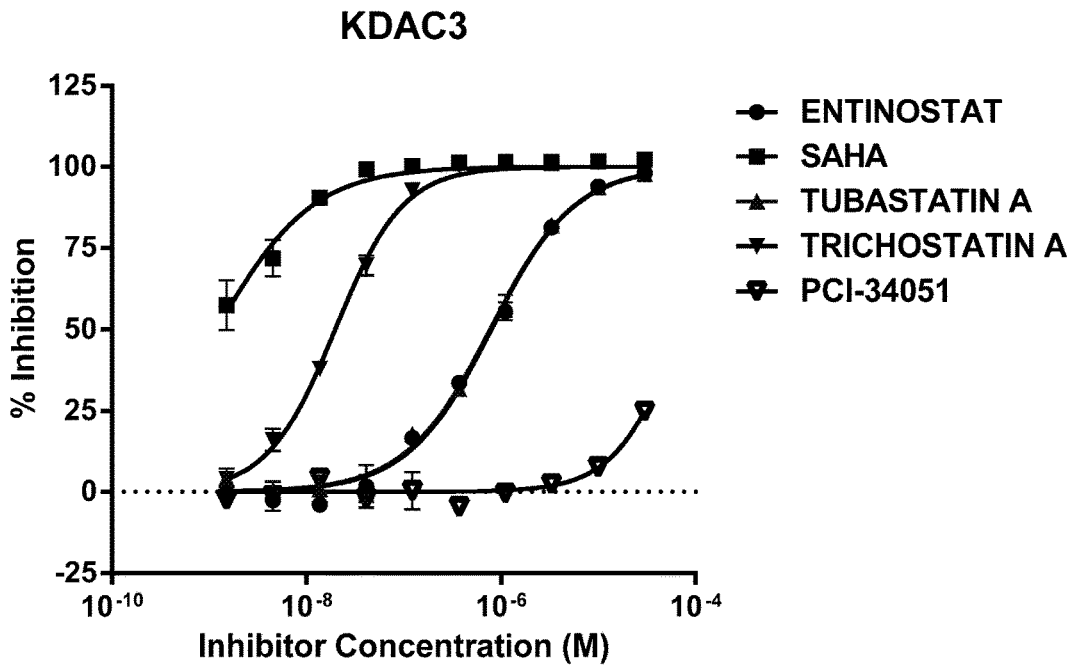
FIG. 2A: Graph of dose response plots of standard compounds tested on recombinant human KDAC 3.
Figure 2B:
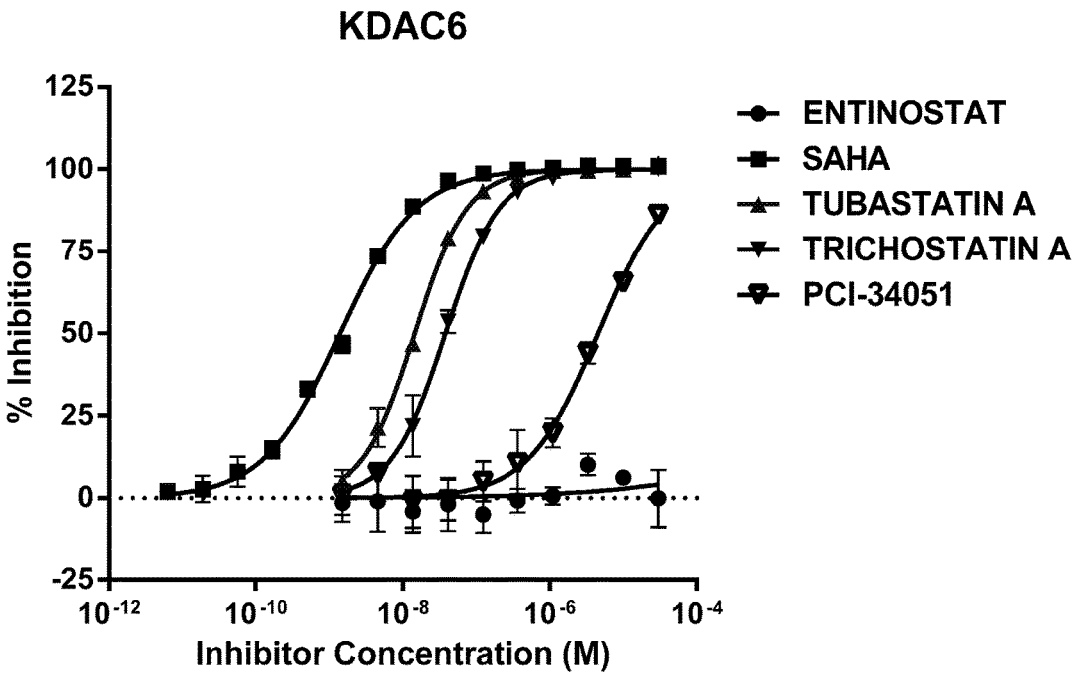
FIG. 2B: Graph of dose response plots of standard compounds tested on recombinant human KDAC 6.
Figure 2C:
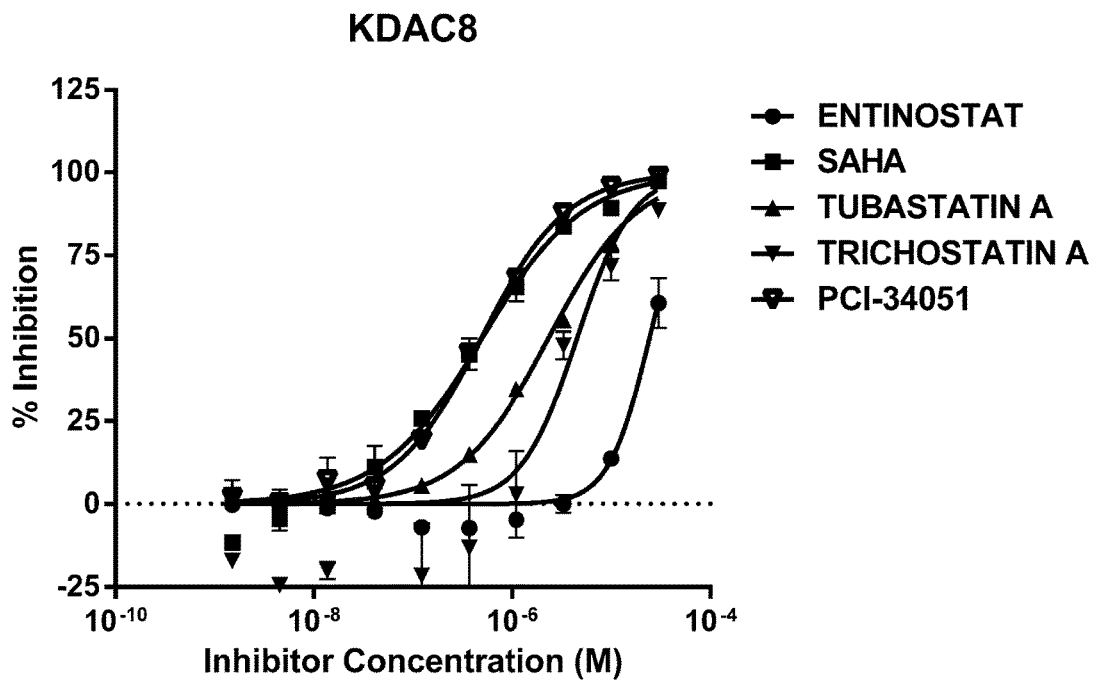
FIG. 2C: Graph of dose response plots of standard compounds tested on recombinant human KDAC 8.
Figure 2D:
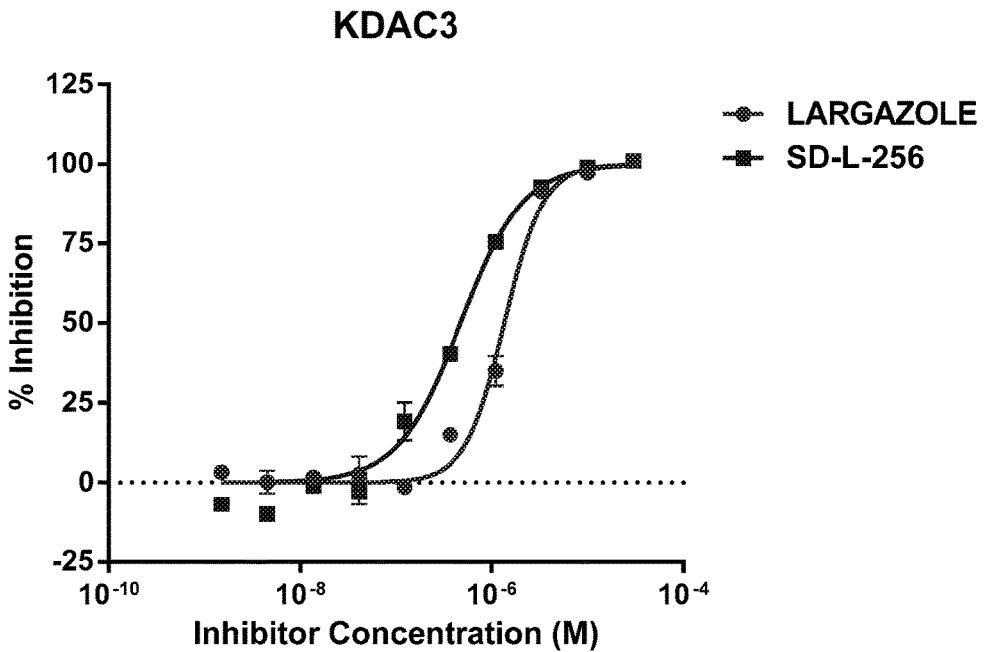
FIG. 2D: Graph of dose response plots of largazole and analog SD-L-256 tested on recombinant human KDAC 3.
Figure 2E:
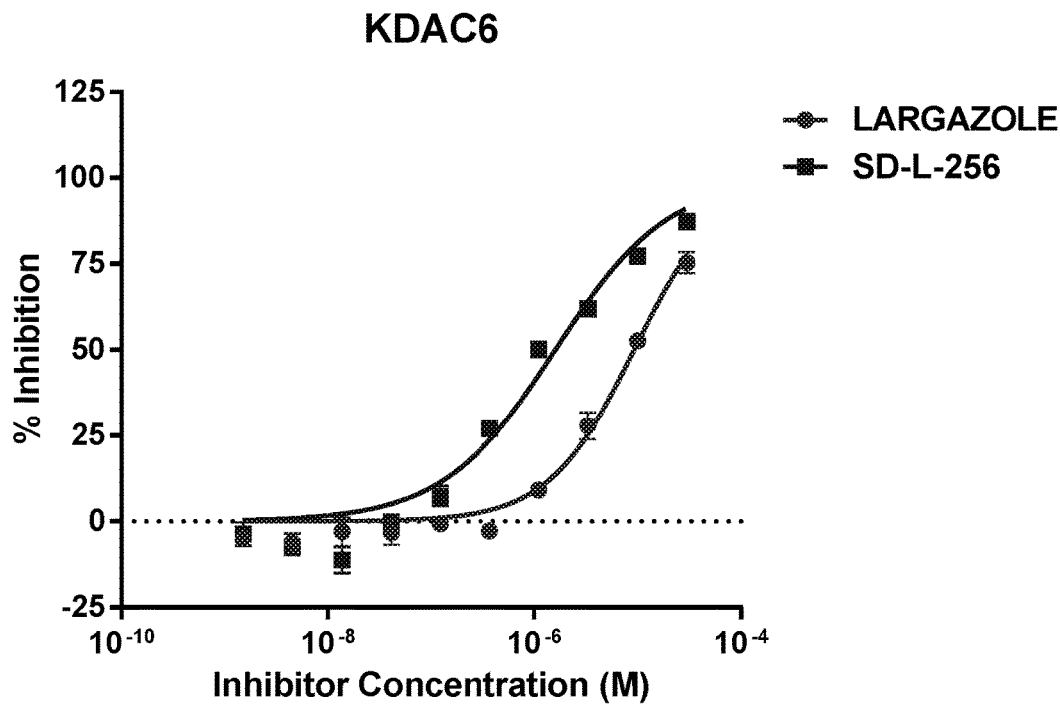
FIG. 2E: Graph of dose response plots of largazole and analog SD-L-256 tested on recombinant human KDAC 6.
Figure 2F:
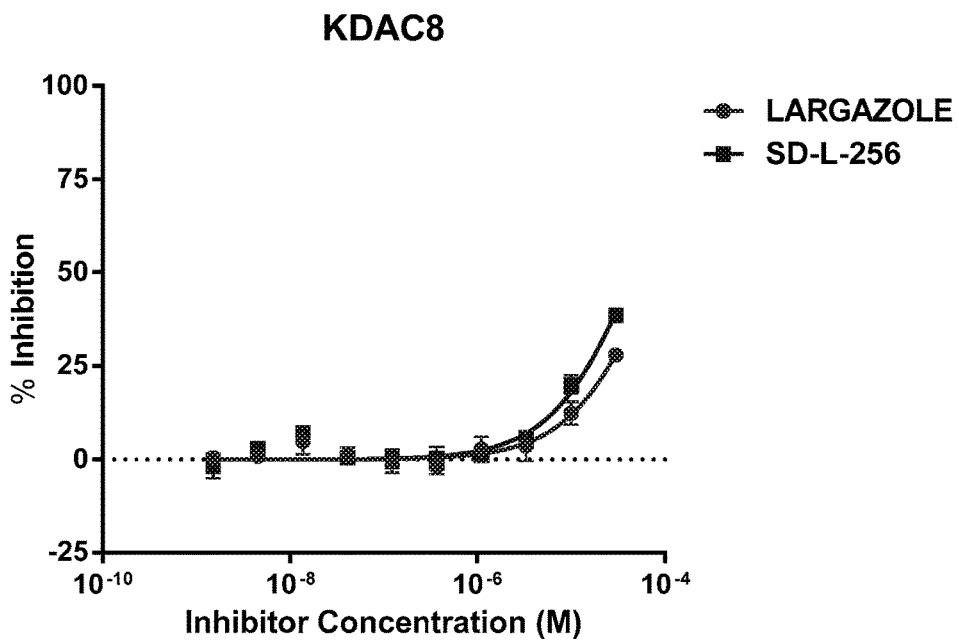
FIG. 2F: Graph of dose response plots of largazole and analog SD-L-256 tested on recombinant human KDAC 8.
Figure 2G:
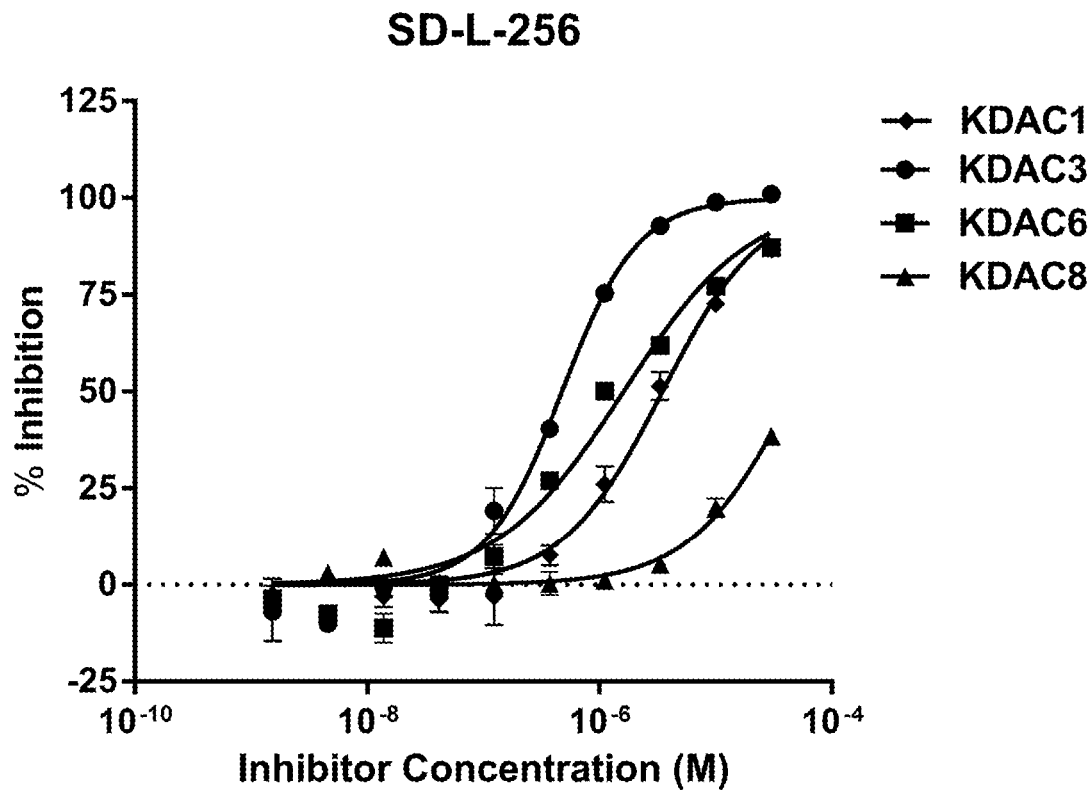
FIG. 2G: Graph of dose response plots of SD-L-256 tested on recombinant human KDAC 1, 3, 6, and 8.
Figure 2H:
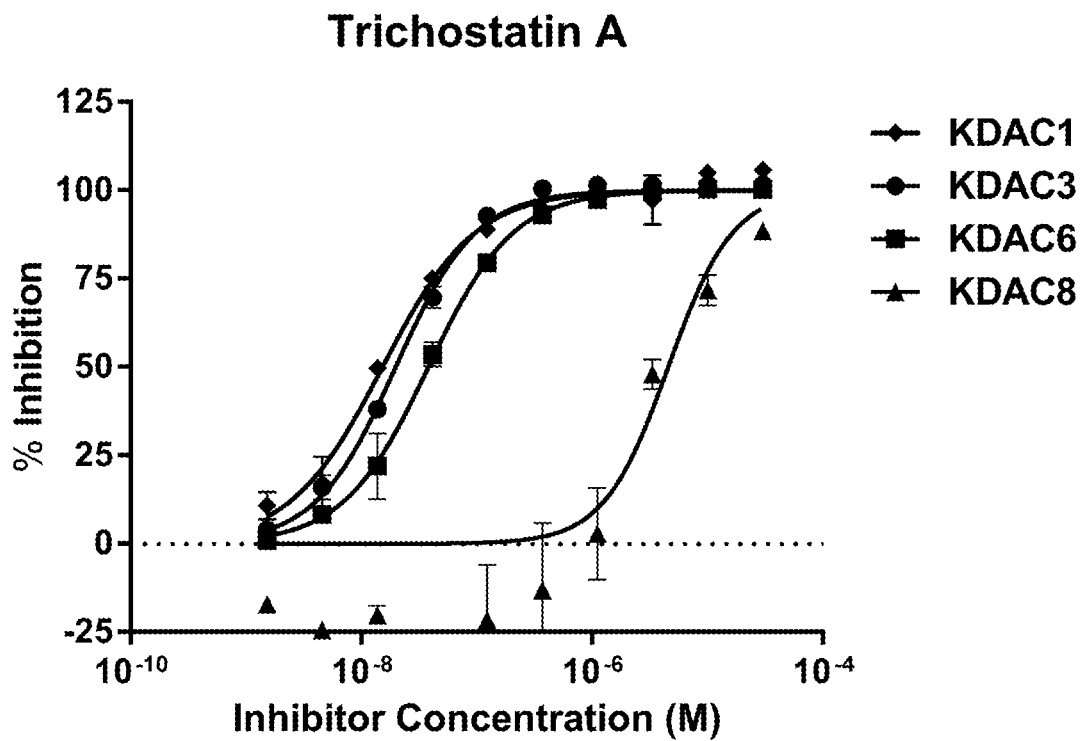
FIG. 2H: Graph of dose response plots of trichostatin A tested on recombinant human KDAC 1, 3, 6, and 8.
Figure 2I:
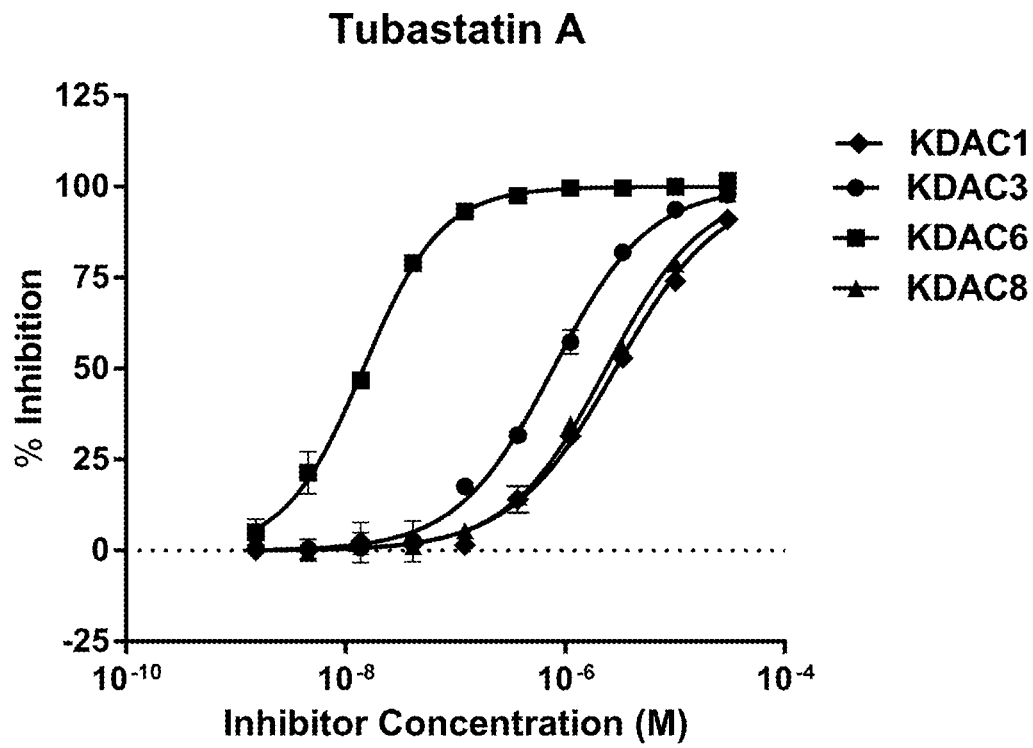
FIG. 2I: Graph of dose response plots of tubastatin A tested on recombinant human KDAC 1, 3, 6, and 8.
Figure 2J:
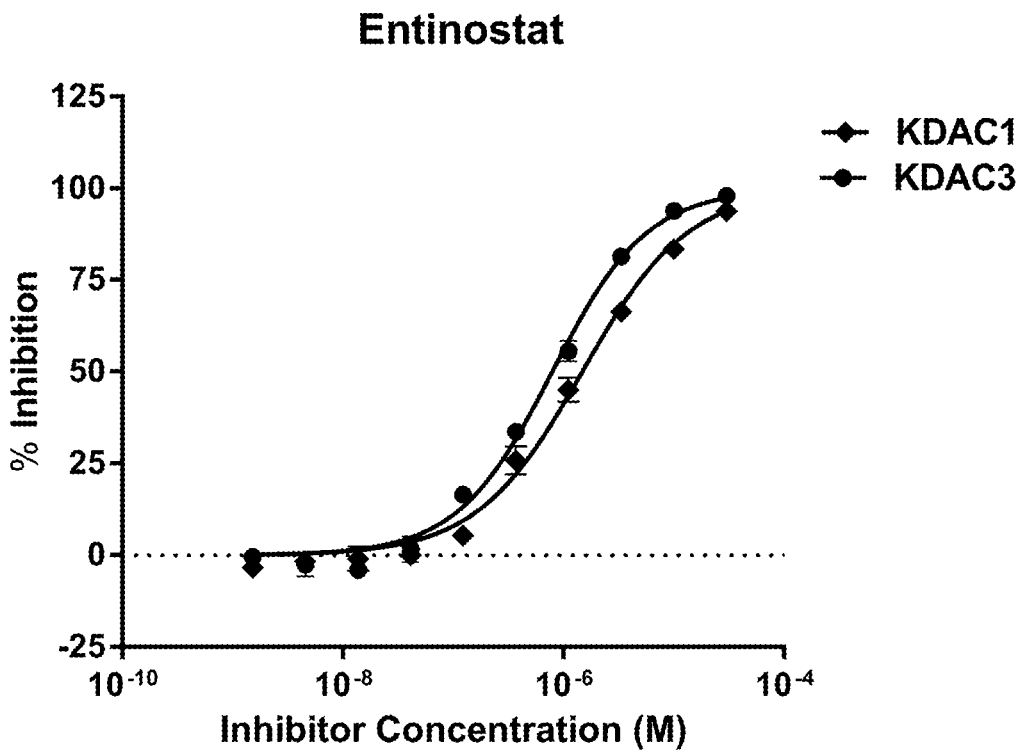
FIG. 2J: Graph of dose response plots of entinostat tested on recombinant human KDAC 1 and 3.
Figure 2K:
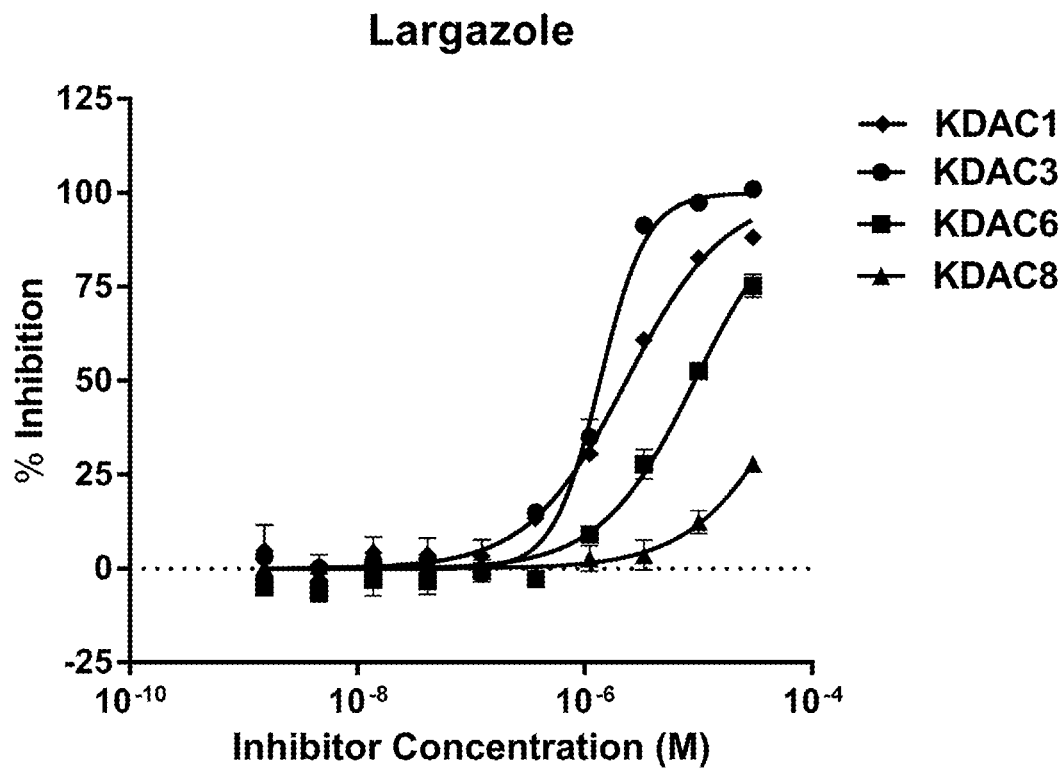
FIG. 2K: Graph of dose response plots of largazole tested on recombinant human KDAC 1, 3, 6, and 8.
Figure 2L:
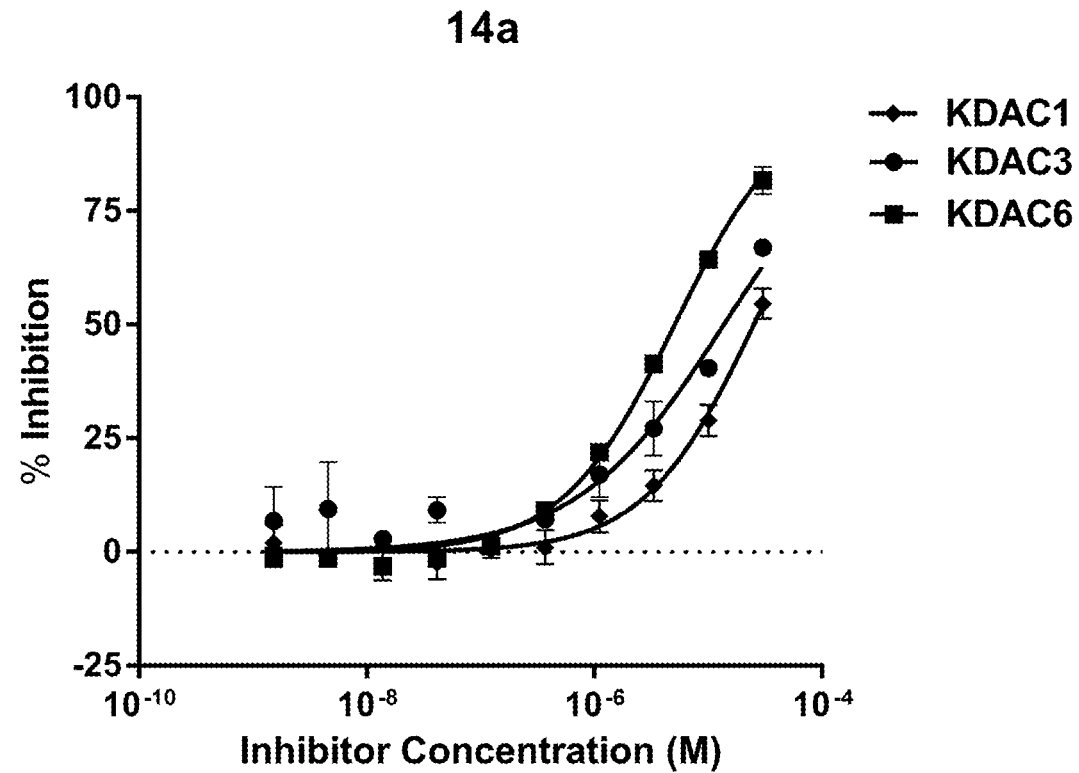
FIG. 2L: Graph of dose response plots of largazole analog 14a tested on recombinant human KDAC 1, 3, and 6.
Figure 2M:
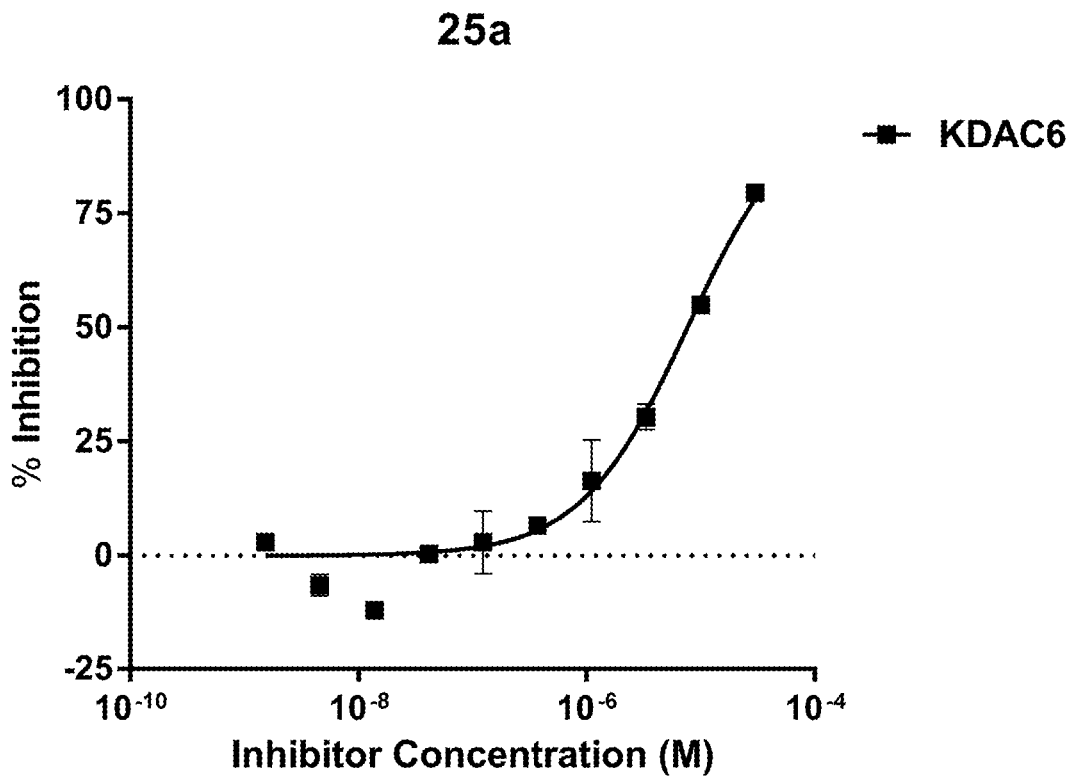
FIG. 2M: Graph of dose response plots of largazole analog 25a tested on recombinant human KDAC 6.
Figure 2N:
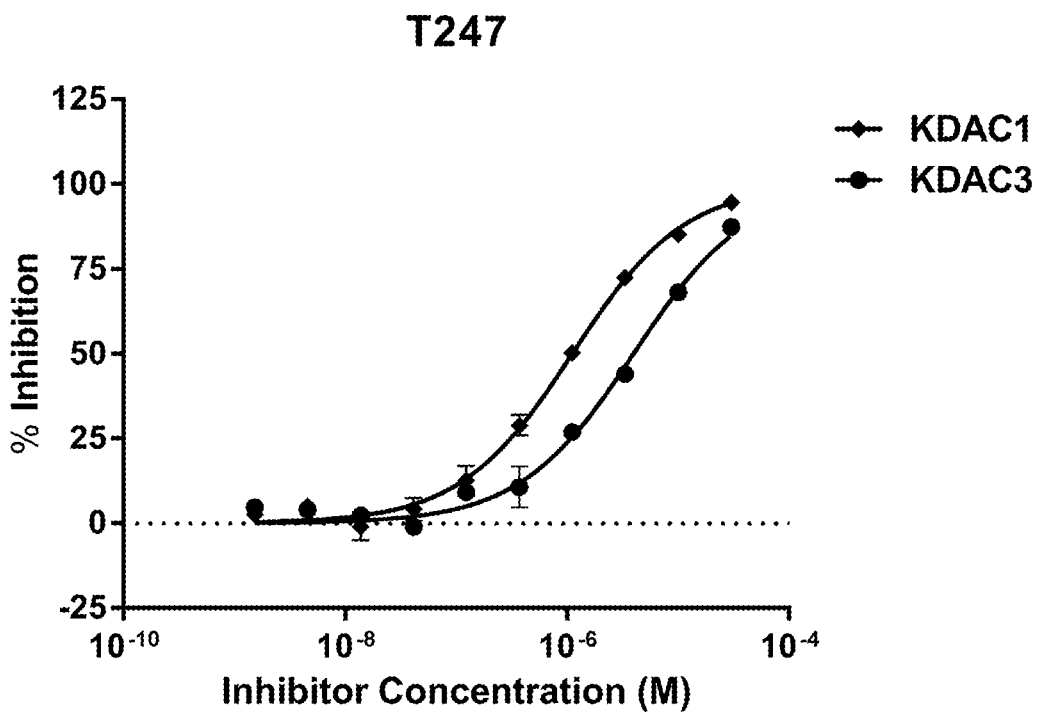
FIG. 2N: Graph of dose response plots of standard compound T247 tested on recombinant human KDAC 1 and 3.
Figure 2O:
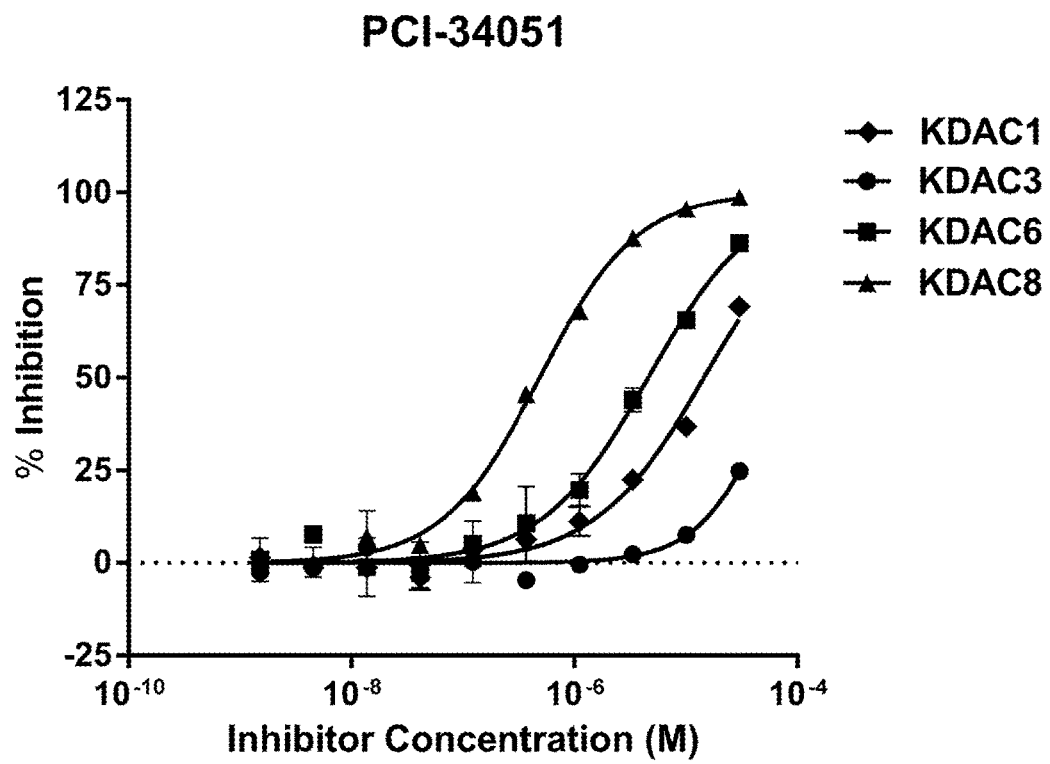
FIG. 2O: Graph of dose response plots of standard compound PCI-34051 tested on recombinant human KDAC 1, 3, 6, and 8.
Figure 2P:
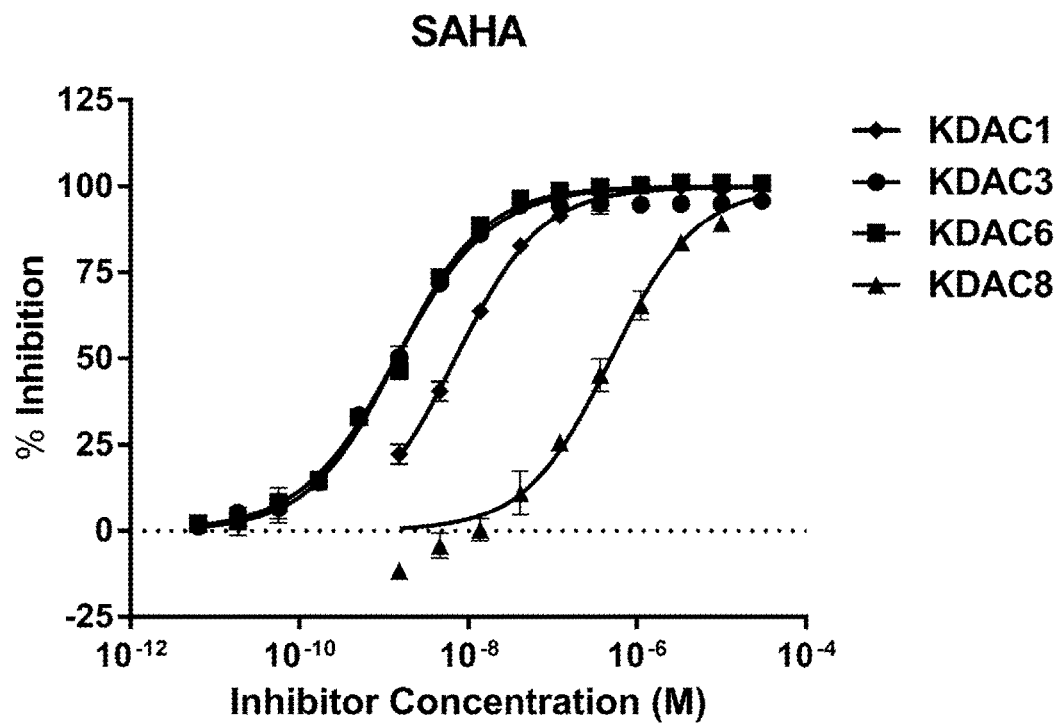
FIG. 2P: Graph of dose response plots of standard compound SAHA tested on recombinant human KDAC 1, 3, 6, and 8.
Figure 4A:
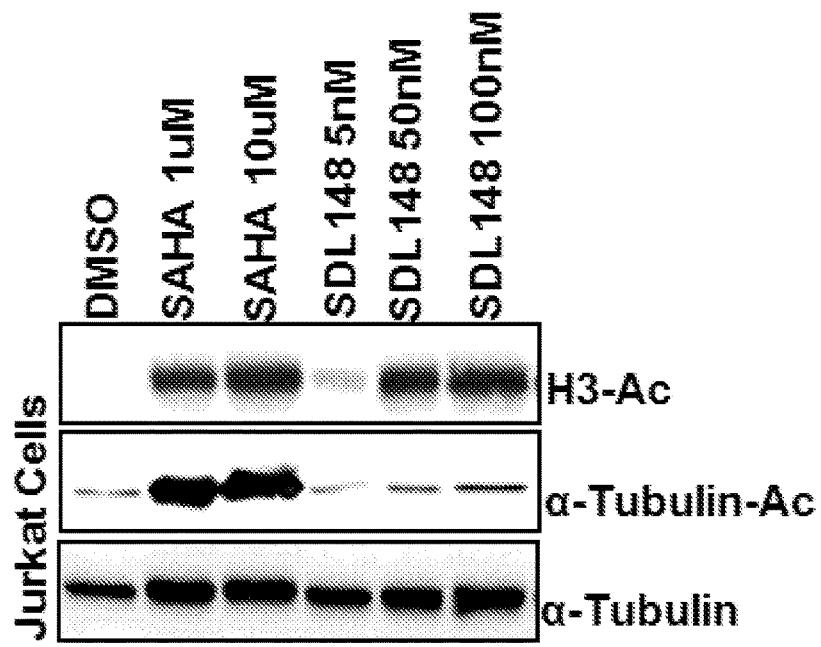
FIG. 4A: Results of an experiment to show largazole and largazole analogs are isoform specific class I KDACs.
Figure 4B:
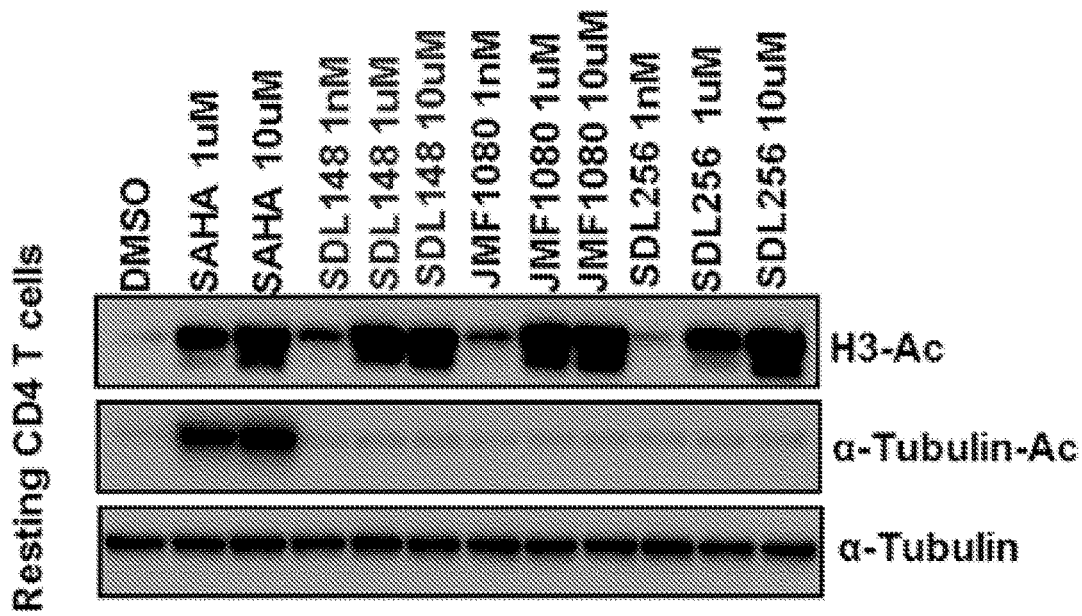
FIG. 4B: Results of an experiment to show largazole and largazole analogs are isoform specific class I KDACs.

Jurkat cells were incubated with SAHA or SDL148 at the indicated concentrations for 8 hours and Western blot performed for the levels of acetylated histone H3, acetylated tubulin, tubulin and actin (FIG. 2A). Resting T cells were isolated from an HIV negative donor and incubated with SAHA or the indicated largazoles for 8 h and Western blot performed (FIG. 2B). The pan-KDAC SAHA inhibit deacetylation of both histone H3 and tubulin (class II KDAC) while the largazoles inhibit the deacetylation of only the class I KDAC, histone H3. Western blots measuring histone H3 acetylation in Jurkat and primary T cells found that, unlike vorinostat, these compounds specifically inhibited class I KDACs, with SDL148 being 20 times more potent than vorinostat. See FIG. 4A and FIG. 4B.

Figure 5:
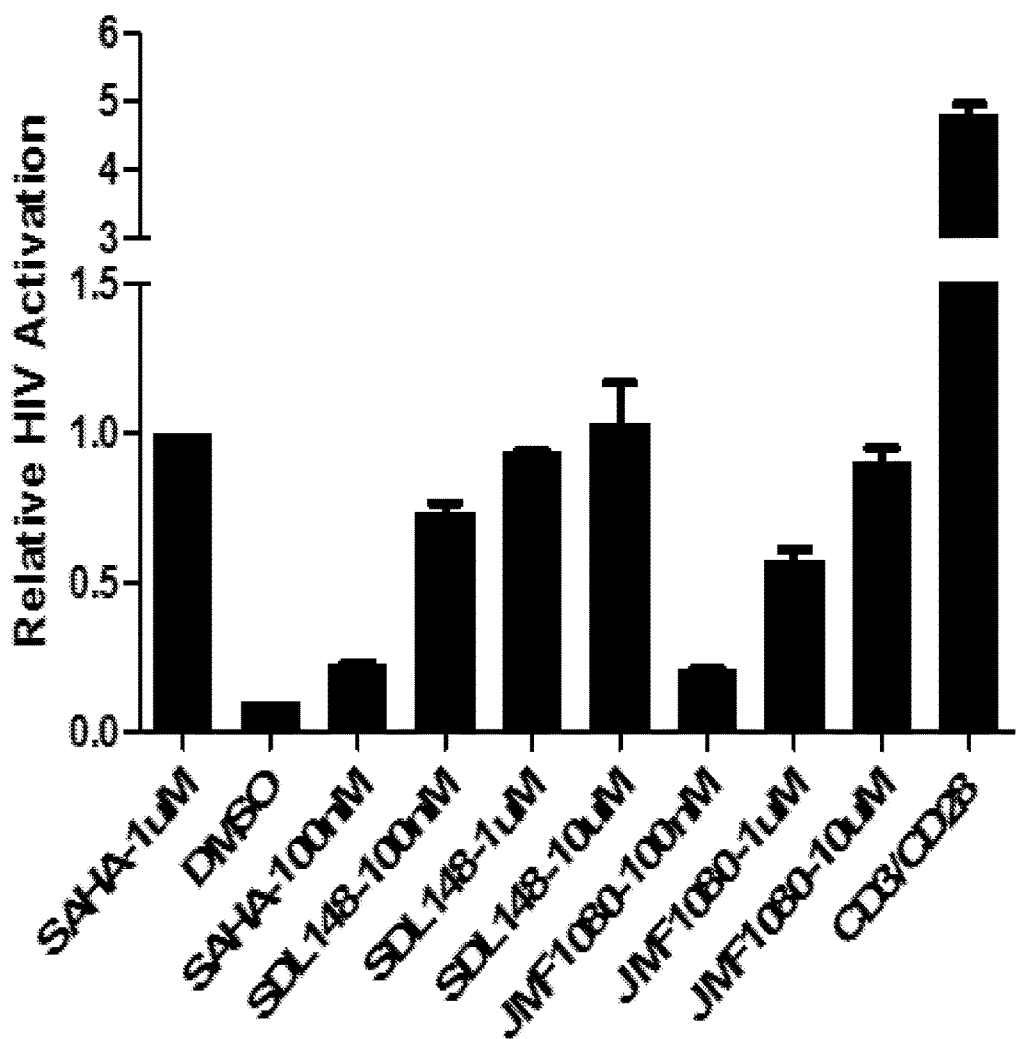
FIG. 5: Results of an experiment to show that largazole and largazole analogs reactivate HIV in a primary cell model of latency.

CD4+ T cells were isolated from an HIV-negative donor to establish HIV latency using the Greene model. Briefly cells were infected with a replication-competent HIV NL4-3Luc for 2 hours, washed and incubated with Darunavir for 3 days to establish latency. Latently infected cells were incubated with the indicated concentrations of compounds in the presence of Raltegravir for 48 hours. Cells were lysed and luciferase luminescence normalized to the levels produced by SAHA. Using the Greene model of HIV latency, the largazoles were able to reactivate HIV from latency in nanomolar concentrations in this primary cell model. See FIG. 5.

Figure 6:
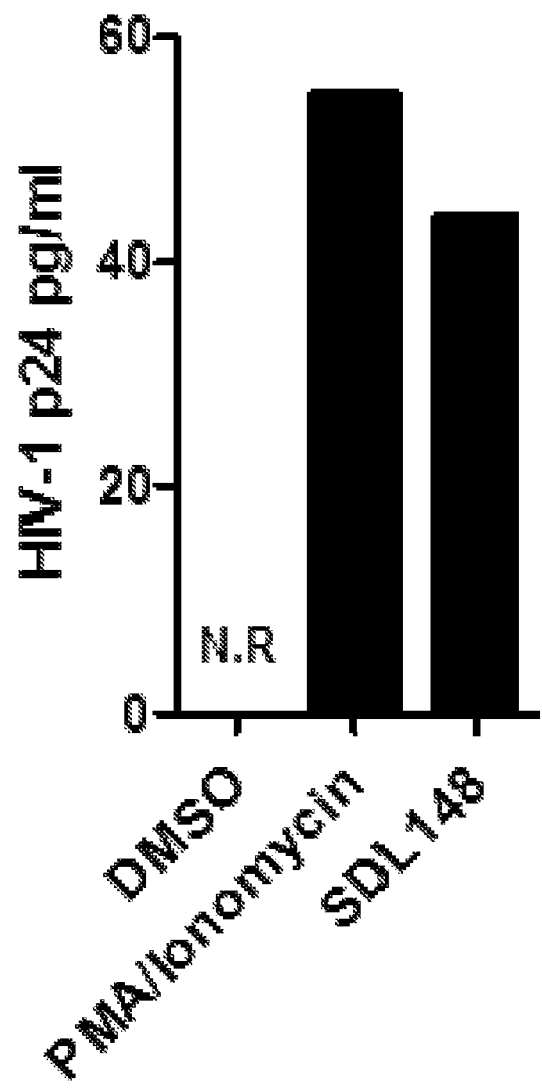
FIG. 6: Results of an experiment to show that largazole (SDL148) can reactivate HIV in a patient.

Resting CD4+ T cells were isolated from a patient fully suppressed on antiretroviral therapy and incubated with DMSO, 50 ng/mL PMA plus 1 μM ionomycin, or 1 μM SDL148 for 48 hours. Cells were washed and co-cultured with MOLT4/CCR5 cells for 7 days. R Cellular supernatants were collected for HIV-1 p24 ELISA. N.R—non reactive. Preliminary data in resting T-cells isolated from the virologically suppressed patient show that SDL148 was able to reactivate virus from latency as determined by HIV-1 p24 ELISA measurements in culture supernatants (FIG. 6). Thus, largazole and its analogs are isoform specific KDAC inhibitors that can reactivate HIV from latency.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying figures shall be interpreted as illustrative and not in a limiting sense.

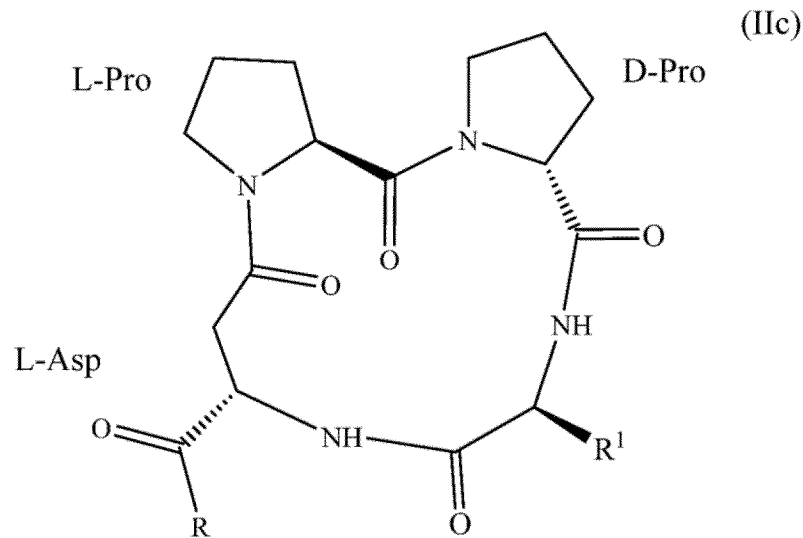

What is claimed is:

1. A compound of Formula I:

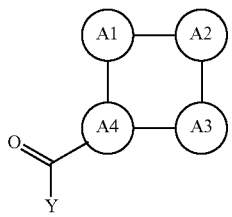

(I)

wherein
A1 is L-Pro or D-Pro and A2 is L-Pro or D-Pro with the proviso that A1 and A2 are not the same;
A3 is a natural or unnatural alpha-amino acid;
A4 is L- or D-aspartic acid wherein the α-carboxyl group is unprotected (Y=OH) or wherein the α-carboxyl group has been converted to an ester or amide derivative.

2. The compound of claim 1 wherein A3 is a naturally occurring alpha-amino acid or the D-stereoisomer thereof.

3. A pharmaceutical composition comprising a therapeutically effective amount of at least one compound of claim 1 and a pharmaceutically acceptable excipient.

4. A pharmaceutical composition comprising at least one compound of claim 1 wherein the compound is radiolabelled.

5. A compound of Formula IIa, IIb, IIc, or IId or a pharmaceutically acceptable salt, solvate, prodrug, or stereoisomer thereof:

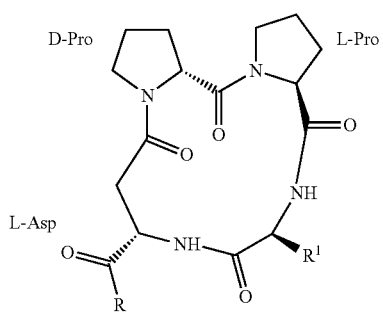

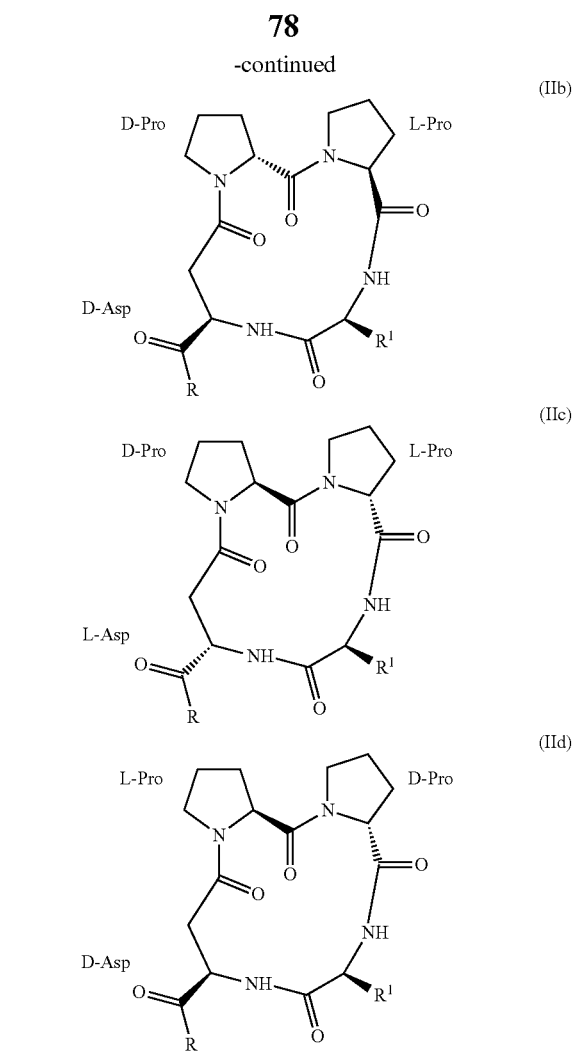

wherein
R is hydroxyl, substituted or unsubstituted alkoxy, substituted or unsubstituted aryloxy, substituted or unsubstituted arylalkyloxy, or substituted or unsubstituted amino; and
$R^1$ is a side chain of a naturally occurring L-amino acid.

6. The compound of claim 5 wherein R is substituted or unsubstituted amino.

7. The compound of claim 6 wherein R is substituted amino having the formula —NH—$(CH)_n$—$R^2$, where $R^2$ is OH, $SR^3$, $SOR^3$, $SO_2R^3$, $NR^3$, $CO_2R^3$, $C(O)NHOR^3$, S—S$(CH_2)_nNH_2$, —NH$(CH_2)_nS$—S$(CH_2)_nNHPO(OR^4)_2$; $R^3$ is hydrogen or $C_1$-$C_6$ alkyl; $R^4$ is hydrogen or phenyl; and n is a number from 2 to 5.

8. The compound of claim 5 wherein R is hydroxy, substituted or unsubstituted alkoxy, substituted or unsubstituted aryloxy, or substituted or unsubstituted arylalkyloxy.

9. The compound of claim 5 wherein $R^1$ is hydrogen or $C_1$-$C_6$ alkyl.

10. The compound of claim 5 wherein $R^1$ is hydrogen, methyl, isopropyl, isobutyl, or sec-butyl.

11. The compound of claim 7 wherein $R^1$ is hydrogen, methyl, isopropyl, isobutyl, or sec-butyl.

12. The compound of claim 8 wherein $R^1$ is hydrogen, methyl, isopropyl, isobutyl, or sec-butyl.

13. A pharmaceutical composition comprising a therapeutically effective amount of at least one compound of claim 5.

14. A method of inhibiting lysine deacetylase activity in a subject comprising administering to the subject a pharmaceutical composition comprising a therapeutically effective amount of at least one compound of claim 1.

15. A method of treating HIV-1 latency in a subject in need thereof comprising administering to the subject a pharmaceutical composition comprising a therapeutically effective amount of at least one compound of claim 1.

16. The method of claim 15 wherein the method further comprises administering an antiviral agent.

17. A method of inhibiting lysine deacetylase activity in a subject comprising administering to the subject a pharmaceutical composition comprising a therapeutically effective amount of at least one compound of claim 5.

18. A method of treating HIV-1 latency in a subject in need thereof comprising administering to the subject a pharmaceutical composition comprising a therapeutically effective amount of at least one compound of claim 5.

19. The method of claim 18 wherein the method further comprises administering an antiviral agent.

* * * * *

UNITED STATES PATENT AND TRADEMARK OFFICE
CERTIFICATE OF CORRECTION

PATENT NO. : 10,421,778 B2  
APPLICATION NO. : 15/570967  
DATED : September 24, 2019  
INVENTOR(S) : Marshall et al.

Page 1 of 2

It is certified that error appears in the above-identified patent and that said Letters Patent is hereby corrected as shown below:

In the Claims  
Column 78, Claim 5, Line 15:

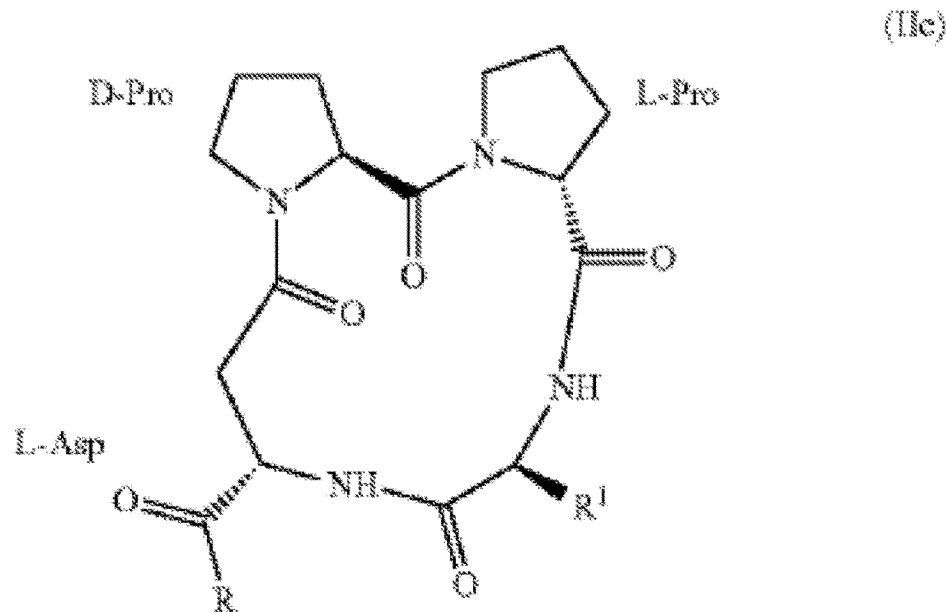

Signed and Sealed this  
Eleventh Day of February, 2020

Andrei Iancu  
*Director of the United States Patent and Trademark Office*

CERTIFICATE OF CORRECTION (continued)
U.S. Pat. No. 10,421,778 B2

Should read: